United States Patent
Bassett et al.

(10) Patent No.: US 11,261,470 B2
(45) Date of Patent: Mar. 1, 2022

(54) RECOMBINANT BACTERIAL HOST CELL FOR PROTEIN EXPRESSION

(71) Applicant: UCB BIOPHARMA SRL, Brussels (BE)

(72) Inventors: Philip Jonathan Bassett, Slough (GB); David Paul Humphreys, Slough (GB); Pareshkumar Manjibhai Patel, Slough (GB)

(73) Assignee: UCB BIOPHARMA SRL, Brussels (BE)

(*) Notice: Subject to any disclaimer, the term of this patent is extended or adjusted under 35 U.S.C. 154(b) by 0 days.

(21) Appl. No.: 15/959,498

(22) Filed: Apr. 23, 2018

(65) Prior Publication Data

US 2018/0258457 A1  Sep. 13, 2018

Related U.S. Application Data

(63) Continuation of application No. 14/400,068, filed as application No. PCT/EP2013/059803 on May 13, 2013, now Pat. No. 9,951,365.

(30) Foreign Application Priority Data

May 14, 2012  (GB) ..................... 1208367

(51) Int. Cl.
| | | |
|---|---|---|
| C12P 21/00 | (2006.01) | |
| C12P 21/02 | (2006.01) | |
| C12N 9/52 | (2006.01) | |
| C07K 16/28 | (2006.01) | |
| C12N 15/70 | (2006.01) | |

(52) U.S. Cl.
CPC ............ *C12P 21/00* (2013.01); *C07K 16/283* (2013.01); *C12N 9/52* (2013.01); *C12N 15/70* (2013.01); *C12P 21/02* (2013.01); *C07K 2317/10* (2013.01)

(58) Field of Classification Search
CPC ........... C12P 21/00; C12P 21/02; C12N 15/70
See application file for complete search history.

(56) References Cited

U.S. PATENT DOCUMENTS

| | | | |
|---|---|---|---|
| 5,264,365 A | 11/1993 | Georgiou et al. | |
| 5,508,192 A | 4/1996 | Georgiou et al. | |
| 5,665,866 A | 9/1997 | Weir et al. | |
| 6,027,888 A | 2/2000 | Georgiou et al. | |
| 6,083,715 A | 7/2000 | Georgiou et al. | |
| 6,306,619 B1 | 10/2001 | Jones et al. | |
| 7,012,135 B2 | 3/2006 | Athwal et al. | |
| 7,041,479 B2 | 5/2006 | Swartz et al. | |
| 7,419,659 B2 | 9/2008 | Popplewell | |
| 7,662,587 B1 | 2/2010 | Cheng et al. | |
| 8,293,237 B2 | 10/2012 | Burkly et al. | |
| 8,470,552 B2 | 6/2013 | Crougan et al. | |
| 8,784,823 B2 | 7/2014 | Burkly et al. | |
| 8,969,037 B2 | 3/2015 | Ellis et al. | |
| 8,969,038 B2* | 3/2015 | Ellis ..................... | C07K 14/245 435/69.1 |
| 8,969,039 B2* | 3/2015 | Ellis ..................... | C07K 14/245 435/69.1 |
| 9,109,216 B2 | 8/2015 | Ellis et al. | |
| 9,315,770 B2 | 4/2016 | Ellis et al. | |
| 9,493,558 B2 | 11/2016 | Ellis et al. | |
| 9,493,559 B2* | 11/2016 | Ellis ..................... | C12N 1/20 |
| 9,550,973 B2 | 1/2017 | Ellis et al. | |
| 9,587,227 B2* | 3/2017 | Ellis ..................... | C07K 14/245 |
| 9,725,516 B2* | 8/2017 | Ellis ..................... | C07K 16/2875 |
| 9,951,365 B2* | 4/2018 | Bassett .................. | C12N 15/70 |
| 9,957,328 B2* | 5/2018 | Ellis ..................... | C07K 16/2875 |
| 2005/0048572 A1* | 3/2005 | Reilly ................. | C07K 16/4291 435/7.1 |
| 2006/0204493 A1 | 9/2006 | Huang et al. | |
| 2009/0252743 A1 | 10/2009 | Heavner et al. | |
| 2010/0104573 A1 | 4/2010 | Burkly et al. | |

(Continued)

FOREIGN PATENT DOCUMENTS

| | | |
|---|---|---|
| CN | 1549821 A | 11/2004 |
| EA | 007905 | 2/2007 |

(Continued)

OTHER PUBLICATIONS

Getman et al. (2005) Pharmacokinetic Effects of 4C9, an Anti-FcRn Antibody, in Rats: Implications for the use of FcRn Inhibitors for the Treatment of Humoral Autoimmune and Alloimmune Conditions. Journal of Pharmaceutical Sciences, 94(4):718-729 (Year: 2005).*
Kim et al. (2010) Production of biohydrogen by recombinant expression of [NiFe]-hydrogenase 1 in *Escherichia coli*. Microbial Cell Factories, 9:54, pp. 1-10 (Year: 2010).*
Published Sequence Listing for Ellis (WO 2011/086138), published Jul. 21, 2011, 43 pages. (Year: 2011).*
Alberts, et al. "Molecular Biology of the Cell, Fifth Edition". New York:Garland Science, 2008. p. 367 (Year: 2008).*
Kolaj, O. et al. "Use of folding modulators to improve heterologous protein production in *Escherichia coli*" Microbial Cell Factories, 2009, pp. 1-18, vol. 8, No. 9.
McGraw-Hill, Dictionary of Bioscience, Nov. 12, 1998, pp. 1-3.

(Continued)

*Primary Examiner* — Neil P Hammell
(74) *Attorney, Agent, or Firm* — Saliwanchik, Lloyd & Eisenschenk

(57) ABSTRACT

The present disclosure relates to a recombinant gram-negative bacterial cell comprising: a) a mutant spr gene encoding a spr protein having a mutation at one or more amino acids selected from D133, H145, H157, N31, R62, I70, Q73, C94, S95, V98, Q99, R100, L108, Y115, V135, L136, G140, R144 and G147 and b) a gene capable of expressing or overexpressing one or more proteins capable of facilitating protein folding, such as FkpA, Skp, SurA, PPiA and PPiD, wherein the cell has reduced Tsp protein activity compared to a wild-type cell, methods employing the cells, use of the cells in the expression of proteins in particular antibodies, such as anti FcRn antibodies and proteins made by the methods described herein.

20 Claims, 24 Drawing Sheets

Specification includes a Sequence Listing.

(56) References Cited

U.S. PATENT DOCUMENTS

| | | | |
|---|---|---|---|
| 2011/0111408 | A1 | 5/2011 | Marrichi et al. |
| 2012/0258492 | A1 | 10/2012 | Ellis et al. |
| 2012/0288894 | A1 | 11/2012 | Ellis et al. |
| 2012/0295309 | A1 | 11/2012 | Ellis et al. |
| 2012/0301920 | A1 | 11/2012 | Ellis et al. |
| 2013/0045219 | A1 | 2/2013 | Burkly et al. |
| 2013/0060009 | A1 | 3/2013 | Bilgischer et al. |
| 2013/0178607 | A1 | 7/2013 | Wild |
| 2014/0141468 | A1 | 5/2014 | Ellis et al. |
| 2014/0302016 | A1 | 10/2014 | Burkly et al. |
| 2015/0132828 | A1 | 5/2015 | Ellis et al. |
| 2015/0166651 | A1 | 6/2015 | Ellis et al. |
| 2015/0166652 | A1 | 6/2015 | Ellis et al. |
| 2015/0344840 | A1 | 12/2015 | Ellis et al. |

FOREIGN PATENT DOCUMENTS

| | | | |
|---|---|---|---|
| EP | 2 546 267 | 1/2013 | |
| WO | WO 98/56930 | 12/1998 | |
| WO | WO 01/68860 | 9/2001 | |
| WO | WO 02/18445 | 3/2002 | |
| WO | WO 02/18446 | 3/2002 | |
| WO | WO 02/048376 | 6/2002 | |
| WO | WO 02/061090 | 8/2002 | |
| WO | WO 03/018771 | 3/2003 | |
| WO | WO 03/031475 | 4/2003 | |
| WO | WO 03/48306 | 6/2003 | |
| WO | WO 2003/048208 | 6/2003 | |
| WO | WO 2004/003019 | 1/2004 | |
| WO | WO 2004/051268 | 6/2004 | |
| WO | WO 2004/072116 | 8/2004 | |
| WO | WO 2005/003175 | 1/2005 | |
| WO | WO 2005/011376 | 2/2005 | |
| WO | WO 2005/035572 | 4/2005 | |
| WO | WO 2006/030220 | 3/2006 | |
| WO | WO 2006/033702 | 3/2006 | |
| WO | WO 2006/054063 | 5/2006 | |
| WO | WO-2006078273 A2 * | 7/2006 | ............ C12N 15/62 |
| WO | WO 2008/118356 | 10/2008 | |
| WO | WO 2011/036454 | 3/2011 | |
| WO | WO 2011/057120 | 5/2011 | |
| WO | WO 2011/086136 | 7/2011 | |
| WO | WO 2011/086138 | 7/2011 | |
| WO | WO 2011/086139 | 7/2011 | |
| WO | WO 2011/086141 | 7/2011 | |
| WO | WO-2011086138 A1 * | 7/2011 | ............ C12P 21/02 |
| WO | WO 2011/095506 | 8/2011 | |
| WO | WO 2012/013930 | 2/2012 | |
| WO | WO 2013/007388 | 1/2013 | |

OTHER PUBLICATIONS

Arbabi-Ghahroudi, M., et al., "Prokaryotic expression of antibodies," *Cancer and Metastasis Reviews*, Dec. 1, 2005, vol. 24, No. 4, pp. 501-519.
Chen, C., et al., "High-Level Accumulation of a Recombinant Antibody Fragment in the Periplasm of *Escherichia coli* Requires a Triple-Mutant (degP prc spr) Host Strain," *Biotechnology and Bioengineering*, Mar. 5, 2004, vol. 85, No. 5, pp. 463-474.
Georgiou, G., et al., "Preparative expression of secreted proteins in bacteria: status report and future prospects," *Current Opinion in Biotechnology*, Oct. 1, 2005, vol. 16, No. 5, pp. 538-545.
Written Opinion in International Application No. PCT/EP2013/059803, dated Aug. 14, 2013, pp. 1-5.
Pan, K.-L. et al. "Roles of DegP in Prevention of Protein Misfolding in the Periplasm upon Overexpression of Penicillin Acylase in *Escherichia coli*" *Journal of Bacteriology*, May 2003, pp. 3020-3030, vol. 185, No. 10.
Silber, K. R. et al. "Deletion of the pre (tsp) gene provides evidence for additional tail-specific proteolytic activity in *Escherichia coli* K-12" *Mol Gen Genet*, 1994, vol. 242, pp. 237-240.

Database UniProt [Online] EBI Accession No. UNIPROT:B7UFJ2, Subname: Full=Predicted peptidase, outer membrane lipoprotein, Feb. 10, 2009, XP-002630316, p. 1.
Database UniProt [Online] EBI Accession No. UNIPROT:B7LAJ9, Subname: Full=Putative peptidase, outer membrane lipoprotein, Feb. 10, 2009, XP-002630317, p. 1.
Database UniProt [Online] EBI Accession No. UNIPROT:B7LJR7, Subname: Full=Putative peptidase, outer membrane lipoprotein, Feb. 10, 2009, XP-002630318, p. 1.
Database UniProt [Online] EBI Accession No. UNIPROT:C1M6L5, Subname: Full=Putative uncharacterized protein, May 26, 2009, XP-002630319, p. 1.
Hara, H. et al. "Overproduction of Penicillin-Binding Protein 7 Suppresses Thermosensitive Growth Defect at Low Osmolarity due to an spr Mutation of *Escherichia coli*" *Microbial Drug Resistance*, Jan. 1, 1996, pp. 67-72, vol. 2, No. 1.
Aramini, J. et al. "Solution NMR Structure of the NlpC/P60 Domain of Lipoprotein Spr from *Escherichia coli*: Structural Evidence for a Novel Cysteine Peptidase Catalytic Triad" *Biochemistry*, 2008, pp. 9715-9717, vol. 47.
Tadokoro, A. et al. "Interaction of the *Escherichia coli* Lipoprotein NlpI with Periplasmic Prc (Tsp) Protease" *Journal of Biochemistry*, 2004, pp. 185-191, vol. 135.
Written Opinion in International Application No. PCT/EP2011/050415, dated Jun. 20, 2011, pp. 1-15.
Hu, X. et al. "Optimisation of production of a domoic acid-binding scFv antibody fragment in *Escherichia coli* using molecular chaperones and functional immobilisation on a mesoporous silicate support" *Protein Expression and Purification*, 2007, pp. 194-201, vol. 52.
O'Dwyer, R. et al. "Microarray-based analysis of recombinant protein production in *E. coli*" *Microbial Cell Factories*, 2006, pp. 1-2, vol. 5, Supp 1.
Maskos, K. et al. "DsbA and DsbC-catalyzed Oxidative Folding of Proteins with Complex Disulfide Bridge Patterns In Vitro and In Vivo" *Journal of Molecular Biology*, 2003, pp. 495-513, vol. 325.
Written Opinion in International Application No. PCT/EP2011/050416, dated Apr. 26, 2011, pp. 1-7.
Written Opinion in International Application No. PCT/EP2011/050413, dated Apr. 8, 2011, pp. 1-7.
Baba, T. et al. "Construction of *Escherichia coli* K-12 in-frame, single-gene knockout mutants: the Keio collection" *Molecular Systems Biology*, 2006, pp. 1-11.
Baneyx, F. et al. "Construction and Characterization of *Escherichia coli* Strains Deficient in Multiple Secreted Proteases: Protease III Degrades High-Molecular-Weight Substrates In Vivo" *Journal of Bacteriology*, Apr. 1991, pp. 2696-2703, vol. 173, No. 8.
Spiess, C. et al. "A Temperature-Dependent Switch from Chaperone to Protease in a Widely Conserved Heat Shock Protein" *Cell*, Apr. 30, 1999, p. 339-347, vol. 97.
Skorko-Glonek, J. et al. "The proteolytic activity of the HtrA (DegP) protein from *Escherichia coli* at low temperatures" *Microbiology*, 2008, pp. 3649-3658, vol. 154.
Meerman, H. J. et al. "Construction and Characterization of a Set of *E. coli* Strains Deficient in All Known Loci Affecting the Proteolytic Stability of Secreted Recombinant Proteins" *Bio/Technology*, Nov. 1994, pp. 1107-1110, vol. 12.
Written Opinion in International Application No. PCT/GB2010/001790, dated Feb. 3, 2011, pp. 1-9.
Skorko-Glonek, J. et al. "Site-directed mutagenesis of the HtrA(DegP) serine protease, whose proteolytic activity is indispensable for *Escherichia coli* survival at elevated temperatures" *Gene*, 1995, vol. 163, pp. 47-52.
Pending claims from U.S. Appl. No. 14/633,294, 2015, pp. 1-4.
Pending claims from U.S. Appl. No. 14/600,089, 2015, pp. 1-6.
Pending claims from U.S. Appl. No. 14/633,257, 2015, pp. 1-4.
Ponniah, K. et al. "The production of soluble and correctly folded recombinant bovine β-lactoglobulin variants A and B in *Escherichia coli* for NMR studies," *Protein Expression and Purification*, 2010, vol. 70, No. 2, pp. 283-289.
Liu, Z. et al., "The Influence of Coexpression of TrxA and DsbC to the Expression of Heterogenous Protein with Multiple Disulfide Bonds" *Chinese Journal of Biochemistry and Molecular Biology*, Aug. 30, 2002, pp. 486-489, vol. 18, No. 4.

(56) References Cited

OTHER PUBLICATIONS

Want, A. et al. "Studies Related to Antibody Fragment (Fab) Production in Escherichia coli W3110 Fed-Batch Fermentation Processes Using Multiparameter Flow Cytometry" *Cytometry Part A*, Feb. 2009, pp. 148-154, vol. 75, No. 2.

Hu, X. et al. "Cloning, expression and characterisation of a single-chain Fv antibody fragment against domoic acid in Escherichia coli" *Journal of Biotechnology*, 2005, pp. 38-45, vol. 120.

Gehring, C. K. et al. "Functional and nutritional characteristics of proteins and lipids recovered by isoelectric processing offish by-products and low-value fish: A review" *Food Chemistry*, 2011, pp. 422-431, vol. 124.

Wunderlich, M. et al. "Bacterial Protein Disulfide Isomerase: Efficient Catalysis of Oxidative Protein Folding at Acidic pH" *Biochemistry*, 1993, p. 12251-12256, vol. 32.

Written Opinion in International Application No. PCT/EP2012/002945, dated Oct. 24, 2012, pp. 1-9.

Casset, F. et al. "A peptide mimetic of an anti-CD4 monoclonal antibody by rational design" *Biochemical and Biophysical Research Communications*, 2003, pp. 198-205, vol. 307.

Smith-Gill, S. J. et al. "Contributions of Immunoglobulin Heavy and Light Chains to Antibody Specificity for Lysozyme and Two Haptens" *Journal of Immunology*, Dec. 15, 1987, pp. 4135-4144, vol. 139.

Song, M.-K. et al. "Light Chain of Natural Antibody Plays a Dominant Role in Protein Antigen Binding" *Biochemical and Biophysical Research Communications*, 2000, pp. 390-394, vol. 268.

Chen, Y. et al. "Selection and Analysis of an Optimized Anti-VEGF Antibody: Crystal Structure of an Affinity-matured Fab in Complex with Antigen" *J. Mol. Biol.*, 1999, pp. 865-881, vol. 293.

Ward, E. et al. "Binding activities of a repertoire of single immunoglobulin variable domains secreted from Escherichia coli" *Nature*, Oct. 12, 1989, pp. 544-546, vol. 341.

Kobayashi, H. et al. "Tryptophan H33 plays an important role in pyrimidine (6-4) pyrimidone photoproduct binding by a high-affinity antibody" *Protein Engineering*, 1999, pp. 879-884, vol. 12, No. 10.

Kumar, S. et al. "Molecular Cloning and Expression of the Fabs of Human Autoantibodies in Escherichia coli" *Journal of Biological Chemistry*, Nov. 10, 2000, pp. 35129-35136, vol. 275, No. 45.

MacCallum, R. M. et al. "Antibody-antigen Interactions: Contact Analysis and Binding Site Topography" *J. Mol. Biol.*, 1998, pp. 732-745, vol. 262.

Vajdos, F. F. et al. "Comprehensive Functional Maps of the Antigen-binding Site of an Anti-ErbB2 Antibody Obtained with Shotgun Scanning Mutagenesis" *J. Mol. Biol.*, 2002, pp. 415-428, vol. 320.

Colman, P. M. "Effects of amino acid sequence changes on antibody-antigen interactions" *Research in Immunology*, 1994, pp. 33-36, vol. 145.

Holm, P. et al. "Functional mapping and single chain construction of the anti-cytokeratin 8 monoclonal antibody TS1" *Molecular Immunology*, 2007, pp. 1075-1084, vol. 44.

Jang, Y.-J. et al. "The structural basis for DNA binding by an anti-DNA autoantibody" *Molecular Immunology*, 1998, pp. 1207-1217, vol. 35.

Wu, H. et al. "Humanization of a Murine Monoclonal Antibody by Simultaneous Optimization of Framework and CDR Residues" *J. Mol. Biol.*, 1999, pp. 151-162, vol. 294.

De Pascalis, R. et al. "Grafting of "Abbreviated" Complementarity-Determining Regions Containing Specificity-Determining Residues Essential for Ligand Contact to Engineer a Less Immunogenic Humanized Monoclonal Antibody" *Journal of Immunology*, 2002, pp. 3076-3084, vol. 169.

Burks, E. A. et al. "In vitro scanning saturation mutagenesis of an antibody binding pocket" *Proc. Natl. Acad. Sci. USA*, Jan. 1997, pp. 412-417, vol. 94.

Brummell, D. A. et al. "Probing the combining site of an anti-carbohydrate antibody by saturation-mutagenesis: role of the heavy-chain CDR3 residues" *Biochemistry*, Feb. 2, 1993, pp. 1180-1187, vol. 32, No. 4.

Brorson, K. et al. "Mutational Analysis of Avidity and Fine Specificity of Anti-Levan Antibodies" *Journal of Immunology*, 1999, pp. 6694-6701, vol. 163.

Rudikoff, S. et al. "Single amino acid substitution altering antigen-binding specificity" *Proc. Natl. Acad. Sci. USA*, Mar. 1982, pp. 1979-1983, vol. 79.

Brams, P. et al. "A humanized anti-human CD154 monoclonal antibody blocks CD154-CD40 mediated human B cell activation" *International Immunopharmacology*, 2001, pp. 277-294, vol. 1.

Boumpas, D. T. et al. "A Short Course of BG9588 (Anti-CD40 Ligand Antibody) Improves Serologic Activity and Decreases Hematuria in Patients With Proliferative Lupus Glomerulonephritis" *Arthritis & Rheumatism*, Mar. 2003, vol. 48, No. 3, pp. 719-727.

Durie, F.H. et al. "Prevention of Collagen-Induced Arthritis with an Antibody to gp39, the Ligand for CD40" *Science*, Sep. 3, 1993, vol. 261, pp. 1328-1330.

Ferrant, J. L. et al. "The contribution of Fc effector mechanisms in the efficacy of anti-CD154 immunotherapy depends on the nature of the immune challenge" *International Immunology*, Oct. 5, 2004, vol. 16, No. 11, pp. 1583-1594.

Kuwana, M. et al. "Effect of a single injection of humanized anti-CD154 monoclonal antibody on the platelet-specific autoimmune response in patients with immune thrombocytopenic purpura" *Blood*, Feb. 15, 2004, vol. 103, No. 4, pp. 1229-1236.

Quezada, S. A. et al. "Distinct Mechanisms of Action of Anti-CD154 in Early Versus Late Treatment of Murine Lupus Nephritis" *Arthritis & Rheumatism*, Sep. 2003, vol. 48, No. 9, pp. 2541-2554.

Kalled, S. L. et al. "Apoptosis and Altered Dendritic Cell Homeostasis in Lupus Nephritis Are Limited by Anti-CD154 Treatment" *The Journal of Immunology*, 2001, pp. 1740-1747, vol. 167.

Cordeiro, A. C. et al. "Novel Therapies in Lupus—Focus on Nephritis" *Acta Reumatol Port.* 2008, pp. 157-169, vol. 33, No. 2.

Toubi, E. et al. "The Role of CD40-CD 154 Interactions in Auto-immunity and the Benefit of Disrupting this Pathway" *Immunity*, 2004, pp. 457-464, vol. 37, Nos. 6-7. Abstract Only.

Peters, A. et al. "CD40 and Autoimmunity: The Dark Side of a Great Activator" *Semin Immunol.*, Oct. 2009, pp. 293-300, vol. 21, No. 5.

Getman K. E. et al. "Pharmacokinetic effects of 4C9, an anti-FcRn antibody, in rats: Implications for the use of FcRn inhibitors for the treatment of humoral autoimmune and alloimmune conditions" *Journal of Pharmaceutical Sciences*, Apr. 2005, pp. 718-729, vol. 94, No. 4.

Ow, D. S.-W. et al. "Co-expression of Skp and KfpA chaperones improves cell viability and alters the global expression of stress response genes during scFvD1.3 production" *Microbial Cell Factories*, 2010, pp. 1-14, vol. 9, No. 22.

\* cited by examiner

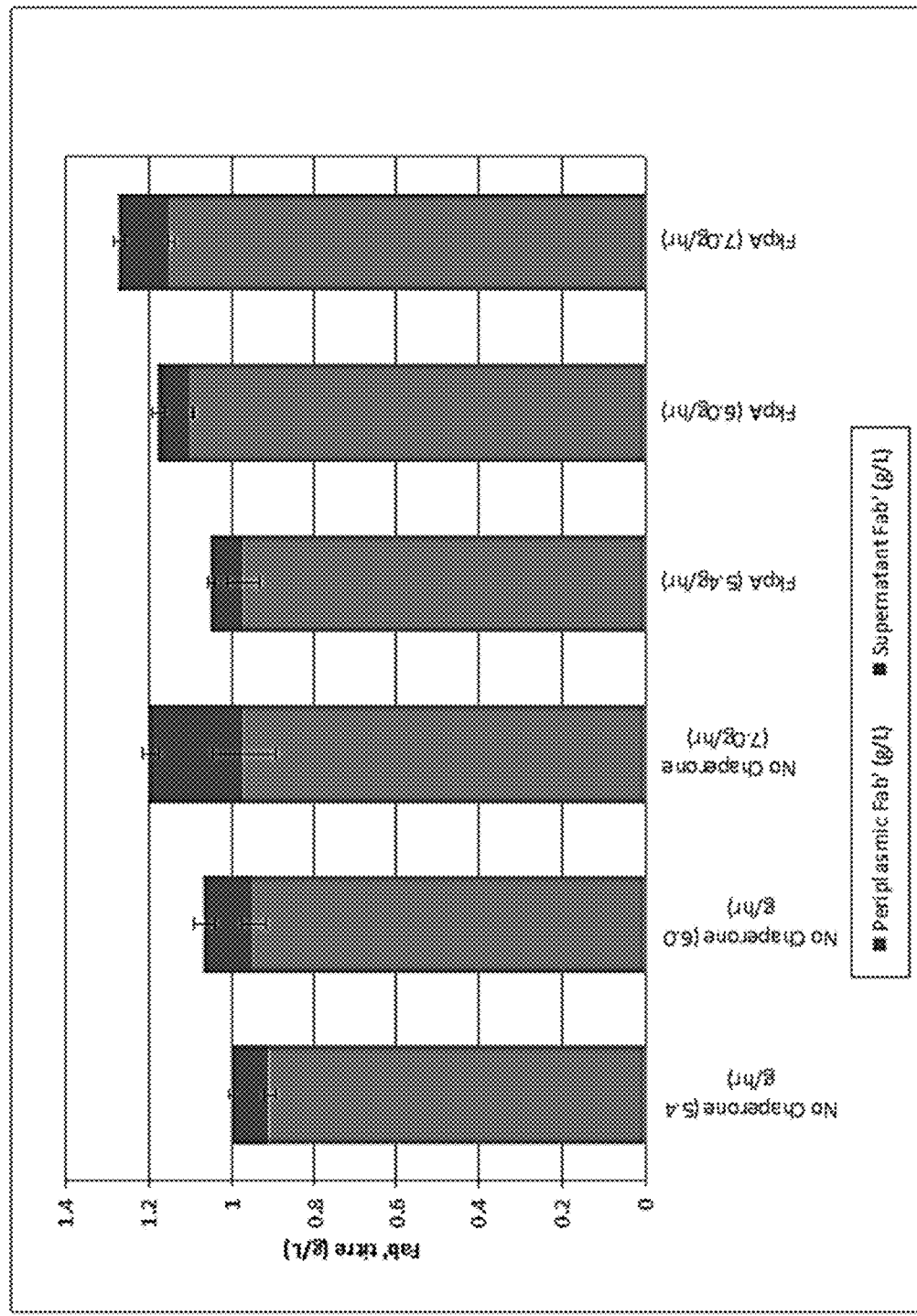
FIG. 2 Feed Rate Variation Experiments

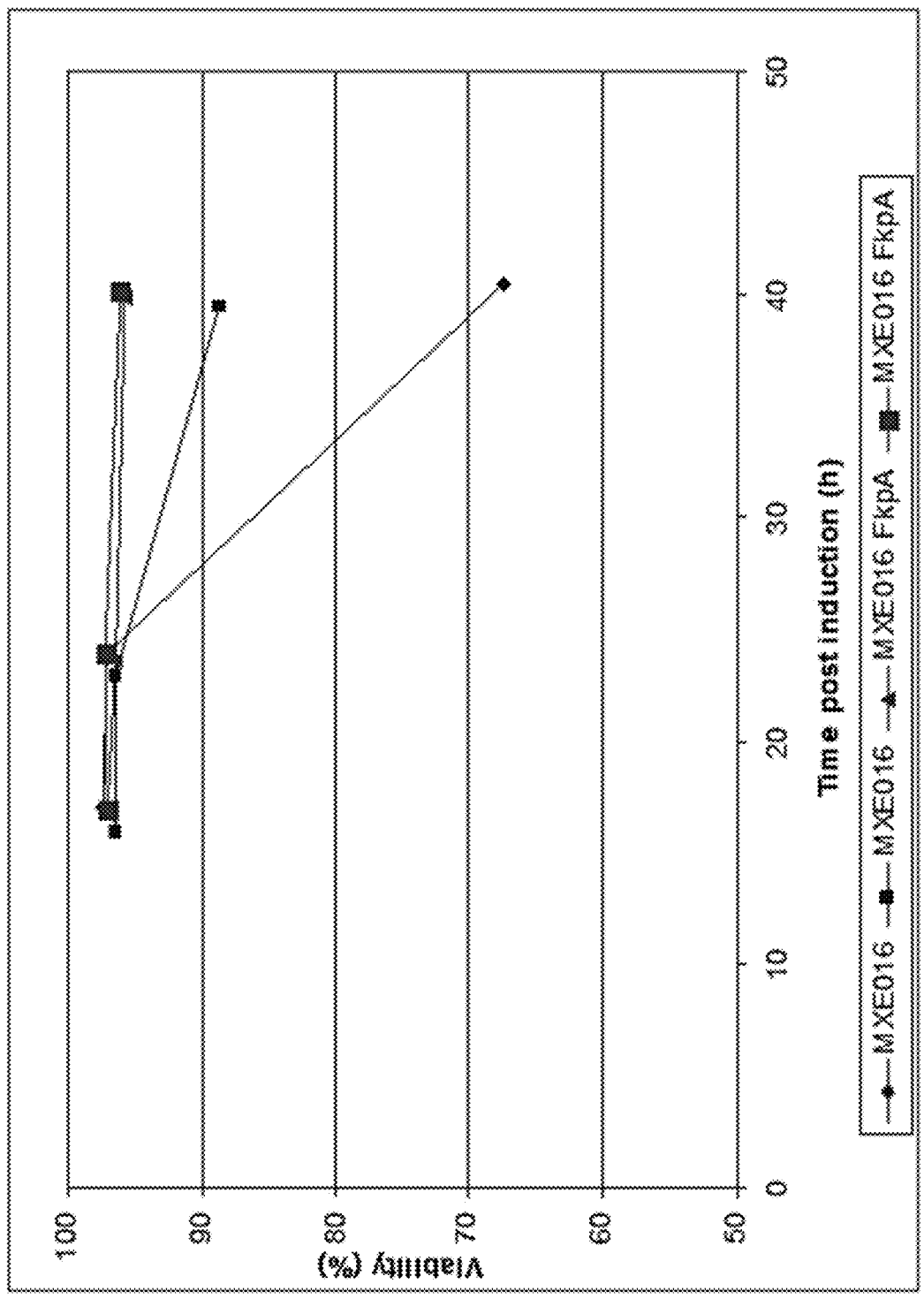
FIG. 3A  Cell Viability

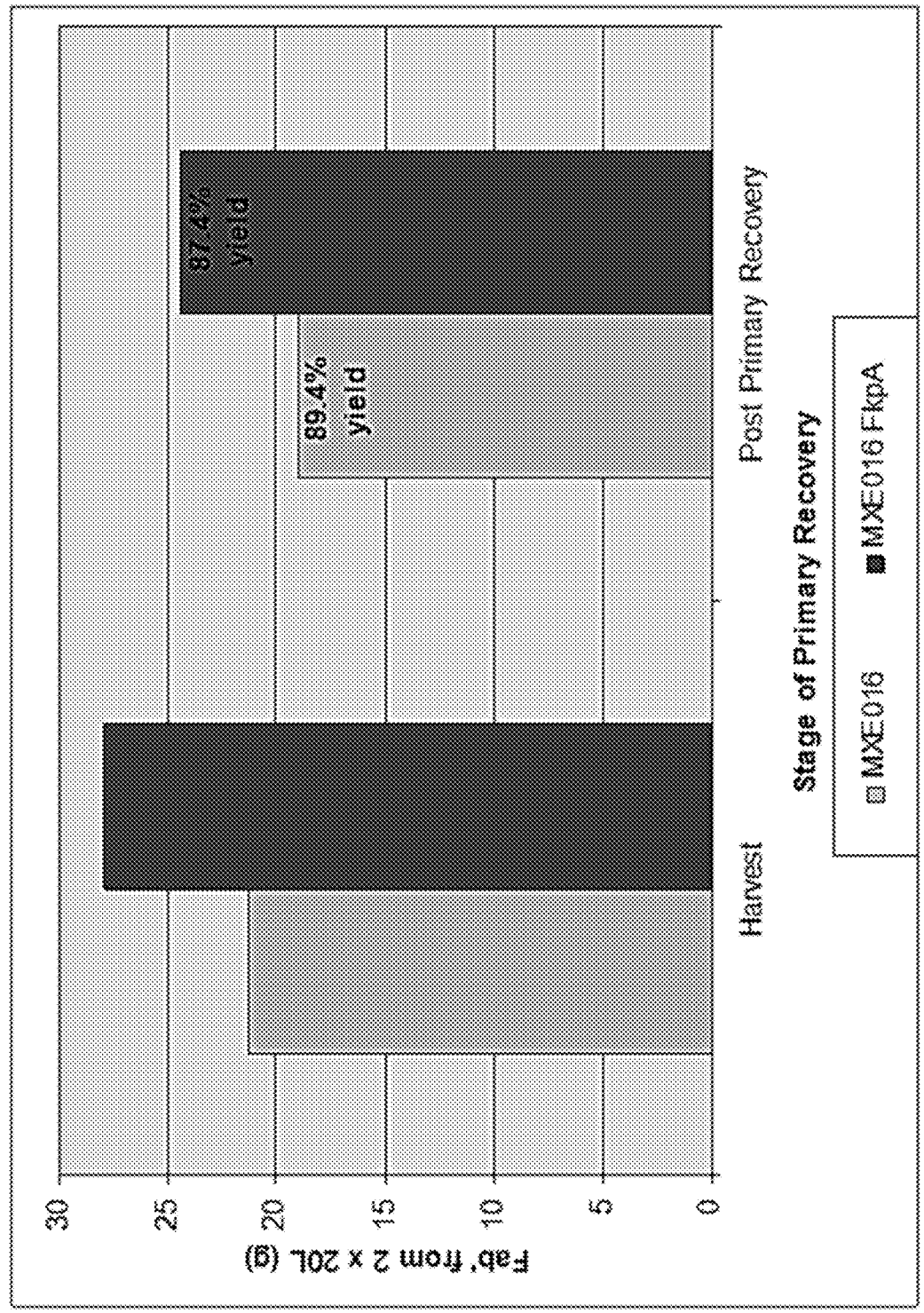
FIG. 4 Harvest from 20 Litre Pilot Scale Productions and Primary Recovery for "MXE016" Cell Lines

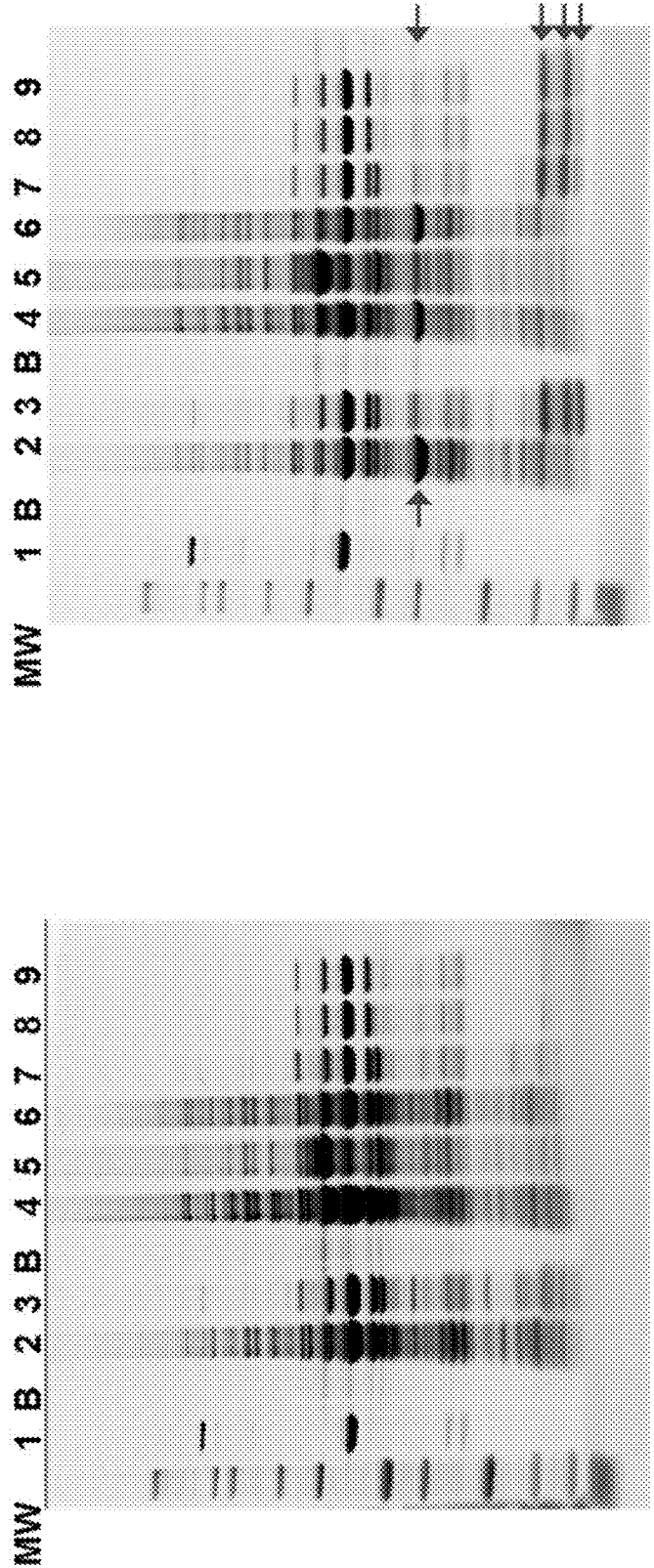

FIG. 6 Western Blot Under Non-Reducing Conditions for a 20 L Pilot Scale Batch
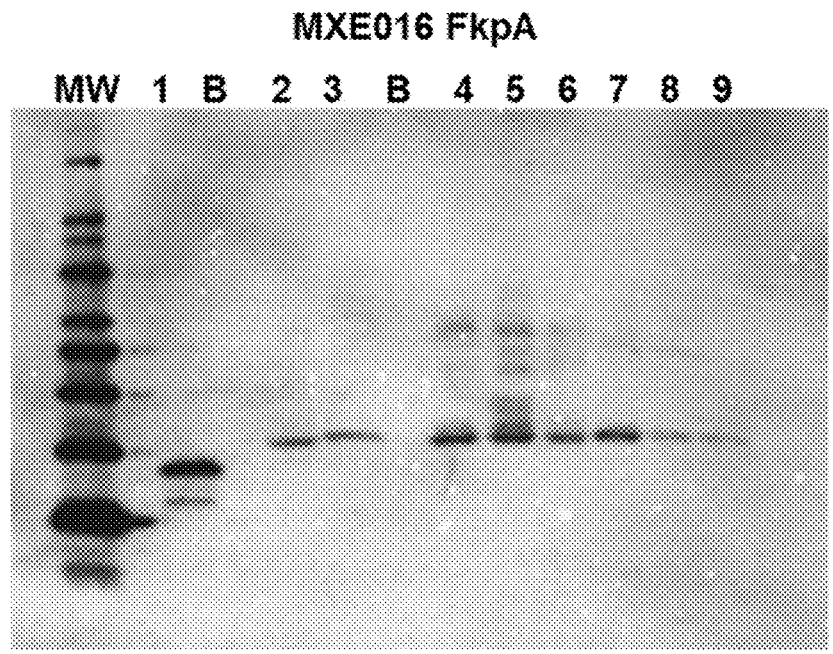
1 – His-tag positive control (DsbC)
2 – 30°C small scale extract
3 – 60°C small scale extract
4 – Supernatant of heavy phase
5 – Light phase
6 – Post buffer addition
7 – Post extraction
8 – Post extract centrifugation
9 – Post filtration

FIG. 7A     Mutation in Various Genes

Wild type ptr (protease III) 5'

```
     *   M   P   R   S   T   W   F   K   A   L   L   L   V
    TGA ATG CCC CGC AGC ACC TGG TTC AAA GCA TTA TTG TTG TTA GTT

A   L   W   A   P   L   S    (SEQ ID NO: 81)
    GCC CTT TGG GCA CCC TTA AGT   (SEQ ID NO: 82)
```

Mutated Δ ptr (protease III) 5'

```
        EcoR I
       ~~~~~~~~
     *   I   P   R   S   T   W   F   K   A   L   L   L   V
    TGA ATT CCC CGC AGC ACC TGG TTC AAA GCA TTA TTG TTG TTA GTT

Ase I
                       ~~~~~~~~
     A   L   W   A   H   *   C    (SEQ ID NO: 79)
    GCC CTT TGG GCA CAT TAA TGT   (SEQ ID NO: 80)
```

FIG. 7B

Wild type Tsp 5'

```
         M   N   M   F   F   R   L   T   A   L   A   G   L   L   A
        ATG AAC ATG TTT TTT AGG CTT ACC GCG TTA GCT GGC CTG CTT GCA

I   A   G   Q   T   F   A    (SEQ ID NO: 75)
        ATA GCA GGC CAG ACC TTC GCT   (SEQ ID NO: 76)
```

Mutated Δ Tsp 5'

```
        EcoR I
       ~~~~~~~~
         M   N   S   F   L   G   L   P   R   *   L   A   C   L   Q
        ATG AAT TCG TTT TTA GGC TTA CCG CGT TAG CTG GCC TGC TTG CAA

Ase I
                          ~~~~~~~~
         *   Q   A   R   H   *   L    (SEQ ID NO: 77)
        TAG CAG GCC AGA CAT TAA TTG   (SEQ ID NO: 78)
```

FIG. 7C
Wild type DegP
```
202   D    A    A    I    N    R    G    N    S    G    G    (SEQ ID NO: 83)
949   GAT  GCA  GCG  ATC  AAC  CGT  GGT  AAC  TCC  GGT  GGT  (SEQ ID NO: 84)
```
Mutated DegP S210A
```
                       Ase I
                      ~~~~~~~~
202   D    A    A    I    N    R    G    N    A    G    G    (SEQ ID NO: 85)
949   GAT  GCA  GCG  ATT  AAT  CGT  GGT  AAC  GCC  GGT  GGT  (SEQ ID NO: 86)
```
FIG. 7D Gene Insertion
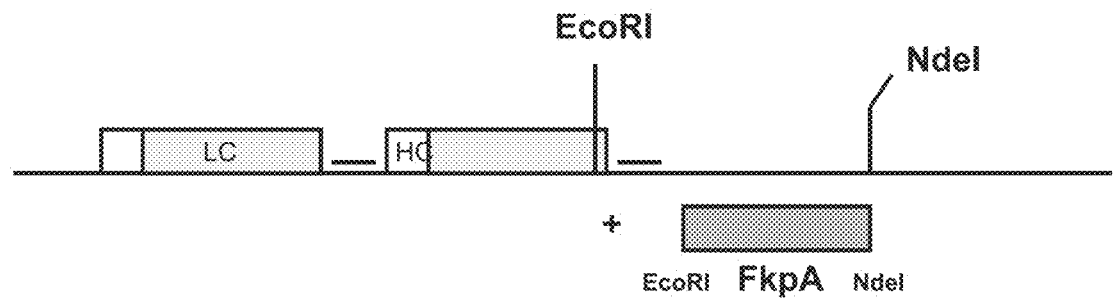
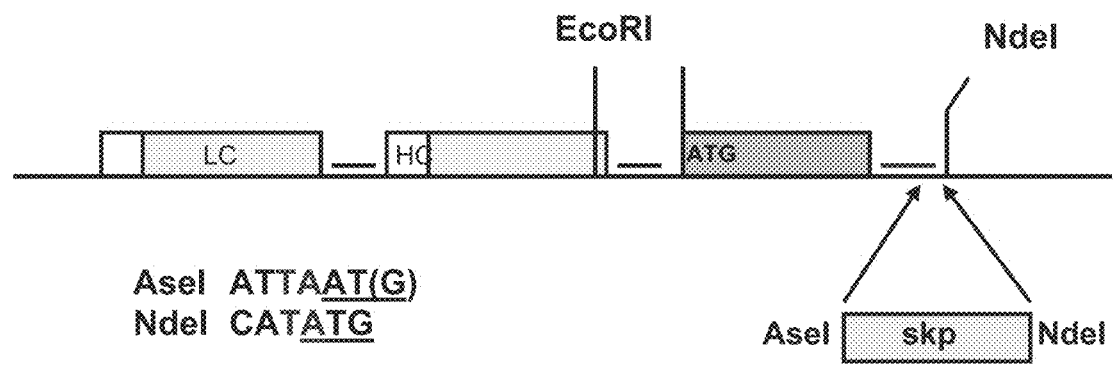
AseI ATTAAT(G)
NdeI CATATG

FIG. 8A   SEQ ID NO:1 is the DNA sequence of the wild-type Tsp gene including the 6 nucleotides ATGAAC upstream of the start codon.

```
ATGAACATGTTTTTTAGGCTTACCGCGTTAGCTGGCCTGCTTGCAATAGCAGGCCAGACCTTCGCTGTAGA
AGATATCACGCGTGCTGATCAAATTCCGGTATTAAAGGAAGAGACGCAGCATGCGACGGTAAGTGAGCGCG
TAACGTCGCGCTTCACCCGTTCTCATTATCGCCAGTTCGACCTCGATCAGGCATTTTCGGCCAAAATCTTT
GACCGCTACCTGAATCTGCTCGATTACAGCCACAACGTGCTGCTGGCAAGCGATGTTGAACAGTTCGCGAA
AAAGAAAACCGAGTTAGGCGATGAACTGCGTTCAGGCAAACTCGACGTTTTCTACGATCTCTACAATCTGG
CGCAAAAGCGCCGTTTTGAGCGTTACCAGTACGCTTTGTCGGTACTGGAAAAGCCGATGGATTTCACCGGC
AACGACACTTATAACCTTGACCGCAGCAAAGCGCCCTGGCCGAAAAACGAGGCTGAGTTGAACGCGCTGTG
GGACAGTAAAGTCAAATTCGACGAGTTAAGCCTGAAGCTGACAGGAAAAACGGATAAAGAAATTCGTGAAA
CCCTGACTCGCCGCTACAAATTTGCCATTCGTCGTCTGGCGCAAACCAACAGCGAAGATGTTTCTCGCTG
GCAATGACGGCGTTTGCGCGTGAAATCGACCCGCATACCAACTATCTTTCCCCGCGTAATACCGAACAGTT
CAACACTGAAATGAGTTTGTCGCTGGAAGGTATTGGCGCAGTGCTGCAAATGGATGATGACTACACCGTTA
TCAATTCGATGGTGGCAGGTGGTCCGGCAGCGAAGAGTAAAGCTATCAGCGTTGGTGACAAAATTGTCGGT
GTTGGTCAAACAGGCAAGCCGATGGTTGACGTGATTGGCTGGCGTCTTGATGATGTGGTTGCCTTAATTAA
AGGGCCGAAGGGCAGTAAAGTTCGTCTGGAAATTTTACCTGCTGGTAAAGGGACCAAGACCCGTACTGTAA
CGTTGACCCGTGAACGTATTCGTCTCGAAGACCGCGCGGTTAAAATGTCGGTGAAGACCGTCGGTAAGAG
AAAGTCGGCGTGCTGGATATTCCGGGCTTCTATGTGGGTTTGACAGACGATGTCAAAGTGCAACTGCAGAA
ACTGGAAAAACAGAATGTCAGCAGCGTCATCATCGACCTGCGTAGCAATGGCGGTGGGCGTTAACTGAAG
CCGTATCGCTCTCCGGTCTGTTTATTCCTGCGGGTCCCATTGTTCAGGTCCGCGATAACAACGGCAAGGTT
CGTGAAGATAGCGATACCGACGGACAGGTTTTCTATAAAGGCCCGCTGGTGGTGCTGGTTGACCGCTTCAG
TGCTTCGGCTTCAGAAATCTTTGCCGCGGCAATGCAGGATTACGGTCGTGCGCTGGTTGTGGGTGAACCGA
CGTTTGGTAAAGGCACCGTTCAGCAATACCGTTCATTGAACCGTATTTACGATCAGATGTTACGTCCTGAA
TGGCCAGCGCTGGGTTCTGTGCAGTACACGATCCAGAAATTCTATCGCGTTAACGGCGGCAGTACGCAACG
TAAAGGCGTAACGCCAGACATCATCATGCCGACGGGTAATGAGAAACGGAAACGGGTGAGAAATTCGAAG
ATAACGCGCTGCCGTGGGATAGCATTGATGCCGCGACTTATGTGAAATCAGGAGATTTAACGGCCTTTGAA
CCGGAGCTGCTGAAGGAACATAATGCGCGTATCGCGAAAGATCCTGAGTTCCAGAACATCATGAAGGATAT
CGCGCGCTTCAACGCTATGAAGGACAAGCGCAATATCGTTTCTCTGAATTACGCTGTGCGTGAGAAAGAGA
ATAATGAAGATGATGCGACGCGTCTGGCGCGTTTGAACGAACGCTTTAAACGCGAAGGTAAACCGGAGTTG
AAGAAACTGGATGATCTACCGAAAGATTACCAGGAGCCGGATCCTTATCTGGATGAGACGGTGAATATCGC
ACTCGATCTGGCGAAGCTTGAAAAAGCCAGACCCGCGGAACAACCCGCTCCCGTCAAGTAA
```

FIG. 8B   SEQ ID NO:2 is the amino acid sequence of the wild-type Tsp protein.

```
MFFRLTALAGLLAIAGQTFAVEDITRADQIPVLKEETQHATVSERVTSRFTRSHYRQFDLDQAFSAKIFDR
YLNLLDYSHNVLLASDVEQFAKKKTELGDELRSGKLDVFYDLYNLAQKRRFERYQYALSVLEKPMDFTGND
TYNLDRSKAPWPKNEAELNALWDSKVKFDELSLKLTGKTDKEIRETLTRRYKFAIRRLAQTNSEDVFSLAM
TAFAREIDPHTNYLSPRNTEQFNTEMSLSLEGIGAVLQMDDDYTVINSMVAGGPAAKSKAISVGDKIVGVG
QTGKPMVDVIGWRLDDVVALIKGPKGSKVRLEILPAGKGTKTRTVTLTRERIRLEDRAVKMSVKTVGKEKV
GVLDIPGFYVGLTDDVKVQLQKLEKQNVSSVIIDLRSNGGGALTEAVSLSGLFIPAGPIVQVRDNNGKVRE
DSDTDGQVFYKGPLVVLVDRFSASASEIFAAAMQDYGRALVVGEPTFGKGTVQQYRSLNRIYDQMLRPEWP
ALGSVQYTIQKFYRVNGGSTQRKGVTPDIIMPTGNEETETGEKFEDNALPWDSIDAATYVKSGDLTAFEPE
LLKEHNARIAKDPEFQNIMKDIARFNAMKDKRNIVSLNYAVREKENNEDDATRLARLNERFKREGKPELKK
LDDLPKDYQEPDPYLDETVNIALDLAKLEKARPAEQPAPVK*
```

FIG. 8C

SEQ ID NO:3 is the DNA sequence of a mutated knockout Tsp gene including the 6 nucleotides ATGAAT upstream of the start codon.

ATGAATTCGTTTTTAGGCTTACCGCGTTAGCTGGCCTGCTTGCAATAGCAGGCCAGACATTAATTGTAGAA
GATATCACGCGTGCTGATCAAATTCCGGTATTAAAGGAAGAGACGCAGCATGCGACGGTAAGTGAGCGCGT
AACGTCGCGCTTCACCCGTTCTCATTATCGCCAGTTCGACCTCGATCAGGCATTTTCGGCCAAAATCTTTG
ACCGCTACCTGAATCTGCTCGATTACAGCCACAACGTGCTGCTGGCAAGCGATGTTGAACAGTTCGCGAAA
AAGAAACCGAGTTAGGCGATGAACTGCGTTCAGGCAAACTCGACGTTTTCTACGATCTCTACAATCTGGC
GCAAAAGCGCCGTTTTGAGCGTTACCAGTACGCTTTGTCGGTACTGGAAAAGCCGATGGATTTCACCGGCA
ACGACACTTATAACCTTGACCGCAGCAAAGCGCCTGGCCGAAAAACGAGGCTGAGTTGAACGCGCTGTGG
GACAGTAAAGTCAAATTCGACGAGTTAAGCCTGAAGCTGACAGGAAAAACGGATAAAGAAATTCGTGAAAC
CCTGACTCGCCGCTACAAATTTGCCATTCGTCGTCTGGCGCAAACCAACAGCGAAGATGTTTTCTCGCTGG
CAATGACGGCGTTTGCGCGTGAAATCGACCCGCATACCAACTATCTTTCCCCGCGTAATACCGAACAGTTC
AACACTGAAATGAGTTTGTCGCTGGAAGGTATTGGCGCAGTGCTGCAAATGGATGATGACTACACCGTTAT
CAATTCGATGGTGGCAGGTGGTCCGGCAGCGAAGAGTAAAGCTATCAGCGTTGGTGACAAAATTGTCGGTG
TTGGTCAAACAGGCAAGCCGATGGTTGACGTGATTGGCTGGCGTCTTGATGATGTGGTTGCCTTAATTAAA
GGGCCGAAGGGCAGTAAAGTTCGTCTGGAAATTTTACCTGCTGGTAAAGGGACCAAGACCCGTACTGTAAC
GTTGACCCGTGAACGTATTCGTCTCGAAGACCGCGCGGTTAAAATGTCGGTGAAGACCGTCGGTAAAGAGA
AAGTCGGCGTGCTGGATATTCCGGGCTTCTATGTGGGTTTGACAGACGATGTCAAAGTGCAACTGCAGAAA
CTGGAAAAACAGAATGTCAGCAGCGTCATCATCGACCTGCGTAGCAATGGCGGTGGGGCGTTAACTGAAGC
CGTATCGCTCTCCGGTCTGTTTATTCCTGCGGGTCCCATTGTTCAGGTCCGCGATAACAACGGCAAGGTTC
GTGAAGATAGCGATACCGACGGACAGGTTTTCTATAAAGGCCCGCTGGTGGTGCTGGTTGACCGCTTCAGT
GCTTCGGCTTCAGAAATCTTTGCCGCGGCAATGCAGGATTACGGTCGTGCGCTGGTTGTGGGTGAACCGAC
GTTTGGTAAAGGCACCGTTCAGCAATACCGTTCATTGAACCGTATTTACGATCAGATGTTACGTCCTGAAT
GGCCAGCGCTGGGTTCTGTGC
AGTACACGATCCAGAAATTCTATCGCGTTAACGGCGGCAGTACGCAACGTAAAGGCGTAACGCCAGACATC
ATCATGCCGACGGGTAATGAAGAAACGGAAACGGGTGAGAAATTCGAAGATAACGCGCTGCCGTGGGATAG
CATTGATGCCGCGACTTATGTGAAATCAGGAGATTTAACGGCCTTTGAACCGGAGCTGCTGAAGGAACATA
ATGCGCGTATCGCGAAAGATCCTGAGTTCCAGAACATCATGAAGGATATCGCGCGCTTCAACGCTATGAAG
GACAAGCGCAATATCGTTTCTCTGAATTACGCTGTGCGTGAGAAAGAGAATAATGAAGATGATGCGACGCG
TCTGGCGCGTTTGAACGAACGCTTTAAACGCGAAGGTAAACCGGAGTTGAAGAAACTGGATGATCTACCGA
AAGATTACCAGGAGCCGGATCCTTATCTGGATGAGACGGTGAATATCGCACTCGATCTGGCGAAGCTTGAA
AAAGCCAGACCCGCGGAACAACCCGCTCCCGTCAAGTAA

SEQ ID NO:4 is the DNA sequence of the wild-type Protease III gene.

ATGCCCCGCAGCACCTGGTTCAAAGCATTATTGTTGTTAGTTGCCCTTTGGGCACCCTTAAGTCAGGCAGA
AACGGGATGGCAGCCGATTCAGGAAACCATCCGTAAAGTGATAAAGATAACCGCCAGTATCAGGCTATAC
GTCTGGATAACGGTATGGTGGTCTTGCTGGTTTCTGATCCGCAGGCAGTTAAATCGCTCTCGGCGCTGGTG
GTGCCCGTTGGGTCGCTGGAAGATCCCGAGGCGTACCAGGGGCTGGCACATTACCTTGAACATATGAGTCT
GATGGGGTCGAAAAAGTACCCGCAGGCTGACAGTCTGGCCGAATATCTCAAAATGCACGGCGGTAGTCACA
ATGCCAGCACTGCGCCGTATCGCACGGCTTTCTATCTGGAAGTTGAGAACGACGCCTTGCCTGGTGCGGTA
GACCGCCTGGCCGATGCTATTGCTGAACCTTTGCTCGACAAGAAATATGCCGAACGTGAGCGTAATGCGGT
GAACGCTGAATTAACCATGGCGCGTACGCGTGACGGGATGCGCATGGCACAGGTCAGCGCAGAAACCATTA
ACCCGGCACACCCCGGTTCAAAGTTTTCTGGTGGTAACCTCGAAACTTTAAGCGACAAACCTGGTAATCCG
GTGCAGCAGGCGCTGAAAGATTTCCACGAGAAGTACTATTCCGCCAATTTGATGAAGGCGGTTATTTACAG
TAATAAACCGCTGCCGGAGTTGGCAAAAATGGCGGCGGACACCTTTGGTCGCGTGCCGAACAAAGAGAGCA
AAAAACCGGAAATCACCGTGCCGGTAGTCACCGACGCGCAAAAGGGCATTATCATTCATTACGTCCCTGCG
CTGCCGCGTAAAGTGTTGCGCGTTGAGTTTCGCATCGATAACAACTCAGCGAAGTTCCGTAGTAAAACCGA
TGAATTGATTACCTATCTGATTGGCAATCGCAGCCCAGGTACACTTTCTGACTGGCTGCAAAAGCAGGGAT
TAGTTGAGGGCATTAGCGCCAACTCCGATCCTATCGTCAACGGCAACAGCGGCGTATTAGCGATCTCTGCG
TCTTTAACCGATAAAGGCCTGGCTAATCGCGATCAGGTTGTGGCGGCAATTTTTAGCTATCTCAATCTGTT
ACGTGAAAAAGGCATT

FIG. 8C (continued)

```
GATAAACAATACTTCGATGAACTGGCGAATGTGCTGGATATCGACTTCCGTTATCCGTCGATCACCCGTGA
TATGGATTACGTCGAATGGCTGGCAGATACCATGATTCGCGTTCCTGTTGAGCATACGCTGGATGCAGTCA
ATATTGCCGATCGGTACGATGCTAAAGCAGTAAAGGAACGTCTGGCGATGATGACGCCGCAGAATGCGCGT
ATCTGGTATATCAGCCCGAAAGAGCCGCACAACAAAACGGCTTACTTTGTCGATGCGCCGTATCAGGTCGA
TAAAATCAGCGCACAAACTTTCGCCGACTGGCAGAAAAAAGCCGCCGACATTGCGCTCTCTTTGCCAGAGC
TTAACCCTTATATTCCTGATGATTTCTCGCTGATTAAGTCAGAGAAGAAATACGACCATCCAGAGCTGATT
GTTGATGAGTCGAATCTGCGCGTGGTGTATGCGCCAAGCCGTTATTTTGCCAGCGAGCCCAAAGCTGATGT
CAGCCTGATTTTGCGTAATCCGAAAGCCATGGACAGCGCCCGCAATCAGGTGATGTTTGCGCTCAATGATT
ATCTCGCAGGGCTGGCGCTTGATCAGTTAAGCAACCAGGCGTCGGTTGGTGGCATAAGTTTTTCCACCAAC
GCTAACAACGGCCTTATGGTTAATGCTAATGGTTACACCCAGCGTCTGCCGCAGCTGTTCCAGGCATTGCT
CGAGGGGTACTTTAGCTATACCGCTACGGAAGATCAGCTTGAGCAGGCGAAGTCCTGGTATAACCAGATGA
TGGATTCCGCAGAAAAGGGTAAAGCGTTTGAGCAGGCGATTATGCCCGCGCAGATGCTCTCGCAAGTGCCG
TACTTCTCGCGAGATGAACGGCGTAAAATTTTGCCCTCCATTACGTTGAAAGAGGTGCTGGCCTATCGCGA
CGCCTTAAAATCAGGGGCTCGACCAGAGTTTATGGTTATCGGCAACATGACCGAGGCCCAGGCAACAACGC
TGGCACGCGATGTGCAAAAACAGTTGGGCGCTGATGGTTCAGAGTGGTGTCGAAACAAAGATGTAGTGGTC
GATAAAAAACAATCCGTCATCTTTGAAAAGCCGGTAACAGCACCGACTCCGCACTGGCAGCGGTATTTGT
ACCGACTGGCTACGATGAATACACCAGCTCAGCCTATAGCTCTCTGTTGGGGCAGATCGTACAGCCGTGGT
TCTACAATCAGTTGCGTACCGAAGAACAATTGGGCTATGCCGTGTTTGCGTTTCCAATGAGCGTGGGGCGT
CAGTGGGGCATGGGCTTCCTTTTGCAAAGCAATGATAAACAGCCTTCATTCTTGTGGGAGCGTTACAAGGC
GTTTTTCCCAACCGCAGAGGCAAAATTGCGAGCGATGAAGCCAGATGAGTTTGCGCAAATCCAGCAGGCGG
TAATTACCCAGATGCTGCAGGCACCGCAAACGCTCGGCGAAGAAGCATCGAAGTTAAGTAAAGATTTCGAT
CGCGGCAATATGCGCTTCGATTCGCGTGATAAAATCGTGGCCCAGATAAAACTGCTGACGCCGCAAAAACT
TGCTGATTTCTTCCATCAGGCGGTGGTCGAGCCGCAAGGCATGGCTATTCTGTCGCAGATTTCCGGCAGCC
AGAACGGGAAAGCCGAATATGTACACCCTGAAGGCTGGAAAGTGTGGGAGAACGTCAGCGCGTTGCAGCAA
ACAATGCCCCTGATGAGTGAAAAGAATGAGTGA
```

SEQ ID NO:5 is the amino acid sequence of the wild-type Protease III protein.

```
MPRSTWFKALLLLVALWAPLSQAETGWQPIQETIRKSDKDNRQYQAIRLDNGMVVLLVSDPQAVKSLSALV
VPVGSLEDPEAYQGLAHYLEHMSLMGSKKYPQADSLAEYLKMHGGSHNASTAPYRTAFYLEVENDALPGAV
DRLADAIAEPLLDKKYAERERNAVNAELTMARTRDGMRMAQVSAETINPAHPGSKFSGGNLETLSDKPGNP
VQQALKDFHEKYYSANLMKAVIYSNKPLPELAKMAADTFGRVPNKESKKPEITVPVVTDAQKGIIIHYVPA
LPRKVLRVEFRIDNNSAKFRSKTDELITYLIGNRSPGTLSDWLQKQGLVEGISANSDPIVNGNSGVLAISA
SLTDKGLANRDQVVAAIFSYLNLLREKGIDKQYFDELANVLDIDFRYPSITRDMDYVEWLADTMIRVPVEH
TLDAVNIADRYDAKAVKERLAMMTPQNARIWYISPKEPHNKTAYFVDAPYQVDKISAQTFADWQKKAADIA
LSLPELNPYIPDDFSLIKSEKKYDHPELIVDESNLRVVYAPSRYFASEPKADVSLILRNPKAMDSARNQVM
FALNDYLAGLALDQLSNQASVGGISFSTNANNGLMVNANGYTQRLPQLFQALLEGYFSYTATEDQLEQAKS
WYNQMMDSAEKGKAFEQAIMPAQMLSQVPYFSRDERRKILPSITLKEVLAYRDALKSGARPEFMVIGNMTE
AQATTLARDVQKQLGADGSEWCRNKDVVVDKKQSVIFEKAGNSTDSALAAVFVPTGYDEYTSSAYSSLLGQ
IVQPWFYNQLRTEEQLGYAVFAFPMSVGRQWGMGFLLQSNDKQPSFLWERYKAFFPTAEAKLRAMKPDEFA
QIQQAVITQMLQAPQTLGEEASKLSKDFDRGNMRFDSRDKIVAQIKLLTPQKLADFFHQAVVEPQGMAILS
QISGSQNGKAEYVHPEGWKVWENVSALQQTMPLMSEKNE*
```

FIG. 8D

SEQ ID NO:6 is the DNA sequence of a mutated knockout Protease III gene.

```
ATTCCCCGCAGCACCTGGTTCAAAGCATTATTGTTGTTAGTTGCCCTTTGGGCACATTAATGTCAGGCAGA
AACGGGATGGCAGCCGATTCAGGAAACCATCCGTAAAAGTGATAAAGATAACCGCCAGTATCAGGCTATAC
GTCTGGATAACGGTATGGTGGTCTTGCTGGTTTCTGATCCGCAGGCAGTTAAATCGCTCTCGGCGCTGGTG
GTGCCCGTTGGGTCGCTGGAAGATCCCGAGGCGTACCAGGGGCTGGCACATTACCTTGAACATATGAGTCT
GATGGGGTCGAAAAAGTACCCGCAGGCTGACAGTCTGGCCGAATATCTCAAAATGCACGGCGGTAGTCACA
ATGCCAGCACTGCGCCGTATCGCACGGCTTTCTATCTGGAAGTTGAGAACGACGCCTTGCCTGGTGCGGTA
GACCGCCTGGCCGATGCTATTGCTGAACCTTTGCTCGACAAGAAATATGCCGAACGTGAGCGTAATGCGGT
GAACGCTGAATTAACCATGGCGCGTACGCGTGACGGGATGCGCATGGCACAGGTCAGCGCAGAAACCATTA
ACCCGGCACACCCCGGTTCAAAGTTTTCTGGTGGTAACCTCGAAACTTTAAGCGACAAACCTGGTAATCCG
GTGCAGCAGGCGCTGAAAGATTTCCACGAGAAGTACTATTCCGCCAATTTGATGAAGGCGGTTATTTACAG
TAATAAACCGCTGCCGGAGTTGGCAAAAATGGCGGCGGACACCTTTGGTCGCGTGCCGAACAAAGAGAGCA
AAAAACCGGAAATCACCGTGCCGGTAGTCACCGACGCGCAAAAGGGCATTATCATTCATTACGTCCCTGCG
CTGCCGCGTAAAGTGTTGCGCGTTGAGTTTCGCATCGATAACAACTCAGCGAAGTTCCGTAGTAAAACCGA
TGAATTGATTACCTATCTGATTGGCAATCGCAGCCCAGGTACACTTTCTGACTGGCTGCAAAAGCAGGGAT
TAGTTGAGGGCATTAGCGCCAACTCCGATCCTATCGTCAACGGCAACAGCGGCGTATTAGCGATCTCTGCG
TCTTTAACCGATAAAGGCCTGGCTAATCGCGATCAGGTTGTGGCGGCAATTTTTAGCTATCTCAATCTGTT
ACGTGAAAAAGGCATTGATAAACAATACTTCGATGAACTGGCGAATGTGCTGGATATCGACTTCCGTTATC
CGTCGATCACCCGTGATATGGATTACGTCGAATGGCTGGCAGATACCATGATTCGCGTTCCTGTTGAGCAT
ACGCTGGATGCAGTCAATATTGCCGATCGGTACGATGCTAAAGCAGTAAAGGAACGTCTGGCGATGATGAC
GCCGCAGAATGCGCGTATCTGGTATATCAGCCCGAAAGAGCCGCACAACAAAACGGCTTACTTTGTCGATG
CGCCGTATCAGGTCGATAAAATCAGCGCACAAACTTTCGCCGACTGGCAGAAAAAGCCGCCGACATTGCG
CTCTCTTTGCCAGAGCTTAACCCTTATATTCCTGATGATTTCTCGCTGATTAAGTCAGAGAAGAAATACGA
CCATCCAGAGCTGATTGTTGATGAGTCGAATCTGCGCGTGGTGTATGCGCCAAGCCGTTATTTTGCCAGCG
AGCCCAAAGCTGATGTCAGCCTGATTTTGCGTAATCCGAAAGCCATGGACAGCGCCCGCAATCAGGTGATG
TTTGCGCTCAATGATTATCTCGCAGGGCTGGCGCTTGATCAGTTAAGCAACCAGGCGTCGGTTGGTGGCAT
AAGTTTTTTCCACCAACGCTAACAACGGCCTTATGGTTAATGCTAATGGTTACACCCAGCGTCTGCCGCAGC
TGTTCCAGGCATTGCTCGAGGGGTACTTTAGCTATACCGCTACGGAAGATCAGCTTGAGCAGGCGAAGTCC
TGGTATAACCAGATGATGGATTCCGCAGAAAAGGGTAAAGCGTTTGAGCAGGCGATTATGCCCGCGCAGAT
GCTCTCGCAAGTGCCGTACTTCTCGCGAGATGAACGGCGTAAAATTTTGCCCTCCATTACGTTGAAAGAGG
TGCTGGCCTATCGCGACGCCTTAAAATCAGGGGCTCGACCAGAGTTTATGGTTATCGGCAACATGACCGAG
GCCCAGGCAACAACGCTGGCACGCGATGTGCAAAAACAGTTGGGCGCTGATGGTTCAGAGTGGTGTCGAAA
CAAAGATGTAGTGGTCGATAAAAAACAATCCGTCATCTTTGAAAAGCCGGTAACAGCACCGACTCCGCAC
TGGCAGCGGTATTTGTACCGACTGGCTACGATGAATACACCAGCTCAGCCTATAGCTCTCTGTTGGGGCAG
ATCGTACAGCCGTGGTTCTACAATCAGTTGCGTACCGAAGAACAATTGGGCTATGCCGTGTTTGCGTTTCC
AATGAGCGTGGGGCGTCAGTGGGGCATGGGCTTCCTTTTGCAAAGCAATGATAAACAGCCTTCATTCTTGT
GGGAGCGTTACAAGGCGTTTTTCCCAACCGCAGAGGCAAAATTGCGAGCGATGAAGCCAGATGAGTTTGCG
CAAATCCAGCAGGCGGTAATTACCCAGATGCTGCAGGCACCGCAAACGCTCGGCGAAGAAGCATCGAAGTT
AAGTAAAGATTTCGATCGCGGCAATATGCGCTTCGATTCGCGTGATAAAATCGTGGCCCAGATAAAACTGC
TGACGCCGCAAAAACTTGCTGATTTCTTCCATCAGGCGGTGGTCGAGCCGCAAGGCATGGCTATTCTGTCG
CAGATTTCCGGCAGCCAGAACGGGAAAGCCGAATATGTACACCCTGAAGGCTGGAAAGTGTGGGAGAACGT
CAGCGCGTTGCAGCAAACAATGCCCCTGATGAGTGAAAGAATGAGTGA
```

FIG. 8E

SEQ ID NO:7 is the DNA sequence of the wild-type DegP gene.
ATGAAAAAAACCACATTAGCACTGAGTGCACTGGCTCTGAGTTTAGGTTTGGCGTTATCTCCGCTCTCTGC
AACGGCGGCTGAGACTTCTTCAGCAACGACAGCCCAGCAGATGCCAAGCCTTGCACCGATGCTCGAAAAGG
TGATGCCTTCAGTGGTCAGCATTAACGTAGAAGGTAGCACAACCGTTAATACGCCGCGTATGCCGCGTAAT
TTCCAGCAGTTCTTCGGTGATGATTCTCCGTTCTGCCAGGAAGGTTCTCCGTTCCAGAGCTCTCCGTTCTG
CCAGGGTGGCCAGGGCGGTAATGGTGGCGGCCAGCAACAGAAATTCATGGCGCTGGGTTCCGGCGTCATCA
TTGATGCCGATAAGGCTATGTCGTCACCAACAACCACGTTGTTGATAACGCGACGGTCATTAAAGTTCAA
CTGAGCGATGGCCGTAAGTTCGACGCAAGATGGTTGGCAAAGATCCGCGCTCTGATATCGCGCTGATCCA
AATCCAGAACCCGAAAAACCTGACCGCAATTAAGATGGCGGATTCTGATGCACTGCGCGTGGGTGATTACA
CCGTAGCGATTGGTAACCCGTTTGGTCTGGGCGAGACGGTAACTTCCGGGATTGTCTCTGCGCTGGGGCGT
AGCGGCCTGAATGCCGAAAACTACGAAAACTTCATCCAGACCGATGCAGCGATCAACCGTGGTAACTCCGG
TGGTGCGCTGGTTAACCTGAACGGCGAACTGATCGGTATCAACACCGCGATCCTCGCACCGGACGGCGGCA
ACATCGGTATCGGTTTTGCTATCCCGAGTAACATGGTGAAAAACCTGACCTCGCAGATGGTGGAATACGGC
CAGGTGAAACGCGGTGAGCTGGGTATTATGGGGACTGAGCTGAACTCCGAACTGGCGAAAGCGATGAAAGT
TGACGCCCAGCGCGGTGCTTTCGTAAGCCAGGTTCTGCCTAATTCCTCCGCTGCAAAAGCGGGCATTAAAG
CGGGTGATGTGATCACCTCACTGAACGGTAAGCCGATCAGCAGCTTTGCCGCACTGCGTGCTCAGGTGGGT
ACTATGCCGGTAGGCAGCAAACTGACCCTGGGCTTACTGCGCGACGGTAAGCAGGTTAACGTGAACCTGGA
ACTGCAGCAGAGCAGCCAGAATCAGGTTGATTCCAGCTCCATCTTCAACGGCATTGAAGGCGCTGAGATGA
GCAACAAAGGCAAAGATCAGGGCGTGGTAGTGAACAACGTGAAAACGGGCACTCCGGCTGCGCAGATCGGC
CTGAAGAAAGGTGATGTGATTATTGGCGCGAACCAGCAGGCAGTGAAAAACATCGCTGAACTGCGTAAAGT
TCTCGACAGCAAACCGTCTGTGCTGGCACTCAACATTCAGCGCGGCGACAGCACCATCTACCTGTTAATGC
AGTAA SEQ ID NO:8 is the amino acid sequence of the wild-type DegP protein.
MKKTTLALSALALSLGLALSPLSATAAETSSATTAQQMPSLAPMLEKVMPSVVSINVEGSTTVNTPRMPRN
FQQFFGDDSPFCQEGSPFQSSPFCQGGQGGNGGGQQQKFMALGSGVIIDADKGYVVTNNHVVDNATVIKVQ
LSDGRKFDAKMVGKDPRSDIALIQIQNPKNLTAIKMADSDALRVGDYTVAIGNPFGLGETVTSGIVSALGR
SGLNAENYENFIQTDAAINRGNSGGALVNLNGELIGINTAILAPDGGNIGIGFAIPSNMVKNLTSQMVEYG
QVKRGELGIMGTELNSELAKAMKVDAQRGAFVSQVLPNSSAAKAGIKAGDVITSLNGKPISSFAALRAQVG
TMPVGSKLTLGLLRDGKQVNVNLELQQSSQNQVDSSSIFNGIEGAEMSNKGKDQGVVVNNVKTGTPAAQIG
LKKGDVIIGANQQAVKNIAELRKVLDSKPSVLALNIQRGDSTIYLLMQ SEQ ID NO:9 is the DNA sequence of a mutated DegP gene.
ATGAAAAAAACCACATTAGCACTGAGTGCACTGGCTCTGAGTTTAGGTTTGGCGTTATCTCCGCTCTCTGC
AACGGCGGCTGAGACTTCTTCAGCAACGACAGCCCAGCAGATGCCAAGCCTTGCACCGATGCTCGAAAAGG
TGATGCCTTCAGTGGTCAGCATTAACGTAGAAGGTAGCACAACCGTTAATACGCCGCGTATGCCGCGTAAT
TTCCAGCAGTTCTTCGGTGATGATTCTCCGTTCTGCCAGGAAGGTTCTCCGTTCCAGAGCTCTCCGTTCTG
CCAGGGTGGCCAGGGCGGTAATGGTGGCGGCCAGCAACAGAAATTCATGGCGCTGGGTTCCGGCGTCATCA
TTGATGCCGATAAGGCTATGTCGTCACCAACAACCACGTTGTTGATAACGCGACGGTCATTAAAGTTCAA
CTGAGCGATGGCCGTAAGTTCGACGCAAGATGGTTGGCAAAGATCCGCGCTCTGATATCGCGCTGATCCA
AATCCAGAACCCGAAAAACCTGACCGCAATTAAGATGGCGGATTCTGATGCACTGCGCGTGGGTGATTACA
CCGTAGCGATTGGTAACCCGTTTGGTCTGGGCGAGACGGTAACTTCCGGGATTGTCTCTGCGCTGGGGCGT
AGCGGCCTGAATGCCGAAAACTACGAAAACTTCATCCAGACCGATGCAGCGATTAATCGTGGTAACGCCGG
TGGTGCGCTGGTTAACCTGAACGGCGAACTGATCGGTATCAACACCGCGATCCTCGCACCGGACGGCGGCA
ACATCGGTATCGGTTTTGCTATCCCGAGTAACATGGTGAAAAACCTGACCTCGCAGATGGTGGAATACGGC
CAGGTGAAACGCGGTGAGCTGGGTATTATGGGGACTGAGCTGAACTCCGAACTGGCGAAAGCGATGAAAGT
TGACGCCCAGCGCGGTGCTTTCGTAAGCCAGGTTCTGCCTAATTCCTCCGCTGCAAAAGCGGGCATTAAAG
CGGGTGATGTGATCACCTCACTGAACGGTAAGCCGATCAGCAGCTTTGCCGCACTGCGTGCTCAGGTGGGT
ACTATGCCGGTAGGCAGCAAACTGACCCTGGGCTTACTGCGCGACGGTAAGCAGGTTAACGTGAACCTGGA
ACTGCAGCAGAGCAGCCAGAATCAGGTTGATTCCAGCTCCATCTTCAACGGCATTGAAGGCGCTGAGATGA
GCAACAAAGGCAAAGATCAGGGCGTGGTAGTGAACAACGTGAAAACGGGCACTCCGGCTGCGCAGATCGGC
CTGAAGAAAGGTGATGTGATTATTGGCGCGAACCAGCAGGCAGTGAAAAACATCGCTGAACTGCGTAAAGT
TCTCGACAGCAAACCGTCTGTGCTGGCACTCAACATTCAGCGCGGCGACAGCACCATCTACCTGTTAATGC
AGTAA

FIG. 8F

SEQ ID NO:10 is the amino acid sequence of a mutated DegP protein.

MKKTTLALSALALSLGLALSPLSATAAETSSATTAQQMPSLAPMLEKVMPSVVSINVEGSTTVNTPRMPRN
FQQFFGDDSPFCQEGSPFQSSPFCQGGQGGNGGGQQQKFMALGSGVIIDADKGYVVTNNHVVDNATVIKVQ
LSDGRKFDAKMVGKDPRSDIALIQIQNPKNLTAIKMADSDALRVGDYTVAIGNPFGLGETVTSGIVSALGR
SGLNAENYENFIQTDAAINRGNAGGALVNLNGELIGINTAILAPDGGNIGIGFAIPSNMVKNLTSQMVEYG
QVKRGELGIMGTELNSELAKAMKVDAQRGAFVSQVLPNSSAAKAGIKAGDVITSLNGKPISSFAALRAQVG
TMPVGSKLTLGLLRDGKQVNVNLELQQSSQNQVDSSSIFNGIEGAEMSNKGKDQGVVVNNVKTGTPAAQIG
LKKGDVIIGANQQAVKNIAELRKVLDSKPSVLALNIQRGDSTIYLLMQ

SEQ ID NO: 11 is the sequence of the 5' oligonucleotide primer for the region of the mutated DegP gene comprising the Ase I restriction site.

CTGCCTGCGATTTTCGCCGGAACG

SEQ ID NO: 12 is the sequence of the 3' oligonucleotide primer for the region of the mutated DegP gene comprising the Ase I restriction site.

CGCATGGTACGTGCCACGATATCC

SEQ ID NO: 13 is the sequence of the 5' oligonucleotide primer for the region of the mutated Tsp gene comprising the Ase I restriction site.

GGGAAATGAACCTGAGCAAAACGC

SEQ ID NO: 14 is the sequence of the 3' oligonucleotide primer for the region of the mutated Protease III gene comprising the Ase I restriction site.

GGGAAAGGCGGCGGAACCGCCTAG

SEQ ID NO: 15 is the sequence of the 5' oligonucleotide primer for the region of the mutated Protease III gene comprising the Ase I restriction site.

CTACTGTGCCAGCGGTGGTAATGG

SEQ ID NO: 16 is the sequence of the 3' oligonucleotide primer for the region of the mutated Tsp gene comprising the Ase I restriction site.

GCATCATAATTTTCTTTTTACCTC

SEQ ID NO: 17 is the DNA sequence of the wild-type spr gene.
ATGGTCAAATCTCAACCGATTTTGAGATATATCTTGCGCGGGATTCCCGCGATTGCAGTAGCGGTTCTGCT
TTCTGCATGTAGTGCAAATAACACCGCAAAGAATATGCATCCTGAGACACGTGCAGTGGGTAGTGAAACAT
CATCACTGCAAGCTTCTCAGGATGAATTTGAAAACCTGGTTCGTAATGTCGACGTAAAATCGCGAATTATG
GATCAGTATGCTGACTGGAAAGGCGTACGTTATCGTCTGGGCGGCAGCACTAAAAAAGGTATCGATTGTTC
TGGTTTCGTACAGCGTACATTCCGTGAGCAATTTGGCTTAGAACTTCCGCGTTCGACTTACGAACAGCAGG
AAATGGGTAAATCTGTTTCCCGCAGTAATTTGCGTACGGGTGATTTAGTTCTGTTCCGTGCCGGTTCAACG
GGACGCCATGTCGGTATTTATATCGGCAACAATCAGTTTGTCCATGCTTCCACCAGCAGTGGTGTTATTAT
TTCCAGCATGAATGAACCGTACTGGAAGAAGCGTTACAACGAAGCACGCCGGGTTCTCAGCCGCAGC

FIG. 8G

SEQ ID NO: 18 is the amino acid sequence of the wild-type spr gene including the signal sequence which is the first 26 amino acid residues.
MVKSQPILRYILRGIPAIAVAVLLSACSANNTAKNMHPETRAVGSETSSLQASQDEFENLVRNVDVKSRIM
DQYADWKGVRYRLGGSTKKGIDCSGFVQRTFREQFGLELPRSTYEQQEMGKSVSRSNLRTGDLVLFRAGST
GRHVGIYIGNNQFVHASTSSGVIISSMNEPYWKKRYNEARRVLSRS SEQ ID NO: 19 the non-mutated spr gene without the signal sequence.
CSANNTAKNMHPETRAVGSETSSLQASQDEFENLVRNVDVKSRIMDQYADWKGVRYRLGGSTKKGIDCSGF
VQRTFREQFGLELPRSTYEQQEMGKSVSRSNLRTGDLVLFRAGSTGRHVGIYIGNNQFVHASTSSGVIISS
MNEPYWKKRYNEARRVLSRS SEQ ID NO: 20 a mutated OmpT sequence comprising D210A and H212A mutations.
ATGCGGGCGAAACTTCTGGGAATAGTCCTGACAACCCCTATTGCGATCAGCTCTTTTGCTTCTACCGAGAC
TTTATCGTTTACTCCTGACAACATAAATGCGGACATTAGTCTTGGAACTCTGAGCGGAAAAACAAAAGAGC
GTGTTTATCTAGCCGAAGAAGGAGGCCGAAAAGTCAGTCAACTCGACTGGAAATTCAATAACGCTGCAATT
ATTAAAGGTGCAATTAATTGGGATTTGATGCCCCAGATATCTATCGGGGCTGCTGGCTGGACAACTCTCGG
CAGCCGAGGTGGCAATATGGTCGATCAGGACTGGATGGATTCCAGTAACCCCGGAACCTGGACGGATGAAA
GTAGACACCCTGATACACAACTCAATTATGCCAACGAATTTGATCTGAATATCAAAGGCTGGCTCCTCAAC
GAACCCAATTACCGCCTGGGACTCATGGCCGGATATCAGGAAAGCCGTTATAGCTTTACAGCCAGAGGTGG
TTCCTATATCTACAGTTCTGAGGAGGGATTCAGAGATGATATCGGCTCCTTCCCGAATGGAGAAAGAGCAA
TCGGCTACAAACAACGTTTTAAAATGCCCTACATTGGCTTGACTGGAAGTTATCGTTATGAAGATTTTGAA
CTCGGTGGCACATTTAAATACAGCGGCTGGGTGGAATCATCTGATAACGCTGAAGCTTATGACCCGGGAAA
AAGAATCACTTATCGCAGTAAGGTCAAAGACCAAAATTACTATTCTGTTGCAGTCAATGCAGGTTATTACG
TCACACCTAACGCAAAAGTTTATGTTGAAGGCGCATGGAATCGGGTTACGAATAAAAAAGGTAATACTTCA
CTTTATGATCACAATAATAACACTTCAGACTACAGCAAAAATGGAGCAGGTATAGAAAACTATAACTTCAT
CACTACTGCTGGTCTTAAGTACACATTTTAA SEQ ID NO: 21 a mutated OmpT sequence comprising D210A and H212A mutations.
MRAKLLGIVLTTPIAISSFASTETLSFTPDNINADISLGTLSGKTKERVYLAEEGGRKVSQLDWKFNNAAI
IKGAINWDLMPQISIGAAGWTTLGSRGGNMVDQDWMDSSNPGTWTDESRHPDTQLNYANEFDLNIKGWLLN
EPNYRLGLMAGYQESRYSFTARGGSYIYSSEEGFRDDIGSFPNGERAIGYKQRFKMPYIGLTGSYRYEDFE
LGGTFKYSGWVESSDNAEAYDPGKRITYRSKVKDQNYYSVAVNAGYYVTPNAKVYVEGAWNRVTNKKGNTS
LYDHNNNTSDYSKNGAGIENYNFITTAGLKYTF SEQ ID NO: 22 is the nucleotide sequence of a mutated knockout OmpT sequence.
ATTCGGGCGAAACTTCTGGGAATAGTCCTGACAACCCCTATTGCGATCAGCTCTTTTGCTTCTACCGAGAC
TTTATCGTTTACTCCTGACAACATAAATGCGGACATTAGTCTTGGAACTCTGAGCGGAAAAACAAAAGAGC
GTGTTTATCTAGCCGAAGAAGGAGGCCGAAAAGTCAGTCAACTCGACTGGAAATTCAATAACGCTGCAATT
ATTAAAGGTGCAATTAATTGGGATTTGATGCCCCAGATATCTATCGGGGCTGCTGGCTGGACAACTCTCGG
CAGCCGAGGTGGCAATATGGTCGATCAGGACTGGATGGATTCCAGTAACCCCGGAACCTGGACGGATGAAA
GTAGACACCCTGATACACAACTCAATTATGCCAACGAATTTGATCTGAATATCAAAGGCTGGCTCCTCAAC
GAACCCAATTACCGCCTGGGACTCATGGCCGGATATCAGGAAAGCCGTTATAGCTTTACAGCCAGAGGTGG
TTCCTATATCTACAGTTCTGAGGAGGGATTCAGAGATGATATCGGCTCCTTCCCGAATGGAGAAAGAGCAA
TCGGCTACAAACAACGTTTTAAAATGCCCTACATTGGCTTGACTGGAAGTTATCGTTATGAAGATTTTGAA
CTCGGTGGCACATTTAAATACAGCGGCTGGGTGGAATCATCTGATAACGATGAACACTATGACCCGGGAAA
AAGAATCACTTATCGCAGTAAGGTCAAAGACCAAAATTACTATTCTGTTGCAGTCAATGCAGGTTATTACG
TCACACCTAACGCAAAAGTTTATGTTGAAGGCGCATGGAATCGGGTTACGAATAAAAAAGGTAATACTTCA
CTTTATGATCACAATAATAACACTTCAGACTACAGCAAAAATGGAGCAGGTATAGAAAACTATAACTTCAT
CACTACTGCTGGTCTTAAGTACACATTTTAA

FIG. 8H

SEQ ID NO: 23 shows the sequence of the OmpA oligonucleotide adapter.
CGATTGAATGGAGAACTTGAATTCGGGCGAAACTTCTGGGAATAG SEQ ID NO: 24 shows a cassette encoding intergenic sequence 1 (IGS1) for *E. coli* Fab expression.
AAGTTTTAATAGAGGAGAGTGTTAATGAAGAAG SEQ ID NO: 25 shows the oligonucleotide cassette encoding intergenic sequence 2 (IGS2) for *E. coli* Fab expression.
AAGTTTTAATAGAGGGGAGTGTTAAAATGAAGAAG SEQ ID NO: 26 shows a cassette encoding intergenic sequence 3 (IGS3) for *E. coli* Fab expression.
AAGCTTTAATAGAGGAGAGTGTTGAGGAGGAAAAAAAAATGAAGAAA SEQ ID NO: 27 shows a cassette encoding intergenic sequence 4 (IGS4) for *E. coli* Fab expression.
AAGCTTTAATAGAGGAGAGTGTTGACGAGGATTATATAATGAAGAAA SEQ ID NO: 28 is the DNA sequence of the wild-type FkpA gene.
ATGAAATCACTGTTTAAAGTAACGCTGCTGGCGACCACAATGGCCGTTGCCCTGCATGCACCAATCACTTT
TGCTGCTGAAGCTGCAAAACCTGCTACAGCTGCTGACAGCAAAGCAGCGTTCAAAAATGACGATCAGAAAT
CAGCTTATGCACTGGGTGCCTCGCTGGGTCGTTACATGGAAAACTCTCTAAAAGAACAAGAAAAACTGGGC
ATCAAACTGGATAAAGATCAGCTGATCGCTGGTGTTCAGGATGCATTTGCTGATAAGAGCAAACTCTCCGA
CCAAGAGATCGAACAGACTCTACAAGCATTCGAAGCTCGCGTGAAGTCTTCTGCTCAGGCGAAGATGGAAA
AAGACGCGGCTGATAACGAAGCAAAAGGTAAAGAGTACCGCGAGAAATTTGCCAAAGAGAAAGGTGTGAAA
ACCTCTTCAACTGGTCTGGTTTATCAGGTAGTAGAAGCCGGTAAAGGCGAAGCACCGAAAGACAGCGATAC
TGTTGTAGTGAACTACAAAGGTACGCTGATCGACGGTAAAGAGTTCGACAACTCTTACACCCGTGGTGAAC
CGCTTTCTTTCCGTCTGGACGGTGTTATCCCGGGTTGGACAGAAGGTCTGAAGAACATCAAGAAAGGCGGT
AAGATCAAACTGGTTATTCCACCAGAACTGGCTTACGGCAAAGCGGGTGTTCCGGGGATCCCACCGAATTC
TACCCTGGTGTTTGACGTAGAGCTGCTGGATGTGAAACCAGCGCCGAAGGCTGATGCAAAGCCGGAAGCTG
ATGCGAAAGCCGCAGATTCTGCTAAAAAA SEQ ID NO: 29 is the protein sequence of the wild-type FkpA gene.
MKSLFKVTLLATTMAVALHAPITFAAEAAKPATAADSKAAFKNDDQKSAYALGASLGRYMENSLKEQEKLG
IKLDKDQLIAGVQDAFADKSKLSDQEIEQTLQAFEARVKSSAQAKMEKDAADNEAKGKEYREKFAKEKGVK
TSSTGLVYQVVEAGKGEAPKDSDTVVVNYKGTLIDGKEFDNSYTRGEPLSFRLDGVIPGWTEGLKNIKKGG
KIKLVIPPELAYGKAGVPGIPPNSTLVFDVELLDVKPAPKADAKPEADAKAADSAKK SEQ ID NO: 30 is the DNA sequence of the FkpA his tagged gene.
ATGAAATCACTGTTTAAAGTAACGCTGCTGGCGACCACAATGGCCGTTGCCCTGCACGCACCAATCACTTT
TGCTGCTGAAGCTGCAAAACCTGCTACTGCTGCTGACAGCAAAGCAGCGTTCAAAAATGACGATCAGAAAT
CAGCTTATGCACTGGGTGCCTCGCTGGGTCGTTACATGGAAAACTCTCTAAAAGAACAAGAAAAACTGGGC
ATCAAACTGGATAAAGATCAACTGATCGCTGGTGTTCAGGATGCATTTGCTGATAAGAGCAAACTCTCCGA
CCAAGAGATCGAACAGACTCTACAAGCATTTGAAGCTCGCGTGAAGTCTTCTGCTCAGGCGAAGATGGAAA
AAGACGCGGCTGATAACGAAGCAAAAGGTAAAGAGTACCGCGAGAAATTTGCCAAAGAGAAAGGTGTGAAA
ACCTCTTCAACTGGTCTGGTTTATCAGGTAGTAGAAGCCGGTAAAGGCGAAGCACCGAAAGACAGCGATAC
TGTTGTAGTGAACTACAAAGGTACGCTGATCGACGGTAAAGAGTTCGACAACTCTTACACCCGTGGTGAAC
CGCTTTCTTTCCGTCTGGACGGTGTTATCCCGGGTTGGACAGAAGGTCTGAAGAACATCAAGAAAGGCGGT
AAGATAAAACTGGTTATTCCACCAGAACTGGCTTACGGCAAAGCGGGTGTTCCGGGGATTCCACCAAATTC
TACCCTGGTGTTTGACGTAGAGCTGCTGGATGTGAAACCAGCGCCGAAGGCTGATGCAAAGCCGGAAGCTG
ATGCGAAAGCCGCAGATTCTGCTAAAAAACACCATCACCATCACCAC

FIG. 8I

SEQ ID NO: 31 is the protein sequence of the FkpA his tagged gene.
MKSLFKVTLLATTMAVALHAPITFAAEAAKPATAADSKAAFKNDDQKSAYALGASLGRYMENSLKEQEKLG
IKLDKDQLIAGVQDAFADKSKLSDQEIEQTLQAFEARVKSSAQAKMEKDAADNEAKGKEYREKFAKEKGVK
TSSTGLVYQVVEAGKGEAPKDSDTVVVNYKGTLIDGKEFDNSYTRGEPLSFRLDGVIPGWTEGLKNIKKGG
KIKLVIPPELAYGKAGVPGIPPNSTLVFDVELLDVKPAPKADAKPEADAKAADSAKKHHHHHH SEQ ID NO: 32 is the DNA sequence of the wild-type skp gene.
GTGAAAAAGTGGTTATTAGCTGCAGGTCTCGGTTTAGCACTGGCAACTTCTGCTCAGGCGGCTGACAAAAT
TGCAATCGTCAACATGGGCAGCCTGTTCCAGCAGGTAGCGCAGAAAACCGGTGTTTCTAACACGCTGGAAA
ATGAGTTCAAAGGCCGTGCCAGCGAACTGCAGCGTATGGAAACCGATCTGCAGGCTAAAATGAAAAAGCTG
CAGTCCATGAAAGCGGGCAGCGATCGCACTAAGCTGGAAAAAGACGTGATGGCTCAGCGCCAGACTTTTGC
TCAGAAAGCGCAGGCTTTTGAGCAGGATCGCGCACGTCGTTCCAACGAAGAACGCGGCAAACTGGTTACTC
GTATCCAGACTGCTGTGAAATCCGTTGCCAACAGCCAGGATATCGATCTGGTTGTTGATGCAAACGCCGTT
GCTTACAACAGCAGCGATGTAAAAGACATCACTGCCGACGTACTGAAACAGGTTAAATAA SEQ ID NO: 33 is the protein sequence of the wild-type skp gene.
MKKWLLAAGLGLALATSAQAADKIAIVNMGSLFQQVAQKTGVSNTLENEFKGRASELQRMETDLQAKMKKL
QSMKAGSDRTKLEKDVMAQRQTFAQKAQAFEQDRARRSNEERGKLVTRIQTAVKSVANSQDIDLVVDANAV
AYNSSDVKDITADVLKQVK SEQ ID NO: 34 is the DNA sequence of the skp his tagged gene.
ATGAAAAAGTGGTTATTAGCCGCAGGTCTCGGTTTAGCACTGGCAACTTCTGCTCAGGCGGCTGACAAAAT
TGCAATCGTCAACATGGGCAGCCTGTTCCAGCAGGTAGCGCAGAAAACCGGTGTTTCTAACACGCTGGAAA
ATGAGTTCAAAGGCCGTGCCAGCGAACTCCAGCGTATGGAAACCGATCTCCAGGCTAAAATGAAAAAGCTG
CAATCCATGAAAGCGGGCAGCGATCGCACTAAGCTGGAAAAAGACGTGATGGCTCAGCGCCAGACTTTTGC
TCAGAAAGCGCAGGCTTTTGAGCAGGATCGCGCACGTCGTTCCAACGAAGAACGCGGCAAACTGGTTACTC
GTATCCAGACTGCTGTGAAATCCGTTGCCAACAGCCAGGAAATCGATCTGGTTGTTGATGCAAACGCCGTT
GCTTACAACAGCAGCGATGTAAAAGACATCACTGCCGACGTACTGAAACAGGTTAAACACCATCACCATCA
CCAC SEQ ID NO: 35 is the protein sequence of the skp his tagged gene.
MKKWLLAAGLGLALATSAQAADKIAIVNMGSLFQQVAQKTGVSNTLENEFKGRASELQRMETDLQAKMKKL
QSMKAGSDRTKLEKDVMAQRQTFAQKAQAFEQDRARRSNEERGKLVTRIQTAVKSVANSQEIDLVVDANAV
AYNSSDVKDITADVLKQVKHHHHHH

CA170_1519 Ab sequences
CDRH1
GFTFSNYGMV             SEQ ID NO: 36

CDRH2
YIDSDGDNTYYRDSVKG      SEQ ID NO: 37

CDRH3
GIVRPFLY               SEQ ID NO: 38

CDRL1
KSSQSLVGASGKTYLY       SEQ ID NO: 39

CDRL2
LVSTLDS                SEQ ID NO: 40

CDRL3
LQGTHFPHT              SEQ ID NO: 41

FIG. 8J

Rat Ab 1519 VL region      SEQ ID NO: 42
DVVMTQTPLS LSVALGQPAS ISCKSSQSLV GASGKTYLYW LFQRSGQSPK RLIYLVSTLD
SGIPDRFSGS GAETDFTLKI RRVEADDLGV YYCLQGTHFP HTFGAGTKLE LK Rat Ab 1519 VL region      SEQ ID NO: 43
gatgttgtga tgacccagac tccactgtct tgtcggttg  ccttggaca  accagcctcc
atctcttgca agtcaagtca gagcctcgta ggtgctagtg gaaagacata tttgtattgg
ttatttcaga ggtccggcca gtctccaaag cgactaatct atctggtgtc cacactggac
tctggaattc ctgataggtt cagtggcagt ggagcagaga cagatttac  tcttaaaatc
cgcagagtgg aagccgatga tttgggagtt tattactgct tgcaaggtac acattttcct
cacacgtttg gagctgggac caagctggaa ttgaaa Rat Ab 1519 VL region with signal sequence underlined and italicised SEQ ID NO: 44
*MMSPAQFLFLLMLWIQGTSG*DVVMTQTPLSLSVALGQPASISCKSSQSLVGASGKTYLYWLFQRSGQSPK
RLIYLVSTLDSGIPDRFSGSGAETDFTLKIRRVEADDLGVYYCLQGTHFPHTFGAGTKLELK Rat Ab 1519 VL region with signal sequence underlined and italicised SEQ ID NO: 45
*atgatgagtc ctgcccagtt cctgtttctg ctgatgctct ggattcaggg aaccagtggt*
gatgttgtga tgacccagac tccactgtct tgtcggttg  ccttggaca  accagcctcc
atctcttgca agtcaagtca gagcctcgta ggtgctagtg gaaagacata tttgtattgg
ttatttcaga ggtccggcca gtctccaaag cgactaatct atctggtgtc cacactggac
tctggaattc ctgataggtt cagtggcagt ggagcagaga cagatttac  tcttaaaatc
cgcagagtgg aagccgatga tttgggagtt tattactgct tgcaaggtac acattttcct
cacacgtttg gagctgggac caagctggaa ttgaaa Rat Ab 1519 VH region SEQ ID NO: 46
EVPLVESGGG SVQPGRSMKL SCVVSGFTFS NYGMVWVRQA PKKGLEWVAY IDSDGDNTYY
RDSVKGRFTI SRNNAKSTLY LQMDSLRSED TATYYCTTGI VRPFLYWGQG TTVTVS Rat Ab 1519 VH region SEQ ID NO: 47
gaggtgccgc tggtggagtc tgggggcggc tcagtgcagc ctgggaggtc catgaaactc
tcctgtgtag tctcaggatt cactttcagt aattatggca tggtctgggt ccgccaggct
ccaaagaagg gtctggagtg ggtcgcatat attgattctg atggtgataa tacttactac
cgagattccg tgaagggccg attcactatc tccagaaata atgcaaaaag caccctatat
ttgcaaatgg acagtctgag gtctgaggac acggccactt attactgtac aacaggaatt
gtccggccct ttctctattg gggccaagga accacggtca ccgtctcg Rat Ab 1519 VH region with signal sequence underlined and italicised SEQ ID NO: 48
*MDISLSLAFL VLFIKGVRCE* VPLVESGGGS VQPGRSMKLS CVVSGFTFSN YGMVWVRQAP
KKGLEWVAYI DSDGDNTYYR DSVKGRFTIS RNNAKSTLYL QMDSLRSEDT ATYYCTTGIV
RPFLYWGQGT TVTVS Rat Ab 1519 VH region with signal sequence underlined and italicised SEQ ID NO: 49
*atggacatca gtctcagctt ggcttccctt gtccttttca taaaaggtgt ccggtgt*gag
gtgccgctgg tggagtctgg gggcggctca gtgcagcctg ggaggtccat gaaactctcc
tgtgtagtct caggattcac tttcagtaat tatggcatgg tctgggtccg ccaggctcca
aagaagggtc tggagtgggt cgcatatatt gattctgatg gtgataatac ttactaccga
gattccgtga agggccgatt cactatctcc agaaataatg caaaaagcac cctatatttg
caaatggaca gtctgaggtc tgaggacacg gccacttatt actgtacaac aggattgtc
cggccctttc tctattgggg ccaaggaacc acggtcaccg tctcg

FIG. 8K

1519 gL20 V-region SEQ ID NO: 50
DIQMTQSPSS LSASVGDRVT ITCKSSQSLV GASGKTYLYW LFQKPGKAPK RLIYLVSTLD
SGIPSRFSGS GSGTEFTLTI SSLQPEDFAT YYCLQGTHFP HTFGQGTKLE IK 1519 gL20 V-region SEQ ID NO: 51
gatatccaga tgacccagag tccaagcagt ctctccgcca gcgtaggcga tcgtgtgact
attacctgta aaagctccca gtccctggtg ggtgcaagcg gcaaaaccta cctgtactgg
ctcttccaga accgggcaa agctccgaaa cgcctgatct atctggtgtc tacccggat
agcggtattc cgtctcgttt ctccggtagc ggtagcggta ccgaattcac gctgaccatt
agctccctcc agccggagga ctttgctacc tattactgcc tccagggcac tcatttccg
cacactttcg gccagggtac caaactggaa atcaaa 1519 gL20 V-region with signal sequence underlined and italicized SEQ ID NO: 52
*MKKTAIAIAVALAGFATVAQ*DIQMTQSPSSLSASVGDRVTITCKSSQSLVGASGKTYLYWLFQKPGKAPK
RLIYLVSTLDSGIPSRFSGSGSGTEFTLTISSLQPEDFATYYCLQGTHFPHTFGQGTKLEIK 1519 gL20 V-region with signal sequence underlined and italicized SEQ ID NO: 53
*atgaaaaaga cagctatcgc aattgcagtg gccttggctg gtttcgctac cgtagcgcaa
gct*gatatcc agatgaccca gagtccaagc agtctctccg ccagcgtagg cgatcgtgtg
actattacct gtaaaagctc ccagtccctg gtgggtgcaa gcggcaaaac ctacctgtac
tggctcttcc agaaccggg caaagctccg aaacgcctga tctatctggt gtctacccctg
gatagcggta ttccgtctcg tttctccggt agcggtagcg gtaccgaatt cacgctgacc
attagctccc tccagccgga ggactttgct acctattact gcctccaggg cactcatttt
ccgcacactt tcggccaggg taccaaactg gaaatcaaa 1519 gL20 light chain (V + constant) SEQ ID NO: 54
DIQMTQSPSS LSASVGDRVT ITCKSSQSLV GASGKTYLYW LFQKPGKAPK RLIYLVSTLD
SGIPSRFSGS GSGTEFTLTI SSLQPEDFAT YYCLQGTHFP HTFGQGTKLE IKRTVAAPSV
FIFPPSDEQL KSGTASVVCL LNNFYPREAK VQWKVDNALQ SGNSQESVTE QDSKDSTYSL
SSTLTLSKAD YEKHKVYACE VTHQGLSSPV TKSFNRGEC 1519 gL20 light chain (V + constant) SEQ ID NO: 55
gatatccaga tgacccagag tccaagcagt ctctccgcca gcgtaggcga tcgtgtgact
attacctgta aaagctccca gtccctggtg ggtgcaagcg gcaaaaccta cctgtactgg
ctcttccaga accgggcaa agctccgaaa cgcctgatct atctggtgtc tacccctggat
agcggtattc cgtctcgttt ctccggtagc ggtagcggta ccgaattcac gctgaccatt
agctccctcc agccggagga ctttgctacc tattactgcc tccagggcac tcatttccg
cacactttcg gccagggtac caaactggaa atcaaacgta cggtagcggc cccatctgtc
ttcatcttcc cgccatctga tgagcagttg aaatctggaa ctgcctctgt tgtgtgcctg
ctgaataact ctatcccag agaggccaaa gtacagtgga aggtggataa cgccctccaa
tcgggtaact cccagagag tgtcacagag caggacagca aggacagcac ctacagcctc
agcagcaccc tgacgctgag caaagcagac tacgagaaac acaaagtcta cgcctgcgaa
gtcacccatc agggcctgag ctcaccagta acaaaaagtt taatagagg ggagtgt 1519 gL20 light chain with signal sequence underlined and italicized SEQ ID NO: 56
*MKKTAIAIAV ALAGFATVAQ A*DIQMTQSPS SLSASVGDRV TITCKSSQSL VGASGKTYLY
WLFQKPGKAP KRLIYLVSTL DSGIPSRFSG SGSGTEFTLT ISSLQPEDFA TYYCLQGTHF
PHTFGQGTKL EIKRTVAAPS VFIFPPSDEQ LKSGTASVVC LLNNFYPREA KVQWKVDNAL
QSGNSQESVT EQDSKDSTYS LSSTLTLSKA DYEKHKVYAC EVTHQGLSSP VTKSFNRGEC

FIG. 8L

1519 gL20 light chain with signal sequence underlined and italicized SEQ ID NO: 57
<u>atgaaaaaga cagctatcgc aattgcagtg gccttggctg gtttcgctac cgtagcgcaa</u>
<u>gct</u>gatatcc agatgaccca gagtccaagc agtctctccg ccagcgtagg cgatcgtgtg
actattacct gtaaagctc ccagtccctg gtgggtgcaa gcggcaaaac ctacctgtac
tggctcttcc agaaaccggg caaagctccg aaacgcctga tctatctggt gtctaccctg
gatagcggta ttccgtctcg tttctccggt agcggtagcg gtaccgaatt cacgctgacc
attagctccc tccagccgga ggactttgct acctattact gcctccaggg cactcatttt
ccgcacactt tcggccaggg taccaaactg gaaatcaaac gtacggtagc ggcccatct
gtcttcatct tcccgccatc tgatgagcag ttgaaatctg gaactgcctc tgttgtgtgc
ctgctgaata acttctatcc cagagaggcc aaagtacagt ggaaggtgga taacgccctc
caatcgggta actcccagga gagtgtcaca gagcaggaca gcaaggacag cacctacagc
ctcagcagca ccctgacgct gagcaaagca gactacgaga aacacaaagt ctacgcctgc
gaagtcaccc atcagggcct gagctcacca gtaacaaaaa gttttaatag aggggagtgt 1519 gH20 V-region SEQ ID NO: 58
EVPLVESGGG LVQPGGSLRL SCAVSGFTFS NYGMVWVRQA PGKGLEWVAY IDSDGDNTYY
RDSVKGRFTI SRDNAKSSLY LQMNSLRAED TAVYYCTTGI VRPFLYWGQG TLVTVS 1519 gH20 V-region SEQ ID NO: 59
gaggttccgc tggtcgagtc tggaggcggg cttgtccagc ctggagggag cctgcgtctc
tcttgtgcag tatctggctt cacgttctcc aactacggta tggtgtgggt cgtcaggct
ccaggtaaag gtctggaatg ggtggcgtat attgactccg acggcgacaa cacctactat
cgcgactctg tgaaggtcg cttcaccatt tcccgcgata cgccaaatc cagcctgtac
ctgcagatga acagcctgcg tgctgaagat actgcggtgt actattgcac cactggcatc
gtgcgtccgt ttctgtattg gggtcaggt accctcgtta ctgtctcg 1519 gH20 V-region with signal sequence underlined and italicized SEQ ID NO: 60
<u>*MKKTAIAIAV ALAGFATVAQ A*</u>EVPLVESGG GLVQPGGSLR LSCAVSGFTF SNYGMVWVRQ
APGKGLEWVA YIDSDGDNTY YRDSVKGRFT ISRDNAKSSL YLQMNSLRAE DTAVYYCTTG
IVRPFLYWGQ GTLVTVS 1519 gH20 V-region with signal sequence underlined and italicized SEQ ID NO: 61
<u>*atgaagaaga ctgctatagc aattgcagtg gcgctagctg gtttcgccac cgtggcgcaa
gct*</u>gaggttc cgctggtcga gtctggaggc gggcttgtcc agcctggagg gagcctgcgt
ctctcttgtg cagtatctgg cttcacgttc tccaactacg gtatggtgtg ggttcgtcag
gctccaggta aaggtctgga atgggtggcg tatattgact ccgacggcga caacacctac
tatcgcgact ctgtgaaagg tcgcttcacc atttcccgcg ataacgccaa atccagcctg
tacctgcaga tgaacagcct gcgtgctgaa gatactgcgg tgtactattg caccactggc
atcgtgcgtc cgtttctgta ttggggtcag ggtaccctcg ttactgtctc g 1519gH20 Fab' heavy chain (V + human gamma-1 CH1 + hinge) SEQ ID NO: 62
EVPLVESGGG LVQPGGSLRL SCAVSGFTFS NYGMVWVRQA PGKGLEWVAY IDSDGDNTYY
RDSVKGRFTI SRDNAKSSLY LQMNSLRAED TAVYYCTTGI VRPFLYWGQG TLVTVSSAST
KGPSVFPLAP SSKSTSGGTA ALGCLVKDYF PEPVTVSWNS GALTSGVHTF PAVLQSSGLY
SLSSVVTVPS SSLGTQTYIC NVNHKPSNTK VDKKVEPKSC DKTHTCAA

FIG. 8M

1519gH20 Fab' heavy chain (V + human gamma-1 CH1 + hinge) SEQ ID NO: 63
```
gaggttccgc tggtcgagtc tggaggcggg cttgtccagc ctggaggag cctgcgtctc
tcttgtgcag tatctggctt cacgttctcc aactacggta tggtgtgggt tcgtcaggct
ccaggtaaag gtctggaatg ggtggcgtat attgactccg acggcgacaa cacctactat
cgcgactctg tgaaaggtcg cttcaccatt tcccgcgata cgccaaatc cagcctgtac
ctgcagatga cagcctgcg tgctgaagat actgcggtgt actattgcac cactggcatc
gtgcgtccgt ttctgtattg gggtcagggt accctcgtta ctgtctcgag cgcttctaca
aagggcccat cggtcttccc cctggcaccc tcctccaaga gcacctctgg gggcacagcg
gccctgggct gcctggtcaa ggactacttc cccgaaccgg tgacggtgtc gtggaactca
ggcgcctga ccagcggcgt gcacaccttc ccggctgtcc tacagtcctc aggactctac
tccctcagca gcgtggtgac cgtgcctcc agcagcttgg cacccagac ctacatctgc
aacgtgaatc acaagcccag caacaccaag gtcgacaaga agttgagcc caaatcttgt
gacaaaactc acacatgcgc cgcg
```

1519gH20 Fab' heavy chain with signal sequence underlined and italicized SEQ ID NO: 64
*MKKTAIAIAV ALAGFATVAQ A*EVPLVESGG GLVQPGGSLR LSCAVSGFTF SNYGMVWVRQ APGKGLEWVA
YIDSDGDNTY YRDSVKGRFT ISRDNAKSSL YLQMNSLRAE DTAVYYCTTG IVRPFLYWGQ GTLVTVSSAS
TKGPSVFPLA PSSKSTSGGT AALGCLVKDY FPEPVTVSWN SGALTSGVHT FPAVLQSSGL YSLSSVVTVP
SSSLGTQTYI CNVNHKPSNT KVDKKVEPKS CDKTHTCAA 1519gH20 Fab' heavy chain with signal sequence underlined and italicized SEQ ID NO:65
```
atgaagaaga ctgctatagc aattgcagtg gcgctagctg gtttcgccac cgtggcgcaa
gctgaggttc cgctggtcga gtctggaggc gggcttgtcc agcctggagg agcctgcgt
ctctcttgtg cagtatctgg cttcacgttc tccaactacg gtatggtgtg gttcgtcag
gctccaggta aaggtctgga atgggtggcg tatattgact ccgacggcga acacctac
tatcgcgact ctgtgaaagg tcgcttcacc atttcccgcg ataacgccaa atccagcctg
tacctgcaga tgaacagcct gcgtgctgaa gatactgcgg tgtactattg caccactggc
atcgtgcgtc cgtttctgta ttggggtcag ggtaccctcg ttactgtctc gagcgcttct
acaaagggcc atcggtcttc ccctggca ccctcctcca agagcacctc tgggggcaca
gcggccctgg gctgcctggt caaggactac ttccccgaac cggtgacggt gtcgtggaac
tcaggcgccc tgaccagcgg cgtgcacacc ttcccggctg tcctacagtc ctcaggactc
tactccctca gcagcgtggt gaccgtgccc tccagcagct gggcaccca gacctacatc
tgcaacgtga atcacaagcc cagcaacacc aaggtcgaca gaaagttga gcccaaatct
tgtgacaaaa ctcacacatg cgccgcg
```

1519gH20 IgG4 heavy chain (V + human gamma-4P constant) SEQ ID NO: 66
EVPLVESGGG LVQPGGSLRL SCAVSGFTFS NYGMVWVRQA PGKGLEWVAY IDSDGDNTYY
RDSVKGRFTI SRDNAKSSLY LQMNSLRAED TAVYYCTTGI VRPFLYWGQG TLVTVSSAST
KGPSVFPLAP CSRSTSESTA ALGCLVKDYF PEPVTVSWNS GALTSGVHTF PAVLQSSGLY
SLSSVVTVPS SSLGTKTYTC NVDHKPSNTK VDKRVESKYG PPCPPCPAPE FLGGPSVFLF
PPKPKDTLMI SRTPEVTCVV VDVSQEDPEV QFNWYVDGVE VHNAKTKPRE EQFNSTYRVV
SVLTVLHQDW LNGKEYKCKV SNKGLPSSIE KTISKAKGQP REPQVYTLPP SQEEMTKNQV
SLTCLVKGFY PSDIAVEWES NGQPENNYKT TPPVLDSDGS FFLYSRLTVD KSRWQEGNVF
SCSVMHEALH NHYTQKSLSL SLGK

FIG. 8N

1519gH20 IgG4 heavy chain (V + human gamma-4P constant, exons underlined) SEQ ID NO:67

<u>gaggtaccacttgtggaaagcggaggaggtcttgtgcagcctggaggaagtttacgtctctcttgtgctgtgtctggc</u>
<u>ttcaccttctccaattacggaatggtctgggtcagacaagcacctggaaagggtcttgaatgggtggcctatattgac</u>
<u>tctgcggggacaacacctactatcgggattccgtgaaggacgcttcacaatctcccgagataacgccaagagctcac</u>
<u>tgtacctgcagatgaatagcctgagagccgaggatactgccgtgtactattgcacaacgggaatcgttaggcttttc</u>
<u>tgtactggggacagggcaccttggttactgtctcgagcgcttctacaaaggccatccgtcttcccctggcgcct</u>
gctccaggagcacctccgagagcacagccgccctgggctgcctggtcaaggactacttccccgaaccggtgacggtgt
cgtggaactcaggcgccctgaccagcggcgtgcacaccttcccggctgtcctacagtcctcaggactctactccctca
gcagcgtggtgaccgtgccctccagcagcttgggcacgaagacctacacctgcaacaagcccagcaacaccaaggtgga
caagagagttggtgagaggccagcacagggagggagggtgtctgctggaagccaggctcagcctcctgcctggacgc
acccc<u>ggctgtgcagccccagcccagggcagcaaggcatgccccatctgtctcctcacccggaggcctctgaccaccc</u>
<u>cactcatgcccagggagagggtcttctggattttccaccaggctccgggcagccacaggctggatgcccctaccccca</u>
<u>ggccctgcgcatacaggggcaggtgctgcgctcagacctgccaagagccatatccgggaggaccctgcccctgaccta</u>
<u>agcccaccccaaaggccaaactctccactccctcagctcagacaccttctctcctcccagatctgagtaactcccaat</u>
<u>cttctctctgcagagtccaaatatggtccccatgccaccatgcccaggtaagccaacccaggcctcgccctccagc</u>
tcaaggcgggacaggtgccctagagtagcctgcatccagggacagccccagccgggtgctgacgcatccacctccat
ctcttcctcag<u>cacctgagttcctggggggaccatcagtcttcctgttccccccaaaacccaaggacactctcatgat</u>
<u>ctcccggacccctgaggtcacgtgcgtggtggtggacgtgagccaggaagacccgaggtccagttcaactggtacgt</u>
<u>ggatggcgtggaggtgcataatgccaagacaaagccgcgggaggagcagttcaacagcacgtaccgtgtggtcagcgt</u>
<u>cctcaccgtcctgcaccaggactggctgaacggcaaggagtacaagtgcaaggtctccaacaaaggcctcccgtcctc</u>
<u>catcgagaaaaccatctccaaagccaaaggtgggacccacgggtgcgagggccacatggacagaggtcagctcggcc</u>
<u>cacccctctgccctgggagtgaccgctgtgccaacctctgtcctacagggcagccccgagagccacaggtgtacaccc</u>
<u>tgcccccatcccaggaggagatgaccaagaaccaggtcagcctgacctgcctggtcaaaggcttctaccccagcgaca</u>
<u>tcgccgtggagtgggagagcaatgggcagccggagaacaactacaagaccacgcctcccgtgctggactccgacggct</u>
<u>ccttcttcctctacagcaggctaaccgtggacaagagcaggtggcaggaggggaatgtcttctcatgctccgtgatgc</u>
<u>atgaggctctgcacaaccactacacacagaagagcctctccctgtct ctgggtaaa</u>

1519gL20 FabFv light chain SEQ ID NO: 68
DIQMTQSPSS LSASVGDRVT ITCKSSQSLV GASGKTYLYW LFQKPGKAPK RLIYLVSTLD
SGIPSRFSGS GSGTEFTLTI SSLQPEDFAT YYCLQGTHFP HTFGQGTKLE IKRTVAAPSV
FIFPPSDEQL KSGTASVVCL LNNFYPREAK VQWKVDNALQ SGNSQESVTE QDSKDSTYSL
SSTLTLSKAD YEKHKVYACE VTHQGLSSPV TKSFNRGECS GGGGSGGGGS GGGGSDIQMT
QSPSSVSASV GDRVTITCQS SPSVWSNFLS WYQQKPGKAP KLLIYEASKL TSGVPSRFSG
SGSGTDFTLT ISSLQPEDFA TYYCGGGYSS ISDTTFGCGT KVEIKRT 1519gL20 FabFv light chain SEQ ID NO: 69
gatatccaga tgacccagag cccatctagc ttatccgctt ccgttggtga tcgcgtgaca
attacgtgta agagctccca atctctcgtg ggtgcaagtg gcaagaccta tctgtactgg
ctctttcaga agcctggcaa ggcaccaaaa cggctgatct atctggtgtc taccttgac
tctgggatac cgtcacgatt ttccggatct gggagcggaa ctgagttcac actcacgatt
tcatcgctgc aacccgagga ctttgctacc tactactgcc tgcaaggcac tcatttccct
cacactttcg gccaggggac aaaactcgaa atcaaacgta cggtagcggc ccatctgtc
ttcatcttcc cgccatctga tgagcagttg aaatctggaa ctgcctctgt tgtgtgcctg
ctgaataact tctatcccag agaggccaaa gtacagtgga aggtggataa cgccctccaa
tcgggtaact cccaggagag tgtcacagag caggacagca aggacagcac ctacagcctg
agcagcaccc tgacgctgtc taaagcagac tacgagaaac acaaagtgta cgcctgcgaa
gtcacccatc agggcctgag ctcaccagta acaaaaagtt taatagagg ggagtgtagc
ggtggcggtg gcagtggtgg gggaggctcc ggaggtggcg gttcagacat acaaatgacc
cagagtcctt catcggtatc cgcgtccgtt ggcgataggg tgactattac atgtcaaagc
tctcctagcg tctggagcaa ttttctatcc tggtatcaac agaaaccggg aaggctcca
aaacttctga tttatgaagc ctcgaaactc accagtggag ttccgtcaag attcagtggc
tctggatcag ggacagactt cacgttgaca atcagttcgc tgcaaccaga ggactttgcg
acctactatt gtggtgaggg ttacagtagc ataagtgata cgacatttgg gtgcggtact
aaggtggaaa tcaaacgtac c

FIG. 8O
1519gL20 FabFv light chain with signal sequence underlined and italicised SEQ ID NO: 70
*MSVPTQVLGLLLLWLTDARC*DIQMTQSPSSLSASVGDRVTITCKSSQSLVGASGKTYLYWLFQKPGKAPKRLIYL
VSTLDSGIPSRFSGSGSGTEFTLTISSLQPEDFATYYCLQGTHFPHTFGQGTKLEIKRTVAAPSVFIFPPSDEQL
KSGTASVVCLLNNFYPREAKVQWKVDNALQSGNSQESVTEQDSKDSTYSLSSTLTLSKADYEKHKVYACEVTHQG
LSSPVTKSFNRGECSGGGGSGGGGSGGGGSDIQMTQSPSSVSASVGDRVTITCQSSPSVWSNFLSWYQQKPGKAP
KLLIYEASKLTSGVPSRFSGSGSGTDFTLTISSLQPEDFATYYCGGGYSSISDTTFGCGTKVEIKRT
1519gL20 FabFv light chain with signal sequence underlined and italicised SEQ ID NO: 71
*atgtctgtccccacccaagtcctcggactcctgctactctggcttacagatgccagatgc*gatatccagat
gacccagagcccatctagcttatccgcttccgttggtgatcgcgtgacaattacgtgtaagagctcccaat
ctctcgtgggtgcaagtggcaagacctatctgtactggctctttcagaagcctggcaaggcaccaaaacgg
ctgatctatctggtgtctacccttgactctgggataccgtcacgatttccggatctgggagcggaactga
gttcacactcacgatttcatcgctgcaacccgaggactttgctacctactactgcctgcaaggcactcatt
tccctcacactttcggccaggggacaaaactcgaaatcaaacgtacggtagcggccccatctgtcttcatc
ttcccgccatctgatgagcagttgaaatctggaactgcctctgttgtgtgcctgctgaataacttctatcc
cagagaggccaaagtacagtggaaggtggataacgccctccaatcgggtaactcccaggagagtgtcacag
agcaggacagcaaggacagcacctacagcctgagcagcaccctgacgctgtctaaagcagactacgagaaa
cacaaagtgtacgcctgcgaagtcacccatcagggcctgagctcaccagtaacaaaagttttaatagagg
ggagtgtagcggtggcggtggcagtggtggggaggctccggaggtggcggttcagacatacaaatgaccc
agagtccttcatcggtatccgcgtccgttggcgatagggtgactattacatgtcaaagctctcctagcgtc
tggagcaattttctatcctggtatcaacagaaaccggggaaggctccaaaacttctgatttatgaagcctc
gaaactcaccagtggagttccgtcaagattcagtggctctggatcagggacagacttcacgttgacaatca
gttcgctgcaaccagaggactttgcgacctactattgtggtggaggttacagtagcataagtgatacgaca
tttgggtgcggtactaaggtggaaatcaaacgtacc
1519gH20 FabFv heavy chain SEQ ID NO: 72
EVPLVESGGGLVQPGGSLRLSCAVSGFTFSNYGMVWVRQAPGKGLEWVAYIDSDGDNTYYRDSVKGRFTIS
RDNAKSSLYLQMNSLRAEDTAVYYCTTGIVRPFLYWGQGTLVTVSSASTKGPSVFPLAPSSKSTSGGTAAL
GCLVKDYFPEPVTVSWNSGALTSGVHTFPAVLQSSGLYSLSSVVTVPSSSLGTQTYICNVNHKPSNTKVDK
KVEPKSCSGGGGSGGGGTGGGGSEVQLLESGGGLVQPGGSLRLSCAVSGIDLSNYAINWVRQAPGKCLEWI
GIIWASGTTFYATWAKGRFTISRDNSKNTVYLQMNSLRAEDTAVYYCARTVPGYSTAPYFDLWGQGTLVTV
SS
1519gH20 FabFv heavy chain SEQ ID NO: 73
gaggtaccacttgtggaaagcggaggaggtcttgtgcagcctggaggaagtttacgtctctcttgtgctgt
gtctggcttcaccttctccaattacggaatggtctgggtcagacaagcacctggaaagggtcttgaatggg
tggcctatattgactctgacggggacaacacctactatcgggattccgtgaaaggacgcttcacaatctcc
cgagataacgccaagagctcactgtacctgcagatgaatagcctgagagccgaggatactgccgtgtacta
ttgcacaacgggaatcgttaggcctttctgtactggggacagggcaccttggttactgtctcgagcgcgt
ccacaaagggcccatcggtcttccccctggcaccctcctccaagagcacctctgggggcacagcggccctg
ggctgcctggtcaaggactacttccccgaaccagtgacggtgtcgtggaactcaggtgcctgaccagcgg
cgttcacaccttcccggctgtcctacagtcttcaggactctactccctgagcagcgtggtgaccgtgcct
ccagcagcttgggcacccagacctacatctgcaacgtgaatcacaagcccagcaacaccaaggtcgataag
aaagttgagcccaaatcttgtagtggaggtggggctcaggtggaggcgggaccggtggaggtggcagcga
ggttcaactgcttgagtctggaggaggcctagtccagcctggagggagcctgcgtctctcttgtgcagtaa
gcggcatcgacctgagcaattacgccatcaactgggtgagacaagctccggggaagtgtttagaatggatc
ggtataatatgggccagtgggacgaccttttatgctacatgggcgaaggaaggtttacaattagccggga
caatagcaaaaacaccgtgtatctccaaatgaactccttgcgagcaggagacacggcggtgtactattgtg
ctcgcactgtcccaggttatagcactgcaccctacttcgatctgtggggacaagggacctggtgactgtt
tcaagt
1519gH20 FabFv heavy chain with signal sequence underlined and italicised SEQ ID NO: 74
*MEWSWVFLFFLSVTTGVHS*EVPLVESGGGLVQPGGSLRLSCAVSGFTFSNYGMVWVRQAPGKGLEWVAYID
SDGDNTYYRDSVKGRFTISRDNAKSSLYLQMNSLRAEDTAVYYCTTGIVRPFLYWGQGTLVTVSSASTKGP
SVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCSGGGGSGGGGTGGGGSEVQLLESGGGLVQPGGSLRLSCAVSGIDL
SNYAINWVRQAPGKCLEWIGIIWASGTTFYATWAKGRFTISRDNSKNTVYLQMNSLRAEDTAVYYCARTVP
GYSTA PYFDLWGQGTLVTVSS

SEQUENCE LISTING

<160> NUMBER OF SEQ ID NOS: 86

<210> SEQ ID NO 1
<211> LENGTH: 2049
<212> TYPE: DNA
<213> ORGANISM: Escherichia coli

<400> SEQUENCE: 1

```
atgaacatgt tttttaggct taccgcgtta gctggcctgc ttgcaatagc aggccagacc      60
ttcgctgtag aagatatcac gcgtgctgat caaattccgg tattaaagga agagacgcag     120
catgcgacgg taagtgagcg cgtaacgtcg cgcttcaccc gttctcatta tcgccagttc     180
gacctcgatc aggcattttc ggccaaaatc tttgaccgct acctgaatct gctcgattac     240
agccacaacg tgctgctggc aagcgatgtt gaacagttcg cgaaaaagaa accgagtta     300
ggcgatgaac tgcgttcagg caaactcgac gttttctacg atctctacaa tctggcgcaa     360
aagcgccgtt ttgagcgtta ccagtacgct ttgtcggtac tggaaaagcc gatggatttc     420
accggcaacg acacttataa ccttgaccgc agcaaagcgc cctggccgaa aaacgaggct     480
gagttgaacg cgctgtggga cagtaaagtc aaattcgacg agttaagcct gaagctgaca     540
ggaaaaacgg ataaagaaat tcgtgaaacc ctgactcgcc gctacaaatt tgccattcgt     600
cgtctggcgc aaaccaacag cgaagatgtt ttctcgctgg caatgacggc gtttgcgcgt     660
gaaatcgacc cgcataccaa ctatctttcc ccgcgtaata ccgaacagtt caacactgaa     720
atgagtttgt cgctggaagg tattggcgca gtgctgcaaa tggatgatga ctacaccgtt     780
atcaattcga tggtggcagg tggtccggca gcgaagagta agctatcag cgttggtgac     840
aaaattgtcg gtgttggtca acaggcaag ccgatggttg acgtgattgg ctggcgtctt     900
gatgatgtgg ttgccttaat taagggccg aagggcagta agttcgtct ggaaattta      960
cctgctggta agggaccaa gacccgtact gtaacgttga cccgtgaacg tattcgtctc    1020
gaagaccgcg cggttaaaat gtcggtgaag accgtcggta agagaaagt cggcgtgctg    1080
gatattccgg gcttctatgt gggtttgaca gacgatgtca aagtgcaact gcagaaactg    1140
gaaaaacaga atgtcagcag cgtcatcatc gacctgcgta gcaatggcgg tggggcgtta    1200
actgaagccg tatcgctctc cggtctgtt attcctgcgg gtcccattgt tcaggtccgc    1260
gataacaacg gcaaggttcg tgaagatagc gataccgacg gacaggtttt ctataaaggc    1320
ccgctggtgg tgctggttga ccgcttcagt gcttcggctt cagaaatctt tgccgcggca    1380
atgcaggatt acggtcgtgc gctggttgtg ggtgaaccga cgtttggtaa aggcaccgtt    1440
cagcaatacc gttcattgaa ccgtatttac gatcagatgt tacgtcctga atggccagcg    1500
ctgggttctg tgcagtacac gatccagaaa ttctatcgcg ttaacggcgg cagtacgcaa    1560
cgtaaaggcg taacgccaga catcatcatg ccgacgggta atgaagaaac ggaaacgggt    1620
gagaaattcg aagataacgc gctgccgtgg gatagcattg atgccgcgac ttatgtgaaa    1680
tcaggagatt taacggcctt tgaaccggag ctgctgaagg aacataatgc gcgtatcgcg    1740
aaagatcctg agttccagaa catcatgaag gatatcgcgc gcttcaacgc tatgaaggac    1800
aagcgcaata tcgtttctct gaattacgct gtgcgtgaga aagagaataa tgaagatgat    1860
gcgacgcgtc tggcgcgttt gaacgaacgc tttaaacgcg aaggtaaacc ggagttgaag    1920
aaactggatg atctaccgaa agattaccag gagccggatc cttatctgga tgagacggtg    1980
aatatcgcac tcgatctggc gaagcttgaa aaagccagac ccgcggaaca acccgctccc    2040
gtcaagtaa                                                            2049
```

<210> SEQ ID NO 2
<211> LENGTH: 680
<212> TYPE: PRT
<213> ORGANISM: Escherichia coli

<400> SEQUENCE: 2

```
Met Phe Phe Arg Leu Thr Ala Leu Ala Gly Leu Leu Ala Ile Ala Gly
1               5                   10                  15
Gln Thr Phe Ala Val Glu Asp Ile Thr Arg Ala Asp Gln Ile Pro Val
            20                  25                  30
Leu Lys Glu Glu Thr Gln His Ala Thr Val Ser Glu Arg Val Thr Ser
        35                  40                  45
Arg Phe Thr Arg Ser His Tyr Arg Gln Phe Asp Leu Asp Gln Ala Phe
    50                  55                  60
Ser Ala Lys Ile Phe Asp Arg Tyr Leu Asn Leu Leu Asp Tyr Ser His
65                  70                  75                  80
Asn Val Leu Leu Ala Ser Asp Val Glu Gln Phe Ala Lys Lys Lys Thr
                85                  90                  95
Glu Leu Gly Asp Glu Leu Arg Ser Gly Lys Leu Asp Val Phe Tyr Asp
            100                 105                 110
Leu Tyr Asn Leu Ala Gln Lys Arg Arg Phe Glu Arg Tyr Gln Tyr Ala
        115                 120                 125
Leu Ser Val Leu Glu Lys Pro Met Asp Phe Thr Gly Asn Asp Thr Tyr
    130                 135                 140
Asn Leu Asp Arg Ser Lys Ala Pro Trp Pro Lys Asn Glu Ala Glu Leu
145                 150                 155                 160
Asn Ala Leu Trp Asp Ser Lys Val Lys Phe Asp Glu Leu Ser Leu Lys
                165                 170                 175
Leu Thr Gly Lys Thr Asp Lys Glu Ile Arg Glu Thr Leu Thr Arg Arg
            180                 185                 190
Tyr Lys Phe Ala Ile Arg Arg Leu Ala Gln Thr Asn Ser Glu Asp Val
        195                 200                 205
Phe Ser Leu Ala Met Thr Ala Phe Ala Arg Glu Ile Asp Pro His Thr
    210                 215                 220
Asn Tyr Leu Ser Pro Arg Asn Thr Glu Gln Phe Asn Thr Glu Met Ser
225                 230                 235                 240
Leu Ser Leu Glu Gly Ile Gly Ala Val Leu Gln Met Asp Asp Asp Tyr
                245                 250                 255
Thr Val Ile Asn Ser Met Val Ala Gly Gly Pro Ala Ala Lys Ser Lys
            260                 265                 270
Ala Ile Ser Val Gly Asp Lys Ile Val Gly Val Gly Gln Thr Gly Lys
        275                 280                 285
Pro Met Val Asp Val Ile Gly Trp Arg Leu Asp Asp Val Val Ala Leu
    290                 295                 300
Ile Lys Gly Pro Lys Gly Ser Lys Val Arg Leu Glu Ile Leu Pro Ala
305                 310                 315                 320
Gly Lys Gly Thr Lys Thr Arg Thr Val Thr Leu Thr Arg Glu Arg Ile
                325                 330                 335
Arg Leu Glu Asp Arg Ala Val Lys Met Ser Val Lys Thr Val Gly Lys
            340                 345                 350
Glu Lys Val Gly Val Leu Asp Ile Pro Gly Phe Tyr Val Gly Leu Thr
        355                 360                 365
Asp Asp Val Lys Val Gln Leu Gln Lys Leu Glu Lys Gln Asn Val Ser
    370                 375                 380
Ser Val Ile Ile Asp Leu Arg Ser Asn Gly Gly Gly Ala Leu Thr Glu
385                 390                 395                 400
Ala Val Ser Leu Ser Gly Leu Phe Ile Pro Ala Gly Pro Ile Val Gln
                405                 410                 415
```

-continued

```
Val Arg Asp Asn Asn Gly Lys Val Arg Glu Asp Ser Asp Thr Asp Gly
                420                 425                 430
Gln Val Phe Tyr Lys Gly Pro Leu Val Val Leu Val Asp Arg Phe Ser
            435                 440                 445
Ala Ser Ala Ser Glu Ile Phe Ala Ala Met Gln Asp Tyr Gly Arg
        450                 455                 460
Ala Leu Val Val Gly Glu Pro Thr Phe Gly Lys Gly Thr Val Gln Gln
465                 470                 475                 480
Tyr Arg Ser Leu Asn Arg Ile Tyr Asp Gln Met Leu Arg Pro Glu Trp
                485                 490                 495
Pro Ala Leu Gly Ser Val Gln Tyr Thr Ile Gln Lys Phe Tyr Arg Val
            500                 505                 510
Asn Gly Gly Ser Thr Gln Arg Lys Gly Val Thr Pro Asp Ile Ile Met
        515                 520                 525
Pro Thr Gly Asn Glu Glu Thr Glu Thr Gly Glu Lys Phe Glu Asp Asn
        530                 535                 540
Ala Leu Pro Trp Asp Ser Ile Asp Ala Ala Thr Tyr Val Lys Ser Gly
545                 550                 555                 560
Asp Leu Thr Ala Phe Glu Pro Glu Leu Leu Lys Glu His Asn Ala Arg
                565                 570                 575
Ile Ala Lys Asp Pro Glu Phe Gln Asn Ile Met Lys Asp Ile Ala Arg
            580                 585                 590
Phe Asn Ala Met Lys Asp Lys Arg Asn Ile Val Ser Leu Asn Tyr Ala
                595                 600                 605
Val Arg Glu Lys Glu Asn Asn Glu Asp Asp Ala Thr Arg Leu Ala Arg
            610                 615                 620
Leu Asn Glu Arg Phe Lys Arg Glu Gly Lys Pro Glu Leu Lys Lys Leu
625                 630                 635                 640
Asp Asp Leu Pro Lys Asp Tyr Gln Glu Pro Asp Pro Tyr Leu Asp Glu
                645                 650                 655
Thr Val Asn Ile Ala Leu Asp Leu Ala Lys Leu Glu Lys Ala Arg Pro
            660                 665                 670
Ala Glu Gln Pro Ala Pro Val Lys
        675                 680
```

<210> SEQ ID NO 3
<211> LENGTH: 2048
<212> TYPE: DNA
<213> ORGANISM: Artificial Sequence
<220> FEATURE:
<223> OTHER INFORMATION: mutated knockout Tsp gene

<400> SEQUENCE: 3

```
atgaattcgt ttttaggctt accgcgttag ctggcctgct tgcaatagca ggccagacat    60
taattgtaga agatatcacg cgtgctgatc aaattccggt attaaaggaa gagacgcagc   120
atgcgacggt aagtgagcgc gtaacgtcgc gcttcacccg ttctcattat cgccagttcg   180
acctcgatca ggcattttcg gccaaaatct tgaccgcta cctgaatctg ctcgattaca   240
gccacaacgt gctgctggca agcgatgttg aacagttcgc gaaaaagaaa accgagttag   300
gcgatgaact gcgttcaggc aaactcgacg ttttctacga tctctacaat ctggcgcaaa   360
agcgccgttt tgagcgttac cagtacgctt tgtcggtact ggaaaagccg atggatttca   420
ccggcaacga cacttataac cttgaccgca gcaaagcgcc ctggccgaaa acgaggctg   480
agttgaacgc gctgtgggac agtaaagtca aattcgacga gttaagcctg aagctgacag   540
```

```
gaaaaacgga taagaaatt cgtgaaaccc tgactcgccg ctacaaattt gccattcgtc      600
gtctggcgca aaccaacagc gaagatgttt tctcgctggc aatgacggcg tttgcgcgtg      660
aaatcgaccc gcataccaac tatctttccc cgcgtaatac cgaacagttc aacactgaaa      720
tgagtttgtc gctggaaggt attggcgcag tgctgcaaat ggatgatgac tacaccgtta      780
tcaattcgat ggtggcaggt ggtccggcag cgaagagtaa agctatcagc gttggtgaca      840
aaattgtcgg tgttggtcaa acaggcaagc cgatggttga cgtgattggc tggcgtcttg      900
atgatgtggt tgccttaatt aaagggccga agggcagtaa agttcgtctg gaaattttac      960
ctgctggtaa agggaccaag acccgtactg taacgttgac ccgtgaacgt attcgtctcg     1020
aagaccgcgc ggttaaaatg tcggtgaaga ccgtcggtaa agagaaagtc ggcgtgctgg     1080
atattccggg cttctatgtg ggtttgacag acgatgtcaa agtgcaactg cagaaactgg     1140
aaaaacagaa tgtcagcagc gtcatcatcg acctgcgtag caatggcggt ggggcgttaa     1200
ctgaagccgt atcgctctcc ggtctgtttta ttcctgcggg tcccattgtt caggtccgcg     1260
ataacaacgg caaggttcgt gaagatagcg ataccgacgg acaggttttc tataaaggcc     1320
cgctggtggt gctggttgac cgcttcagtg cttcggcttc agaaatcttt gccgcggcaa     1380
tgcaggatta cggtcgtgcg ctggttgtgg gtgaaccgac gtttggtaaa ggcaccgttc     1440
agcaataccg ttcattgaac cgtatttacg atcagatgtt acgtcctgaa tggccagcgc     1500
tgggttctgt gcagtacacg atccagaaat ctatcgcgt taacggcggc agtacgcaac     1560
gtaaaggcgt aacgccagac atcatcatgc cgacgggtaa tgaagaaacg gaaacgggtg     1620
agaaattcga agataacgcg ctgccgtggg atagcattga tgccgcgact tatgtgaaat     1680
caggagattt aacggccttt gaaccggagc tgctgaagga acataatgcg cgtatcgcga     1740
aagatcctga gttccagaac atcatgaagg atatcgcgcg cttcaacgct atgaaggaca     1800
agcgcaatat cgtttctctg aattacgctg tgcgtgagaa agagaataat gaagatgatg     1860
cgacgcgtct ggcgcgtttg aacgaacgct ttaaacgcga aggtaaaccg gagttgaaga     1920
aactggatga tctaccgaaa gattaccagg agccggatcc ttatctggat gagacggtga     1980
atatcgcact cgatctggcg aagcttgaaa aagccagacc cgcggaacaa cccgctcccg     2040
tcaagtaa                                                              2048
```

<210> SEQ ID NO 4
<211> LENGTH: 2889
<212> TYPE: DNA
<213> ORGANISM: Escherichia coli

<400> SEQUENCE: 4

```
atgccccgca gcacctggtt caaagcatta ttgttgttag ttgcccttg ggcaccctta       60 agtcaggcag aaacgggatg gcagccgatt caggaaacca tccgtaaaag tgataaagat      120
aaccgccagt atcaggctat acgtctggat aacggtatgg tggtcttgct ggtttctgat      180
ccgcaggcag ttaaatcgct ctcggcgctg gtggtgcccg ttgggtcgct ggaagatccc      240
gaggcgtacc aggggctggc acattacctt gaacatatga gtctgatggg gtcgaaaaag      300
tacccgcagg ctgacagtct ggccgaatat ctcaaaatgc acggcggtag tcacaatgcc      360
agcactgcgc cgtatcgcac ggcttttctat ctggaagttg agaacgacgc cttgcctggt      420
gcggtagacc gcctggccga tgctattgct gaacctttgc tcgacaagaa atatgccgaa      480
cgtgagcgta tgcggtgaa cgctgaatta accatgcgc gtacgcgtga cgggatgcgc      540
atggcacagg tcagcgcaga aaccattaac ccggcacacc ccggttcaaa gttttctggt      600
```

```
ggtaacctcg aaactttaag cgacaaacct ggtaatccgg tgcagcaggc gctgaaagat      660
ttccacgaga agtactattc cgccaatttg atgaaggcgg ttatttacag taataaaccg      720
ctgccggagt tggcaaaaat ggcggcggac acctttggtc gcgtgccgaa caaagagagc      780
aaaaaaccgg aaatcaccgt gccggtagtc accgacgcgc aaaagggcat tatcattcat      840
tacgtccctg cgctgccgcg taaagtgttg cgcgttgagt ttcgcatcga taacaactca      900
gcgaagttcc gtagtaaaac cgatgaattg attacctatc tgattggcaa tcgcagccca      960
ggtacacttt ctgactggct gcaaaagcag ggattagttg agggcattag cgccaactcc     1020
gatcctatcg tcaacggcaa cagcggcgta ttagcgatct ctgcgtcttt aaccgataaa     1080
ggcctggcta atcgcgatca ggttgtggcg gcaattttta gctatctcaa tctgttacgt     1140
gaaaaaggca ttgataaaca atacttcgat gaactggcga atgtgctgga tatcgacttc     1200
cgttatccgt cgatcacccg tgatatggat tacgtcgaat ggctggcaga taccatgatt     1260
cgcgttcctg ttgagcatac gctggatgca gtcaatattg ccgatcggta cgatgctaaa     1320
gcagtaaagg aacgtctggc gatgatgacg ccgcagaatg cgcgtatctg gtatatcagc     1380
ccgaaagagc gcacaacaa aacgcttac tttgtcgatg cgccgtatca ggtcgataaa      1440
atcagcgcac aaactttcgc cgactggcag aaaaaagccg ccgacattgc gctctctttg     1500
ccagagctta acccttatat tcctgatgat ttctcgctga ttaagtcaga gaagaaatac     1560
gaccatccag agctgattgt tgatgagtcg aatctgcgcg tggtgtatgc gccaagccgt     1620
tattttgcca gcgagcccaa agctgatgtc agcctgattt tgcgtaatcc gaaagccatg     1680
gacagcgccc gcaatcaggt gatgtttgcg ctcaatgatt atctcgcagg gctggcgctt     1740
gatcagttaa gcaaccaggc gtcggttggt ggcataagtt tttccaccaa cgctaacaac     1800
ggccttatgg ttaatgctaa tggttacacc cagcgtctgc cgcagctgtt ccaggcattg     1860
ctcgaggggt actttagcta taccgctacg gaagatcagc ttgagcaggc gaagtcctgg     1920
tataaccaga tgatggattc cgcagaaaag ggtaaagcgt ttgagcaggc gattatgccc     1980
gcgcagatgc tctcgcaagt gccgtacttc tcgcgagatg aacggcgtaa aattttgccc     2040
tccattacgt tgaaagaggt gctggcctat cgcgacgcct taaaatcagg ggctcgacca     2100
gagtttatgg ttatcggcaa catgaccgag gcccaggcaa caacgctggc acgcgatgtg     2160
caaaaacagt gggcgctga tggttcagag tggtgtcgaa acaaagatgt agtggtcgat      2220
aaaaaacaat ccgtcatctt tgaaaaagcc ggtaacagca ccgactccgc actggcagcg     2280
gtatttgtac cgactggcta cgatgaatac accagctcag cctatagctc tctgttgggg     2340
cagatcgtac agccgtggtt ctacaatcag ttgcgtaccg aagaacaatt gggctatgcc     2400
gtgtttgcgt ttccaatgag cgtggggcgt cagtgggcga tgggcttcct tttgcaaagc     2460
aatgataaac agccttcatt cttgtgggag cgttacaagg cgttttttccc aaccgcagag     2520 gcaaaattgc gagcgatgaa gccagatgag tttgcgcaaa tccagcaggc ggtaattacc     2580
cagatgctgc aggcaccgca aacgctcggc gaagaagcat cgaagttaag taaagatttc     2640
gatcgcggca atatgcgctt cgattcgcgt gataaaatcg tggcccagat aaaactgctg     2700
acgccgcaaa aacttgctga tttcttccat caggcggtgg tcgagccgca aggcatggct     2760
attctgtcgc agatttccgg cagccagaac gggaaagccg aatatgtaca ccctgaaggc     2820
tggaaagtgt gggagaacgt cagcgcgttg cagcaaacaa tgcccctgat gagtgaaaag     2880
aatgagtga                                                            2889
```

<210> SEQ ID NO 5
<211> LENGTH: 962
<212> TYPE: PRT
<213> ORGANISM: Escherichia coli

<400> SEQUENCE: 5

Met Pro Arg Ser Thr Trp Phe Lys Ala Leu Leu Leu Val Ala Leu
1               5                   10                  15

Trp Ala Pro Leu Ser Gln Ala Glu Thr Gly Trp Gln Pro Ile Gln Glu
            20                  25                  30

Thr Ile Arg Lys Ser Asp Lys Asp Asn Arg Gln Tyr Gln Ala Ile Arg
            35                  40                  45

Leu Asp Asn Gly Met Val Val Leu Val Ser Asp Pro Gln Ala Val
50                  55                  60

Lys Ser Leu Ser Ala Leu Val Val Pro Val Gly Ser Leu Glu Asp Pro
65                  70                  75                  80

Glu Ala Tyr Gln Gly Leu Ala His Tyr Leu Glu His Met Ser Leu Met
                    85                  90                  95

Gly Ser Lys Lys Tyr Pro Gln Ala Asp Ser Leu Ala Glu Tyr Leu Lys
                100                 105                 110

Met His Gly Gly Ser His Asn Ala Ser Thr Ala Pro Tyr Arg Thr Ala
            115                 120                 125

Phe Tyr Leu Glu Val Glu Asn Asp Ala Leu Pro Gly Ala Val Asp Arg
130                 135                 140

Leu Ala Asp Ala Ile Ala Glu Pro Leu Leu Asp Lys Lys Tyr Ala Glu
145                 150                 155                 160

Arg Glu Arg Asn Ala Val Asn Ala Glu Leu Thr Met Ala Arg Thr Arg
                165                 170                 175

Asp Gly Met Arg Met Ala Gln Val Ser Ala Glu Thr Ile Asn Pro Ala
            180                 185                 190

His Pro Gly Ser Lys Phe Ser Gly Gly Asn Leu Glu Thr Leu Ser Asp
            195                 200                 205

Lys Pro Gly Asn Pro Val Gln Gln Ala Leu Lys Asp Phe His Glu Lys
210                 215                 220

Tyr Tyr Ser Ala Asn Leu Met Lys Ala Val Ile Tyr Ser Asn Lys Pro
225                 230                 235                 240

Leu Pro Glu Leu Ala Lys Met Ala Ala Asp Thr Phe Gly Arg Val Pro
                245                 250                 255

Asn Lys Glu Ser Lys Lys Pro Glu Ile Thr Val Pro Val Val Thr Asp
            260                 265                 270

Ala Gln Lys Gly Ile Ile Ile His Tyr Val Pro Ala Leu Pro Arg Lys
            275                 280                 285

Val Leu Arg Val Glu Phe Arg Ile Asp Asn Asn Ser Ala Lys Phe Arg
290                 295                 300

Ser Lys Thr Asp Glu Leu Ile Thr Tyr Leu Ile Gly Asn Arg Ser Pro
305                 310                 315                 320

Gly Thr Leu Ser Asp Trp Leu Gln Lys Gln Gly Leu Val Glu Gly Ile
                325                 330                 335

Ser Ala Asn Ser Asp Pro Ile Val Asn Gly Asn Ser Gly Val Leu Ala
            340                 345                 350

Ile Ser Ala Ser Leu Thr Asp Lys Gly Leu Ala Asn Arg Asp Gln Val
            355                 360                 365

Val Ala Ala Ile Phe Ser Tyr Leu Asn Leu Leu Arg Glu Lys Gly Ile
370                 375                 380

-continued

```
Asp Lys Gln Tyr Phe Asp Glu Leu Ala Asn Val Leu Asp Ile Asp Phe
385                 390                 395                 400

Arg Tyr Pro Ser Ile Thr Arg Asp Met Asp Tyr Val Glu Trp Leu Ala
            405                 410                 415

Asp Thr Met Ile Arg Val Pro Val Glu His Thr Leu Asp Ala Val Asn
        420                 425                 430

Ile Ala Asp Arg Tyr Asp Ala Lys Ala Val Lys Glu Arg Leu Ala Met
    435                 440                 445

Met Thr Pro Gln Asn Ala Arg Ile Trp Tyr Ile Ser Pro Lys Glu Pro
450                 455                 460

His Asn Lys Thr Ala Tyr Phe Val Asp Ala Pro Tyr Gln Val Asp Lys
465                 470                 475                 480

Ile Ser Ala Gln Thr Phe Ala Asp Trp Gln Lys Lys Ala Ala Asp Ile
            485                 490                 495

Ala Leu Ser Leu Pro Glu Leu Asn Pro Tyr Ile Pro Asp Asp Phe Ser
        500                 505                 510

Leu Ile Lys Ser Glu Lys Lys Tyr Asp His Pro Glu Leu Ile Val Asp
    515                 520                 525

Glu Ser Asn Leu Arg Val Val Tyr Ala Pro Ser Arg Tyr Phe Ala Ser
530                 535                 540

Glu Pro Lys Ala Asp Val Ser Leu Ile Leu Arg Asn Pro Lys Ala Met
545                 550                 555                 560

Asp Ser Ala Arg Asn Gln Val Met Phe Ala Leu Asn Asp Tyr Leu Ala
            565                 570                 575

Gly Leu Ala Leu Asp Gln Leu Ser Gln Ala Ser Val Gly Gly Ile
        580                 585                 590

Ser Phe Ser Thr Asn Ala Asn Asn Gly Leu Met Val Asn Ala Asn Gly
    595                 600                 605

Tyr Thr Gln Arg Leu Pro Gln Leu Phe Gln Ala Leu Leu Glu Gly Tyr
610                 615                 620

Phe Ser Tyr Thr Ala Thr Glu Asp Gln Leu Glu Gln Ala Lys Ser Trp
625                 630                 635                 640

Tyr Asn Gln Met Met Asp Ser Ala Glu Lys Gly Lys Ala Phe Glu Gln
            645                 650                 655

Ala Ile Met Pro Ala Gln Met Leu Ser Gln Val Pro Tyr Phe Ser Arg
        660                 665                 670

Asp Glu Arg Arg Lys Ile Leu Pro Ser Ile Thr Leu Lys Glu Val Leu
    675                 680                 685

Ala Tyr Arg Asp Ala Leu Lys Ser Gly Ala Arg Pro Glu Phe Met Val
690                 695                 700

Ile Gly Asn Met Thr Glu Ala Gln Ala Thr Thr Leu Ala Arg Asp Val
705                 710                 715                 720

Gln Lys Gln Leu Gly Ala Asp Gly Ser Glu Trp Cys Arg Asn Lys Asp
            725                 730                 735

Val Val Val Asp Lys Lys Gln Ser Val Ile Phe Glu Lys Ala Gly Asn
        740                 745                 750

Ser Thr Asp Ser Ala Leu Ala Ala Val Phe Val Pro Thr Gly Tyr Asp
    755                 760                 765

Glu Tyr Thr Ser Ser Ala Tyr Ser Ser Leu Leu Gly Gln Ile Val Gln
770                 775                 780

Pro Trp Phe Tyr Asn Gln Leu Arg Thr Glu Glu Gln Leu Gly Tyr Ala
785                 790                 795                 800
```

| Val | Phe | Ala | Phe | Pro | Met | Ser | Val | Gly | Arg | Gln | Trp | Gly | Met | Gly | Phe |
|---|---|---|---|---|---|---|---|---|---|---|---|---|---|---|---|
| | | | | 805 | | | | 810 | | | | | 815 | | |

| Leu | Leu | Gln | Ser | Asn | Asp | Lys | Gln | Pro | Ser | Phe | Leu | Trp | Glu | Arg | Tyr |
|---|---|---|---|---|---|---|---|---|---|---|---|---|---|---|---|
| | 820 | | | | | 825 | | | | | 830 | | | | |

| Lys | Ala | Phe | Phe | Pro | Thr | Ala | Glu | Ala | Lys | Leu | Arg | Ala | Met | Lys | Pro |
|---|---|---|---|---|---|---|---|---|---|---|---|---|---|---|---|
| | 835 | | | | | 840 | | | | | 845 | | | | |

| Asp | Glu | Phe | Ala | Gln | Ile | Gln | Gln | Ala | Val | Ile | Thr | Gln | Met | Leu | Gln |
|---|---|---|---|---|---|---|---|---|---|---|---|---|---|---|---|
| 850 | | | | | 855 | | | | | 860 | | | | | |

| Ala | Pro | Gln | Thr | Leu | Gly | Glu | Glu | Ala | Ser | Lys | Leu | Ser | Lys | Asp | Phe |
|---|---|---|---|---|---|---|---|---|---|---|---|---|---|---|---|
| 865 | | | | 870 | | | | | 875 | | | | | 880 | |

| Asp | Arg | Gly | Asn | Met | Arg | Phe | Asp | Ser | Arg | Asp | Lys | Ile | Val | Ala | Gln |
|---|---|---|---|---|---|---|---|---|---|---|---|---|---|---|---|
| | | | | 885 | | | | 890 | | | | | 895 | | |

| Ile | Lys | Leu | Leu | Thr | Pro | Gln | Lys | Leu | Ala | Asp | Phe | Phe | His | Gln | Ala |
|---|---|---|---|---|---|---|---|---|---|---|---|---|---|---|---|
| | | 900 | | | | | 905 | | | | | 910 | | | |

| Val | Val | Glu | Pro | Gln | Gly | Met | Ala | Ile | Leu | Ser | Gln | Ile | Ser | Gly | Ser |
|---|---|---|---|---|---|---|---|---|---|---|---|---|---|---|---|
| | 915 | | | | | 920 | | | | | 925 | | | | |

| Gln | Asn | Gly | Lys | Ala | Glu | Tyr | Val | His | Pro | Glu | Gly | Trp | Lys | Val | Trp |
|---|---|---|---|---|---|---|---|---|---|---|---|---|---|---|---|
| | 930 | | | | | 935 | | | | | 940 | | | | |

| Glu | Asn | Val | Ser | Ala | Leu | Gln | Gln | Thr | Met | Pro | Leu | Met | Ser | Glu | Lys |
|---|---|---|---|---|---|---|---|---|---|---|---|---|---|---|---|
| 945 | | | | | 950 | | | | | 955 | | | | | 960 |

Asn Glu

<210> SEQ ID NO 6
<211> LENGTH: 2889
<212> TYPE: DNA
<213> ORGANISM: Artificial Sequence
<220> FEATURE:
<223> OTHER INFORMATION: mutated knockout Protease III gene

<400> SEQUENCE: 6

```
attccccgca gcacctggtt caaagcatta ttgttgttag ttgccctttg ggcacattaa      60
tgtcaggcag aaacgggatg gcagccgatt caggaaacca tccgtaaaag tgataaagat     120
aaccgccagt atcaggctat acgtctggat aacggtatgg tggtcttgct ggtttctgat     180
ccgcaggcag ttaaatcgct ctcggcgctg gtggtgcccg ttgggtcgct ggaagatccc     240
gaggcgtacc aggggctggc acattacctt gaacatatga gtctgatggg gtcgaaaaag     300
tacccgcagg ctgacagtct ggccgaatat ctcaaaatgc acggcggtag tcacaatgcc     360
agcactgcgc cgtatcgcac ggcttttctat ctggaagttg agaacgacgc cttgcctggt     420
gcggtagacc gcctggccga tgctattgct gaacctttgc tcgacaagaa atatgccgaa     480
cgtgagcgta atgcggtgaa cgctgaatta accatggcgc gtacgcgtga cgggatgcgc     540
atggcacagg tcagcgcaga aaccattaac cggcacacc ccggttcaaa gttttctggt     600
ggtaacctcg aaactttaag cgacaaacct ggtaatccgg tgcagcaggc gctgaaagat     660
ttccacgaga agtactattc cgccaatttg atgaaggcgg ttatttacag taataaaccg     720
ctgccggagt tggcaaaaat ggcggcggac acctttggtc gcgtgccgaa caaagagagc     780
aaaaaaccgg aaatcaccgt gccggtagtc accgacgcgc aaaagggcat tatcattcat     840
tacgtccctg cgctgccgcg taaagtgttg cgcgttgagt ttcgcatcga taacaactca     900
gcgaagttcc gtagtaaaac cgatgaattg attacctatc tgattggcaa tcgcagccca     960
ggtacacttt ctgactggct gcaaaagcag ggattagttg agggcattag cgccaactcc    1020
gatcctatcg tcaacggcaa cagcggcgta ttagcgatct ctgcgtcttt aaccgataaa    1080
ggcctggcta atcgcgatca ggttgtggcg gcaattttta gctatctcaa tctgttacgt    1140
```

```
gaaaaaggca ttgataaaca atacttcgat gaactggcga atgtgctgga tatcgacttc    1200
cgttatccgt cgatcacccg tgatatggat tacgtcgaat ggctggcaga taccatgatt    1260
cgcgttcctg ttgagcatac gctggatgca gtcaatattg ccgatcggta cgatgctaaa    1320
gcagtaaagg aacgtctggc gatgatgacg ccgcagaatg cgcgtatctg gtatatcagc    1380
ccgaaagagc cgcacaacaa aacggcttac tttgtcgatg cgccgtatca ggtcgataaa    1440
atcagcgcac aaactttcgc cgactggcag aaaaaagccg ccgacattgc gctctctttg    1500
ccagagctta acccttatat tcctgatgat ttctcgctga ttaagtcaga agaaaatac     1560 gaccatccag agctgattgt tgatgagtcg aatctgcgcg tggtgtatgc gccaagccgt    1620
tattttgcca gcgagcccaa agctgatgtc agcctgattt tgcgtaatcc gaaagccatg    1680
gacagcgccc gcaatcaggt gatgtttgcg ctcaatgatt atctcgcagg gctggcgctt    1740
gatcagttaa gcaaccaggc gtcggttggt ggcataagtt tttccaccaa cgctaacaac    1800
ggccttatgg ttaatgctaa tggttacacc cagcgtctgc cgcagctgtt ccaggcattg    1860
ctcgaggggt actttagcta taccgctacg gaagatcagc ttgagcaggc gaagtcctgg    1920
tataaccaga tgatggattc cgcagaaaag ggtaaagcgt ttgagcaggc gattatgccc    1980
gcgcagatgc tctcgcaagt gccgtacttc tcgcgagatg aacggcgtaa aattttgccc    2040
tccattacgt tgaaagaggt gctggcctat cgcgacgcct aaaatcagg ggctcgacca     2100 gagtttatgg ttatcggcaa catgaccgag gcccaggcaa caacgctggc acgcgatgtg    2160
caaaaacagt tgggcgctga tggttcgag tggtgtcgaa acaaagatgt agtggtcgat     2220
aaaaaacaat ccgtcatctt tgaaaaagcc ggtaacagca ccgactccgc actggcagcg    2280
gtatttgtac cgactggcta cgatgaatac accagctcag cctatagctc tctgttgggg    2340
cagatcgtac agccgtggtt ctacaatcag ttgcgtaccg aagaacaatt gggctatgcc    2400
gtgtttgcgt ttccaatgag cgtggggcgt cagtggggca tgggcttcct tttgcaaagc    2460
aatgataaac agccttcatt cttgtgggag cgttacaagg cgttttttccc aaccgcagag    2520 gcaaaattgc gagcgatgaa gccagatgag tttgcgcaaa tccagcaggc ggtaattacc    2580
cagatgctgc aggcaccgca aacgctcggc gaagaagcat cgaagttaag taaagatttc    2640
gatcgcggca atatgcgctt cgattcgcgt gataaaatcg tggcccagat aaaactgctg    2700
acgccgcaaa aacttgctga tttcttccat caggcggtgg tcgagccgca aggcatggct    2760
attctgtcgc agatttccgg cagccagaac gggaaagccg aatatgtaca ccctgaaggc    2820
tggaaagtgt gggagaacgt cagcgcgttg cagcaaacaa tgcccctgat gagtgaaaag    2880
aatgagtga                                                            2889
```

<210> SEQ ID NO 7
<211> LENGTH: 1425
<212> TYPE: DNA
<213> ORGANISM: Escherichia coli

<400> SEQUENCE: 7

```
atgaaaaaaa ccacattagc actgagtgca ctggctctga gtttaggttt ggcgttatct     60
ccgctctctg caacggcggc tgagacttct tcagcaacga cagcccagca gatgccaagc    120
cttgcaccga tgctcgaaaa ggtgatgcct tcagtggtca gcattaacgt agaaggtagc    180
acaaccgtta atacgccgcg tatgccgcgt aatttccagc agttcttcgg tgatgattct    240
ccgttctgcc aggaaggttc tccgttccag agctctccgt tctgccaggg tggccagggc    300
```

```
ggtaatggtg gcggccagca acagaaattc atggcgctgg gttccggcgt catcattgat      360
gccgataaag gctatgtcgt caccaacaac cacgttgttg ataacgcgac ggtcattaaa      420
gttcaactga gcgatggccg taagttcgac gcgaagatgg ttggcaaaga tccgcgctct      480
gatatcgcgc tgatccaaat ccagaacccg aaaaacctga ccgcaattaa gatggcggat      540
tctgatgcac tgcgcgtggg tgattacacc gtagcgattg gtaacccgtt tggtctgggc      600
gagacggtaa cttccgggat tgtctctgcg ctggggcgta cgggcctgaa tgccgaaaac      660
tacgaaaact tcatccagac cgatgcagcg atcaaccgtg gtaactccgg tggtgcgctg      720
gttaacctga acggcgaact gatcggtatc aacaccgcga tcctcgcacc ggacggcggc      780
aacatcggta tcggttttgc tatcccgagt aacatggtga aaaacctgac ctcgcagatg      840
gtggaatacg gccaggtgaa acgcggtgag ctgggtatta tggggactga gctgaactcc      900
gaactggcga agcgatgaa agttgacgcc cagcgcggtg ctttcgtaag ccaggttctg      960
cctaattcct ccgctgcaaa agcgggcatt aaagcgggtg atgtgatcac ctcactgaac     1020
ggtaagccga tcagcagctt tgccgcactg cgtgctcagg tgggtactat gccggtaggc     1080
agcaaactga ccctgggctt actgcgcgac ggtaagcagg ttaacgtgaa cctggaactg     1140
cagcagagca gccagaatca ggttgattcc agctccatct tcaacggcat tgaaggcgct     1200
gagatgagca acaaaggcaa agatcagggc gtggtagtga acaacgtgaa aacgggcact     1260
ccggctgcgc agatcggcct gaagaaaggt gatgtgatta ttggcgcgaa ccagcaggca     1320
gtgaaaaaca tcgctgaact gcgtaaagtt ctcgacagca aaccgtctgt gctggcactc     1380
aacattcagc gcggcgacag caccatctac ctgttaatgc agtaa                     1425
```

<210> SEQ ID NO 8
<211> LENGTH: 474
<212> TYPE: PRT
<213> ORGANISM: Escherichia coli

<400> SEQUENCE: 8

```
Met Lys Lys Thr Thr Leu Ala Leu Ser Ala Leu Ala Leu Ser Leu Gly
1               5                   10                  15

Leu Ala Leu Ser Pro Leu Ser Ala Thr Ala Ala Glu Thr Ser Ser Ala
            20                  25                  30

Thr Thr Ala Gln Gln Met Pro Ser Leu Ala Pro Met Leu Glu Lys Val
        35                  40                  45

Met Pro Ser Val Val Ser Ile Asn Val Glu Gly Ser Thr Thr Val Asn
    50                  55                  60

Thr Pro Arg Met Pro Arg Asn Phe Gln Gln Phe Gly Asp Asp Ser
65                  70                  75                  80

Pro Phe Cys Gln Glu Gly Ser Pro Phe Gln Ser Ser Pro Phe Cys Gln
                85                  90                  95

Gly Gly Gln Gly Gly Asn Gly Gly Gln Gln Lys Phe Met Ala
            100                 105                 110

Leu Gly Ser Gly Val Ile Ile Asp Ala Asp Lys Gly Tyr Val Val Thr
        115                 120                 125

Asn Asn His Val Val Asp Asn Ala Thr Val Ile Lys Val Gln Leu Ser
    130                 135                 140

Asp Gly Arg Lys Phe Asp Ala Lys Met Val Gly Lys Asp Pro Arg Ser
145                 150                 155                 160

Asp Ile Ala Leu Ile Gln Ile Gln Asn Pro Lys Asn Leu Thr Ala Ile
                165                 170                 175
```

```
Lys Met Ala Asp Ser Asp Ala Leu Arg Val Gly Asp Tyr Thr Val Ala
            180                 185                 190
Ile Gly Asn Pro Phe Gly Leu Gly Glu Thr Val Thr Ser Gly Ile Val
        195                 200                 205
Ser Ala Leu Gly Arg Ser Gly Leu Asn Ala Glu Asn Tyr Glu Asn Phe
    210                 215                 220
Ile Gln Thr Asp Ala Ala Ile Asn Arg Gly Asn Ser Gly Gly Ala Leu
225                 230                 235                 240
Val Asn Leu Asn Gly Glu Leu Ile Gly Ile Asn Thr Ala Ile Leu Ala
                245                 250                 255
Pro Asp Gly Gly Asn Ile Gly Ile Gly Phe Ala Ile Pro Ser Asn Met
            260                 265                 270
Val Lys Asn Leu Thr Ser Gln Met Val Glu Tyr Gly Gln Val Lys Arg
        275                 280                 285
Gly Glu Leu Gly Ile Met Gly Thr Glu Leu Asn Ser Glu Leu Ala Lys
    290                 295                 300
Ala Met Lys Val Asp Ala Gln Arg Gly Ala Phe Val Ser Gln Val Leu
305                 310                 315                 320
Pro Asn Ser Ser Ala Ala Lys Ala Gly Ile Lys Ala Gly Asp Val Ile
                325                 330                 335
Thr Ser Leu Asn Gly Lys Pro Ile Ser Ser Phe Ala Ala Leu Arg Ala
            340                 345                 350
Gln Val Gly Thr Met Pro Val Gly Ser Lys Leu Thr Leu Gly Leu Leu
        355                 360                 365
Arg Asp Gly Lys Gln Val Asn Val Asn Leu Glu Leu Gln Gln Ser Ser
    370                 375                 380
Gln Asn Gln Val Asp Ser Ser Ile Phe Asn Gly Ile Glu Gly Ala
385                 390                 395                 400
Glu Met Ser Asn Lys Gly Lys Asp Gln Gly Val Val Asn Asn Val
                405                 410                 415
Lys Thr Gly Thr Pro Ala Ala Gln Ile Gly Leu Lys Lys Gly Asp Val
            420                 425                 430
Ile Ile Gly Ala Asn Gln Gln Ala Val Lys Asn Ile Ala Glu Leu Arg
        435                 440                 445
Lys Val Leu Asp Ser Lys Pro Ser Val Leu Ala Leu Asn Ile Gln Arg
    450                 455                 460
Gly Asp Ser Thr Ile Tyr Leu Leu Met Gln
465                 470

<210> SEQ ID NO 9
<211> LENGTH: 1425
<212> TYPE: DNA
<213> ORGANISM: Artificial Sequence
<220> FEATURE:
<223> OTHER INFORMATION: mutated DegP

<400> SEQUENCE: 9
atgaaaaaaa ccacattagc actgagtgca ctggctctga gtttaggttt ggcgttatct      60
ccgctctctg caacggcggc tgagacttct tcagcaacga cagcccagca gatgccaagc     120
cttgcaccga tgctcgaaaa ggtgatgcct tcagtggtca gcattaacgt agaaggtagc     180
acaaccgtta atacgccgcg tatgccgcgt aatttccagc agttcttcgg tgatgattct     240
ccgttctgcc aggaaggttc tccgttccag agctctccgt tctgccaggg tggccagggc     300
ggtaatggtg gcggccagca acagaaattc atggcgctgg gttccggcgt catcattgat     360
```

```
gccgataaag gctatgtcgt caccaacaac cacgttgttg ataacgcgac ggtcattaaa      420
gttcaactga gcgatggccg taagttcgac gcgaagatgg ttggcaaaga tccgcgctct      480
gatatcgcgc tgatccaaat ccagaacccg aaaaacctga ccgcaattaa gatggcggat      540
tctgatgcac tgcgcgtggg tgattacacc gtagcgattg gtaacccgtt tggtctgggc      600
gagacggtaa cttccgggat tgtctctgcg ctggggcgta gcggcctgaa tgccgaaaac      660
tacgaaaact tcatccagac cgatgcagcg attaatcgtg gtaacgccgg tggtgcgctg      720
gttaacctga acggcgaact gatcggtatc aacaccgcga tcctcgcacc ggacggcggc      780
aacatcggta tcggttttgc tatcccgagt aacatggtga aaacctgac ctcgcagatg       840 gtggaatacg ccaggtgaa acgcggtgag ctgggtatta tggggactga gctgaactcc       900
gaactggcga agcgatgaa agttgacgcc cagcgcggtg ctttcgtaag ccaggttctg       960
cctaattcct ccgctgcaaa gcgggcatt aaagcgggtg atgtgatcac ctcactgaac      1020
ggtaagccga tcagcagctt tgccgcactg cgtgctcagg tgggtactat gccggtaggc     1080
agcaaactga ccctgggctt actgcgcgac ggtaagcagg ttaacgtgaa cctggaactg     1140
cagcagagca gccagaatca ggttgattcc agctccatct tcaacggcat tgaaggcgct     1200
gagatgagca acaaaggcaa agatcagggc gtggtagtga acaacgtgaa aacgggcact     1260
ccggctgcgc agatcggcct gaagaaaggt gatgtgatta ttggcgcgaa ccagcaggca     1320
gtgaaaaaca tcgctgaact gcgtaaagtt ctcgacagca accgtctgt gctggcactc      1380 aacattcagc gcggcgacag caccatctac ctgttaatgc agtaa                      1425

<210> SEQ ID NO 10
<211> LENGTH: 474
<212> TYPE: PRT
<213> ORGANISM: Artificial Sequence
<220> FEATURE:
<223> OTHER INFORMATION: mutated DegP

<400> SEQUENCE: 10

Met Lys Lys Thr Thr Leu Ala Leu Ser Ala Leu Ala Leu Ser Leu Gly
1               5                   10                  15

Leu Ala Leu Ser Pro Leu Ser Ala Thr Ala Ala Glu Thr Ser Ser Ala
                20                  25                  30

Thr Thr Ala Gln Gln Met Pro Ser Leu Ala Pro Met Leu Glu Lys Val
            35                  40                  45

Met Pro Ser Val Val Ser Ile Asn Val Glu Gly Ser Thr Thr Val Asn
        50                  55                  60

Thr Pro Arg Met Pro Arg Asn Phe Gln Gln Phe Gly Asp Asp Ser
65                  70                  75                  80

Pro Phe Cys Gln Glu Gly Ser Pro Phe Gln Ser Ser Pro Phe Cys Gln
                85                  90                  95

Gly Gly Gln Gly Gly Asn Gly Gly Gln Gln Gln Lys Phe Met Ala
                100                 105                 110

Leu Gly Ser Gly Val Ile Ile Asp Ala Asp Lys Gly Tyr Val Val Thr
            115                 120                 125

Asn Asn His Val Val Asp Asn Ala Thr Val Ile Lys Val Gln Leu Ser
        130                 135                 140

Asp Gly Arg Lys Phe Asp Ala Lys Met Val Gly Lys Asp Pro Arg Ser
145                 150                 155                 160

Asp Ile Ala Leu Ile Gln Ile Gln Asn Pro Lys Asn Leu Thr Ala Ile
                165                 170                 175
```

Lys Met Ala Asp Ser Asp Ala Leu Arg Val Gly Asp Tyr Thr Val Ala
            180                 185                 190

Ile Gly Asn Pro Phe Gly Leu Gly Glu Thr Val Thr Ser Gly Ile Val
            195                 200                 205

Ser Ala Leu Gly Arg Ser Gly Leu Asn Ala Glu Asn Tyr Glu Asn Phe
210                 215                 220

Ile Gln Thr Asp Ala Ala Ile Asn Arg Gly Asn Ala Gly Gly Ala Leu
225                 230                 235                 240

Val Asn Leu Asn Gly Glu Leu Ile Gly Ile Asn Thr Ala Ile Leu Ala
            245                 250                 255

Pro Asp Gly Gly Asn Ile Gly Ile Gly Phe Ala Ile Pro Ser Asn Met
            260                 265                 270

Val Lys Asn Leu Thr Ser Gln Met Val Glu Tyr Gly Gln Val Lys Arg
            275                 280                 285

Gly Glu Leu Gly Ile Met Gly Thr Glu Leu Asn Ser Glu Leu Ala Lys
            290                 295                 300

Ala Met Lys Val Asp Ala Gln Arg Gly Ala Phe Val Ser Gln Val Leu
305                 310                 315                 320

Pro Asn Ser Ser Ala Ala Lys Ala Gly Ile Lys Ala Gly Asp Val Ile
                325                 330                 335

Thr Ser Leu Asn Gly Lys Pro Ile Ser Ser Phe Ala Ala Leu Arg Ala
            340                 345                 350

Gln Val Gly Thr Met Pro Val Gly Ser Lys Leu Thr Leu Gly Leu Leu
            355                 360                 365

Arg Asp Gly Lys Gln Val Asn Val Asn Leu Glu Leu Gln Gln Ser Ser
370                 375                 380

Gln Asn Gln Val Asp Ser Ser Ser Ile Phe Asn Gly Ile Glu Gly Ala
385                 390                 395                 400

Glu Met Ser Asn Lys Gly Lys Asp Gln Gly Val Val Asn Asn Val
                405                 410                 415

Lys Thr Gly Thr Pro Ala Ala Gln Ile Gly Leu Lys Lys Gly Asp Val
            420                 425                 430

Ile Ile Gly Ala Asn Gln Gln Ala Val Lys Asn Ile Ala Glu Leu Arg
            435                 440                 445

Lys Val Leu Asp Ser Lys Pro Ser Val Leu Ala Leu Asn Ile Gln Arg
450                 455                 460

Gly Asp Ser Thr Ile Tyr Leu Leu Met Gln
465                 470

<210> SEQ ID NO 11
<211> LENGTH: 24
<212> TYPE: DNA
<213> ORGANISM: Artificial Sequence
<220> FEATURE:
<223> OTHER INFORMATION: 5' oligonucleotide primer for the region of the
    mutated DegP gene comprising the Ase I restriction site

<400> SEQUENCE: 11
ctgcctgcga ttttcgccgg aacg                                          24

<210> SEQ ID NO 12
<211> LENGTH: 24
<212> TYPE: DNA
<213> ORGANISM: Artificial Sequence
<220> FEATURE:
<223> OTHER INFORMATION: 3' oligonucleotide primer for the region of the
    mutated DegP gene comprising the Ase I restriction site

<400> SEQUENCE: 12
cgcatggtac gtgccacgat atcc                                          24

<210> SEQ ID NO 13
<211> LENGTH: 24
<212> TYPE: DNA
<213> ORGANISM: Artificial Sequence
<220> FEATURE:
<223> OTHER INFORMATION: the 5' oligonucleotide primer for the region of
      the mutated Tsp gene comprising the Ase I restriction site

<400> SEQUENCE: 13
gggaaatgaa cctgagcaaa acgc                                          24

<210> SEQ ID NO 14
<211> LENGTH: 24
<212> TYPE: DNA
<213> ORGANISM: Artificial Sequence
<220> FEATURE:
<223> OTHER INFORMATION: 3' oligonucleotide primer for the region of the
      mutated Protease III gene comprising the Ase I restriction site

<400> SEQUENCE: 14
gggaaaggcg gcggaaccgc ctag                                          24

<210> SEQ ID NO 15
<211> LENGTH: 24
<212> TYPE: DNA
<213> ORGANISM: Artificial Sequence
<220> FEATURE:
<223> OTHER INFORMATION: 5' oligonucleotide primer for the region of the
      mutated Protease III gene comprising the Ase I restriction site

<400> SEQUENCE: 15
ctactgtgcc agcggtggta atgg                                          24

<210> SEQ ID NO 16
<211> LENGTH: 24
<212> TYPE: DNA
<213> ORGANISM: Artificial Sequence
<220> FEATURE:
<223> OTHER INFORMATION: 3' oligonucleotide primer for the region of the
      mutated Tsp gene comprising the Ase I restriction site

<400> SEQUENCE: 16
gcatcataat tttctttta cctc                                           24

<210> SEQ ID NO 17
<211> LENGTH: 564
<212> TYPE: DNA
<213> ORGANISM: Artificial Sequence
<220> FEATURE:
<223> OTHER INFORMATION: wild-type spr gene

<400> SEQUENCE: 17
atggtcaaat ctcaaccgat tttgagatat atcttgcgcg ggattcccgc gattgcagta      60
gcggttctgc tttctgcatg tagtgcaaat aacaccgcaa agaatatgca tcctgagaca     120
cgtgcagtgg gtagtgaaac atcatcactg caagcttctc aggatgaatt tgaaaacctg    180
gttcgtaatg tcgacgtaaa atcgcgaatt atggatcagt atgctgactg gaaaggcgta    240
cgttatcgtc tgggcggcag cactaaaaaa ggtatcgatt gttctggttt cgtacagcgt    300
acattccgtg agcaatttgg cttagaactt ccgcgttcga cttacgaaca gcaggaaatg    360
ggtaaatctg tttcccgcag taatttgcgt acgggtgatt tagttctgtt ccgtgccggt    420

```
tcaacgggac gccatgtcgg tatttatatc ggcaacaatc agtttgtcca tgcttccacc    480
agcagtggtg ttattatttc cagcatgaat gaaccgtact ggaagaagcg ttacaacgaa    540
gcacgccggg ttctcagccg cagc                                           564
```

<210> SEQ ID NO 18
<211> LENGTH: 188
<212> TYPE: PRT
<213> ORGANISM: Escherichia coli

<400> SEQUENCE: 18

```
Met Val Lys Ser Gln Pro Ile Leu Arg Tyr Ile Leu Arg Gly Ile Pro
1               5                   10                  15

Ala Ile Ala Val Ala Val Leu Leu Ser Ala Cys Ser Ala Asn Asn Thr
            20                  25                  30

Ala Lys Asn Met His Pro Glu Thr Arg Ala Val Gly Ser Glu Thr Ser
        35                  40                  45

Ser Leu Gln Ala Ser Gln Asp Glu Phe Glu Asn Leu Val Arg Asn Val
    50                  55                  60

Asp Val Lys Ser Arg Ile Met Asp Gln Tyr Ala Asp Trp Lys Gly Val
65                  70                  75                  80

Arg Tyr Arg Leu Gly Gly Ser Thr Lys Lys Gly Ile Asp Cys Ser Gly
                85                  90                  95

Phe Val Gln Arg Thr Phe Arg Glu Gln Phe Gly Leu Glu Leu Pro Arg
            100                 105                 110

Ser Thr Tyr Glu Gln Gln Glu Met Gly Lys Ser Val Ser Arg Ser Asn
        115                 120                 125

Leu Arg Thr Gly Asp Leu Val Leu Phe Arg Ala Gly Ser Thr Gly Arg
    130                 135                 140

His Val Gly Ile Tyr Ile Gly Asn Asn Gln Phe Val His Ala Ser Thr
145                 150                 155                 160

Ser Ser Gly Val Ile Ile Ser Ser Met Asn Glu Pro Tyr Trp Lys Lys
                165                 170                 175

Arg Tyr Asn Glu Ala Arg Arg Val Leu Ser Arg Ser
            180                 185
```

<210> SEQ ID NO 19
<211> LENGTH: 162
<212> TYPE: PRT
<213> ORGANISM: Escherichia coli

<400> SEQUENCE: 19

```
Cys Ser Ala Asn Asn Thr Ala Lys Asn Met His Pro Glu Thr Arg Ala
1               5                   10                  15

Val Gly Ser Glu Thr Ser Ser Leu Gln Ala Ser Gln Asp Glu Phe Glu
            20                  25                  30

Asn Leu Val Arg Asn Val Asp Val Lys Ser Arg Ile Met Asp Gln Tyr
        35                  40                  45

Ala Asp Trp Lys Gly Val Arg Tyr Arg Leu Gly Gly Ser Thr Lys Lys
    50                  55                  60

Gly Ile Asp Cys Ser Gly Phe Val Gln Arg Thr Phe Arg Glu Gln Phe
65                  70                  75                  80

Gly Leu Glu Leu Pro Arg Ser Thr Tyr Glu Gln Gln Glu Met Gly Lys
                85                  90                  95

Ser Val Ser Arg Ser Asn Leu Arg Thr Gly Asp Leu Val Leu Phe Arg
            100                 105                 110
```

```
Ala Gly Ser Thr Gly Arg His Val Gly Ile Tyr Ile Gly Asn Asn Gln
        115                 120                 125

Phe Val His Ala Ser Thr Ser Ser Gly Val Ile Ile Ser Ser Met Asn
    130                 135                 140

Glu Pro Tyr Trp Lys Lys Arg Tyr Asn Glu Ala Arg Arg Val Leu Ser
145                 150                 155                 160

Arg Ser

<210> SEQ ID NO 20
<211> LENGTH: 954
<212> TYPE: DNA
<213> ORGANISM: Artificial Sequence
<220> FEATURE:
<223> OTHER INFORMATION: nucleotide sequence of a mutated OmpT sequence
      comprising D210A and H212A mutations

<400> SEQUENCE: 20
atgcgggcga aacttctggg aatagtcctg acaaccccta ttgcgatcag ctcttttgct      60
tctaccgaga ctttatcgtt tactcctgac aacataaatg cggacattag tcttggaact    120
ctgagcggaa aaacaaaaga gcgtgtttat ctagccgaag aaggaggccg aaaagtcagt    180
caactcgact ggaaattcaa taacgctgca attattaaag gtgcaattaa ttgggatttg    240
atgccccaga tatctatcgg ggctgctggc tggacaactc tcggcagccg aggtggcaat    300
atggtcgatc aggactggat ggattccagt aaccccggaa cctggacgga tgaaagtaga    360 cacccctgata cacaactcaa ttatgccaac gaatttgatc tgaatatcaa aggctggctc    420
ctcaacgaac ccaattaccg cctgggactc atggccggat atcaggaaag ccgttatagc    480
tttacagcca gaggtggttc ctatatctac agttctgagg agggattcag agatgatatc    540
ggctccttcc gaatggagaa agagcaatc ggctacaaac aacgttttaa aatgccctac    600
attggcttga ctggaagtta tcgttatgaa gattttgaac tcggtggcac atttaaatac    660
agcggctggg tggaatcatc tgataacgct gaagcttatg acccgggaaa aagaatcact    720
tatcgcagta aggtcaaaga ccaaaattac tattctgttg cagtcaatgc aggttattac    780
gtcacaccta acgcaaaagt ttatgttgaa ggcgcatgga atcgggttac gaataaaaaa    840
ggtaatactt cactttatga tcacaataat aacacttcag actacagcaa aaatggagca    900
ggtatagaaa actataactt catcactact gctggtctta gtacacatt ttaa           954

<210> SEQ ID NO 21
<211> LENGTH: 317
<212> TYPE: PRT
<213> ORGANISM: Artificial Sequence
<220> FEATURE:
<223> OTHER INFORMATION: mutated OmpT sequence comprising D210A and
      H212A mutations

<400> SEQUENCE: 21

Met Arg Ala Lys Leu Leu Gly Ile Val Leu Thr Thr Pro Ile Ala Ile
1               5                   10                  15

Ser Ser Phe Ala Ser Thr Glu Thr Leu Ser Phe Thr Pro Asp Asn Ile
            20                  25                  30

Asn Ala Asp Ile Ser Leu Gly Thr Leu Ser Gly Lys Thr Lys Glu Arg
        35                  40                  45

Val Tyr Leu Ala Glu Glu Gly Gly Arg Lys Val Ser Gln Leu Asp Trp
    50                  55                  60

Lys Phe Asn Asn Ala Ala Ile Ile Lys Gly Ala Ile Asn Trp Asp Leu
```

```
        65                  70                  75                  80
Met Pro Gln Ile Ser Ile Gly Ala Ala Gly Trp Thr Thr Leu Gly Ser
                85                  90                  95

Arg Gly Gly Asn Met Val Asp Gln Asp Trp Met Asp Ser Ser Asn Pro
            100                 105                 110

Gly Thr Trp Thr Asp Glu Ser Arg His Pro Asp Thr Gln Leu Asn Tyr
        115                 120                 125

Ala Asn Glu Phe Asp Leu Asn Ile Lys Gly Trp Leu Leu Asn Glu Pro
    130                 135                 140

Asn Tyr Arg Leu Gly Leu Met Ala Gly Tyr Gln Glu Ser Arg Tyr Ser
145                 150                 155                 160

Phe Thr Ala Arg Gly Gly Ser Tyr Ile Tyr Ser Ser Glu Glu Gly Phe
                165                 170                 175

Arg Asp Asp Ile Gly Ser Phe Pro Asn Gly Glu Arg Ala Ile Gly Tyr
            180                 185                 190

Lys Gln Arg Phe Lys Met Pro Tyr Ile Gly Leu Thr Gly Ser Tyr Arg
        195                 200                 205

Tyr Glu Asp Phe Glu Leu Gly Gly Thr Phe Lys Tyr Ser Gly Trp Val
    210                 215                 220

Glu Ser Ser Asp Asn Ala Glu Ala Tyr Asp Pro Gly Lys Arg Ile Thr
225                 230                 235                 240

Tyr Arg Ser Lys Val Lys Asp Gln Asn Tyr Tyr Ser Val Ala Val Asn
                245                 250                 255

Ala Gly Tyr Tyr Val Thr Pro Asn Ala Lys Val Tyr Val Glu Gly Ala
            260                 265                 270

Trp Asn Arg Val Thr Asn Lys Lys Gly Asn Thr Ser Leu Tyr Asp His
        275                 280                 285

Asn Asn Asn Thr Ser Asp Tyr Ser Lys Asn Gly Ala Gly Ile Glu Asn
    290                 295                 300

Tyr Asn Phe Ile Thr Thr Ala Gly Leu Lys Tyr Thr Phe
305                 310                 315
```

<210> SEQ ID NO 22
<211> LENGTH: 954
<212> TYPE: DNA
<213> ORGANISM: Artificial Sequence
<220> FEATURE:
<223> OTHER INFORMATION: mutated knockout OmpT sequence

<400> SEQUENCE: 22

```
attcgggcga aacttctggg aatagtcctg acaaccccta ttgcgatcag ctcttttgct    60
tctaccgaga ctttatcgtt tactcctgac aacataaatg cggacattag tcttggaact   120
ctgagcggaa aaacaaaaga gcgtgtttat ctagccgaag aaggaggccg aaaagtcagt   180
caactcgact ggaaattcaa taacgctgca attattaaag gtgcaattaa ttgggatttg   240
atgccccaga tatctatcgg ggctgctggc tggacaactc tcggcagccg aggtggcaat   300
atggtcgatc aggactggat ggattccagt aaccccggaa cctggacgga tgaaagtaga   360
caccctgata cacaactcaa ttatgccaac gaatttgatc tgaatatcaa aggctggctc   420
ctcaacgaac ccaattaccg cctgggactc atggccggat atcaggaaag ccgttatagc   480
tttacagcca gaggtggttc ctatatctac agttctgagg agggattcag agatgatatc   540
ggctccttcc cgaatggaga aagagcaatc ggctacaaac aacgttttaa aatgccctac   600
attggcttga ctggaagtta tcgttatgaa gattttgaac tcggtggcac atttaaatac   660
```

```
agcggctggg tggaatcatc tgataacgat gaacactatg acccgggaaa aagaatcact    720
tatcgcagta aggtcaaaga ccaaaattac tattctgttg cagtcaatgc aggttattac    780
gtcacaccta acgcaaaagt ttatgttgaa ggcgcatgga atcgggttac gaataaaaaa    840
ggtaatactt cactttatga tcacaataat aacacttcag actacagcaa aaatggagca    900
ggtatagaaa actataactt catcactact gctggtctta agtacacatt ttaa           954
```

```
<210> SEQ ID NO 23
<211> LENGTH: 45
<212> TYPE: DNA
<213> ORGANISM: Artificial Sequence
<220> FEATURE:
<223> OTHER INFORMATION: OmpA oligonucleotide adapter

<400> SEQUENCE: 23
cgattgaatg gagaacttga attcgggcga aacttctggg aatag                     45

<210> SEQ ID NO 24
<211> LENGTH: 33
<212> TYPE: DNA
<213> ORGANISM: Artificial Sequence
<220> FEATURE:
<223> OTHER INFORMATION: oligonucleotide cassette encoding intergenic
      sequence 1 (IGS1) for E. coli Fab expression

<400> SEQUENCE: 24
aagttttaat agaggagagt gttaatgaag aag                                  33

<210> SEQ ID NO 25
<211> LENGTH: 35
<212> TYPE: DNA
<213> ORGANISM: Artificial Sequence
<220> FEATURE:
<223> OTHER INFORMATION: the oligonucleotide cassette encoding
      intergenic sequence 2 (IGS2) for E. coli Fab expression.

<400> SEQUENCE: 25
aagttttaat agaggggagt gttaaaatga agaag                                35

<210> SEQ ID NO 26
<211> LENGTH: 47
<212> TYPE: DNA
<213> ORGANISM: Artificial Sequence
<220> FEATURE:
<223> OTHER INFORMATION: oligonucleotide cassette encoding intergenic
      sequence 3 (IGS3) for E. coli Fab expression

<400> SEQUENCE: 26
aagctttaat agaggagagt gttgaggagg aaaaaaaat gaagaaa                    47

<210> SEQ ID NO 27
<211> LENGTH: 47
<212> TYPE: DNA
<213> ORGANISM: Artificial Sequence
<220> FEATURE:
<223> OTHER INFORMATION: oligonucleotide cassette encoding intergenic
      sequence 4 (IGS4) for E. coli Fab expression

<400> SEQUENCE: 27
aagctttaat agaggagagt gttgacgagg attatataat gaagaaa                   47

<210> SEQ ID NO 28
<211> LENGTH: 810
<212> TYPE: DNA
<213> ORGANISM: Escherichia coli
```

<400> SEQUENCE: 28

```
atgaaatcac tgtttaaagt aacgctgctg gcgaccacaa tggccgttgc cctgcatgca      60
ccaatcactt ttgctgctga agctgcaaaa cctgctacag ctgctgacag caaagcagcg     120
ttcaaaaatg acgatcagaa atcagcttat gcactgggtg cctcgctggg tcgttacatg     180
gaaaactctc taaaagaaca gaaaaactg gcatcaaac tggataaaga tcagctgatc       240
gctggtgttc aggatgcatt tgctgataag agcaaactct ccgaccaaga gatcgaacag     300
actctacaag cattcgaagc tcgcgtgaag tcttctgctc aggcgaagat ggaaaaagac     360
gcggctgata cgaagcaaa aggtaaagag taccgcgaga aatttgccaa agagaaaggt     420
gtgaaaacct cttcaactgg tctggtttat caggtagtag aagccggtaa aggcgaagca     480
ccgaaagaca gcgatactgt tgtagtgaac tacaaaggta cgctgatcga cggtaaagag     540
ttcgacaact cttacacccg tggtgaaccg ctttctttcc gtctggacgg tgttatcccg     600
ggttggacag aaggtctgaa gaacatcaag aaaggcggta agatcaaact ggttattcca     660
ccagaactgg cttacggcaa agcgggtgtt ccggggatcc accgaattc taccctggtg      720
tttgacgtag agctgctgga tgtgaaacca gcgccgaagg ctgatgcaaa gccggaagct     780
gatgcgaaag ccgcagattc tgctaaaaaa                                      810
```

<210> SEQ ID NO 29
<211> LENGTH: 270
<212> TYPE: PRT
<213> ORGANISM: Escherichia coli

<400> SEQUENCE: 29

```
Met Lys Ser Leu Phe Lys Val Thr Leu Leu Ala Thr Thr Met Ala Val
1               5                   10                  15

Ala Leu His Ala Pro Ile Thr Phe Ala Ala Glu Ala Ala Lys Pro Ala
            20                  25                  30

Thr Ala Ala Asp Ser Lys Ala Ala Phe Lys Asn Asp Asp Gln Lys Ser
        35                  40                  45

Ala Tyr Ala Leu Gly Ala Ser Leu Gly Arg Tyr Met Glu Asn Ser Leu
    50                  55                  60

Lys Glu Gln Glu Lys Leu Gly Ile Lys Leu Asp Lys Asp Gln Leu Ile
65                  70                  75                  80

Ala Gly Val Gln Asp Ala Phe Ala Asp Lys Ser Lys Leu Ser Asp Gln
                85                  90                  95

Glu Ile Glu Gln Thr Leu Gln Ala Phe Glu Ala Arg Val Lys Ser Ser
            100                 105                 110

Ala Gln Ala Lys Met Glu Lys Asp Ala Ala Asp Asn Glu Ala Lys Gly
        115                 120                 125

Lys Glu Tyr Arg Glu Lys Phe Ala Lys Glu Lys Gly Val Lys Thr Ser
    130                 135                 140

Ser Thr Gly Leu Val Tyr Gln Val Val Glu Ala Gly Lys Gly Glu Ala
145                 150                 155                 160

Pro Lys Asp Ser Asp Thr Val Val Val Asn Tyr Lys Gly Thr Leu Ile
                165                 170                 175

Asp Gly Lys Glu Phe Asp Asn Ser Tyr Thr Arg Gly Glu Pro Leu Ser
            180                 185                 190

Phe Arg Leu Asp Gly Val Ile Pro Gly Trp Thr Glu Gly Leu Lys Asn
        195                 200                 205

Ile Lys Lys Gly Gly Lys Ile Lys Leu Val Ile Pro Pro Glu Leu Ala
```

```
                210                 215                 220
Tyr Gly Lys Ala Gly Val Pro Gly Ile Pro Pro Asn Ser Thr Leu Val
225                 230                 235                 240

Phe Asp Val Glu Leu Leu Asp Val Lys Pro Ala Pro Lys Ala Asp Ala
                245                 250                 255

Lys Pro Glu Ala Asp Ala Lys Ala Ala Asp Ser Ala Lys Lys
                260                 265                 270

<210> SEQ ID NO 30
<211> LENGTH: 828
<212> TYPE: DNA
<213> ORGANISM: Artificial Sequence
<220> FEATURE:
<223> OTHER INFORMATION: the FkpA tagged gene

<400> SEQUENCE: 30
atgaaatcac tgtttaaagt aacgctgctg gcgaccacaa tggccgttgc cctgcacgca      60
ccaatcactt ttgctgctga agctgcaaaa cctgctactg ctgctgacag caaagcagcg     120
ttcaaaaatg acgatcagaa atcagcttat gcactgggtg cctcgctggg tcgttacatg     180
gaaaactctc taaagaaaca agaaaaactg ggcatcaaac tggataaaga tcaactgatc     240
gctggtgttc aggatgcatt tgctgataag agcaaactct ccgaccaaga gatcgaacag     300
actctacaag catttgaagc tcgcgtgaag tcttctgctc aggcgaagat ggaaaaagac     360
gcggctgata cgaagcaaaa aggtaaagag taccgcgaga atttgccaa agagaaaggt     420 gtgaaaacct cttcaactgg tctggtttat caggtagtag aagccggtaa aggcgaagca     480
ccgaaagaca gcgatactgt tgtagtgaac tacaaaggta cgctgatcga cggtaaagag     540
ttcgacaact cttacacccg tggtgaaccg ctttctttcc gtctggacgg tgttatcccg     600
ggttggacag aaggtctgaa gaacatcaag aaaggcggta gataaaact ggttattcca     660 ccagaactgg cttacggcaa agcgggtgtt ccggggattc caccaaattc taccctggtg     720
tttgacgtag agctgctgga tgtgaaacca gcgccgaagg ctgatgcaaa gccggaagct     780
gatgcgaaag ccgcagattc tgctaaaaaa caccatcacc atcaccac              828

<210> SEQ ID NO 31
<211> LENGTH: 276
<212> TYPE: PRT
<213> ORGANISM: Artificial Sequence
<220> FEATURE:
<223> OTHER INFORMATION: FkpA his tagged gene

<400> SEQUENCE: 31

Met Lys Ser Leu Phe Lys Val Thr Leu Leu Ala Thr Thr Met Ala Val
1               5                   10                  15

Ala Leu His Ala Pro Ile Thr Phe Ala Ala Glu Ala Ala Lys Pro Ala
                20                  25                  30

Thr Ala Ala Asp Ser Lys Ala Ala Phe Lys Asn Asp Asp Gln Lys Ser
            35                  40                  45

Ala Tyr Ala Leu Gly Ala Ser Leu Gly Arg Tyr Met Glu Asn Ser Leu
        50                  55                  60

Lys Glu Gln Glu Lys Leu Gly Ile Lys Leu Asp Lys Asp Gln Leu Ile
65                  70                  75                  80

Ala Gly Val Gln Asp Ala Phe Ala Asp Lys Ser Lys Leu Ser Asp Gln
                85                  90                  95

Glu Ile Glu Gln Thr Leu Gln Ala Phe Glu Ala Arg Val Lys Ser Ser
                100                 105                 110
```

Ala Gln Ala Lys Met Glu Lys Asp Ala Ala Asp Asn Glu Ala Lys Gly
        115                 120                 125

Lys Glu Tyr Arg Glu Lys Phe Ala Lys Glu Lys Gly Val Lys Thr Ser
        130                 135                 140

Ser Thr Gly Leu Val Tyr Gln Val Val Glu Ala Gly Lys Gly Glu Ala
145                 150                 155                 160

Pro Lys Asp Ser Asp Thr Val Val Asn Tyr Lys Gly Thr Leu Ile
                165                 170                 175

Asp Gly Lys Glu Phe Asp Asn Ser Tyr Thr Arg Gly Glu Pro Leu Ser
                180                 185                 190

Phe Arg Leu Asp Gly Val Ile Pro Gly Trp Thr Glu Gly Leu Lys Asn
                195                 200                 205

Ile Lys Lys Gly Gly Lys Ile Lys Leu Val Ile Pro Pro Glu Leu Ala
        210                 215                 220

Tyr Gly Lys Ala Gly Val Pro Gly Ile Pro Pro Asn Ser Thr Leu Val
225                 230                 235                 240

Phe Asp Val Glu Leu Leu Asp Val Lys Pro Ala Pro Lys Ala Asp Ala
                245                 250                 255

Lys Pro Glu Ala Asp Ala Lys Ala Ala Asp Ser Ala Lys Lys His His
                260                 265                 270

His His His His
        275

<210> SEQ ID NO 32
<211> LENGTH: 486
<212> TYPE: DNA
<213> ORGANISM: Escherichia coli

<400> SEQUENCE: 32
gtgaaaaagt ggttattagc tgcaggtctc ggtttagcac tggcaacttc tgctcaggcg      60
gctgacaaaa ttgcaatcgt caacatgggc agcctgttcc agcaggtagc gcagaaaacc     120
ggtgtttcta acacgctgga aaatgagttc aaaggccgtg ccagcgaact gcagcgtatg     180
gaaaccgatc tgcaggctaa atgaaaaag ctgcagtcca tgaaagcggg cagcgatcgc      240
actaagctgg aaaagacgt gatggctcag cgccagactt ttgctcagaa agcgcaggct     300
tttgagcagg atcgcgcacg tcgttccaac gaagaacgcg gcaaactggt tactcgtatc     360
cagactgctg tgaaatccgt tgccaacagc caggatatcg atctggttgt tgatgcaaac     420
gccgttgctt acaacagcag cgatgtaaaa gacatcactg ccgacgtact gaaacaggtt     480
aaataa                                                                 486

<210> SEQ ID NO 33
<211> LENGTH: 161
<212> TYPE: PRT
<213> ORGANISM: Escherichia coli

<400> SEQUENCE: 33

Met Lys Lys Trp Leu Leu Ala Ala Gly Leu Gly Leu Ala Leu Ala Thr
1               5                   10                  15

Ser Ala Gln Ala Ala Asp Lys Ile Ala Ile Val Asn Met Gly Ser Leu
                20                  25                  30

Phe Gln Gln Val Ala Gln Lys Thr Gly Val Ser Asn Thr Leu Glu Asn
        35                  40                  45

Glu Phe Lys Gly Arg Ala Ser Glu Leu Gln Arg Met Glu Thr Asp Leu
    50                  55                  60

```
Gln Ala Lys Met Lys Lys Leu Gln Ser Met Lys Ala Gly Ser Asp Arg
 65                  70                  75                  80

Thr Lys Leu Glu Lys Asp Val Met Ala Gln Arg Gln Thr Phe Ala Gln
             85                  90                  95

Lys Ala Gln Ala Phe Glu Gln Asp Arg Ala Arg Arg Ser Asn Glu Glu
            100                 105                 110

Arg Gly Lys Leu Val Thr Arg Ile Gln Thr Ala Val Lys Ser Val Ala
        115                 120                 125

Asn Ser Gln Asp Ile Asp Leu Val Val Asp Ala Asn Ala Val Ala Tyr
130                 135                 140

Asn Ser Ser Asp Val Lys Asp Ile Thr Ala Asp Val Leu Lys Gln Val
145                 150                 155                 160

Lys
```

<210> SEQ ID NO 34
<211> LENGTH: 501
<212> TYPE: DNA
<213> ORGANISM: Artificial Sequence
<220> FEATURE:
<223> OTHER INFORMATION: skp his tagged gene

<400> SEQUENCE: 34

```
atgaaaaagt ggttattagc cgcaggtctc ggtttagcac tggcaacttc tgctcaggcg    60
gctgacaaaa ttgcaatcgt caacatgggc agcctgttcc agcaggtagc gcagaaaacc   120
ggtgttctta acacgctgga aaatgagttc aaaggccgtg ccagcgaact ccagcgtatg   180
gaaaccgatc tccaggctaa atgaaaaag ctgcaatcca tgaaagcggg cagcgatcgc   240
actaagctgg aaaagacgt gatggctcag cgccagactt tgctcagaa agcgcaggct   300
tttgagcagg atcgcgcacg tcgttccaac gaagaacgcg gcaaactggt tactcgtatc   360
cagactgctg tgaaatccgt tgccaacagc caggaaatcg atctggttgt tgatgcaaac   420
gccgttgctt acaacagcag cgatgtaaaa gacatcactg ccgacgtact gaaacaggtt   480
aaacaccatc accatcacca c                                             501
```

<210> SEQ ID NO 35
<211> LENGTH: 167
<212> TYPE: PRT
<213> ORGANISM: Artificial Sequence
<220> FEATURE:
<223> OTHER INFORMATION: skp his tagged gene

<400> SEQUENCE: 35

```
Met Lys Lys Trp Leu Leu Ala Ala Gly Leu Gly Leu Ala Leu Ala Thr
  1               5                  10                  15

Ser Ala Gln Ala Ala Asp Lys Ile Ala Ile Val Asn Met Gly Ser Leu
             20                  25                  30

Phe Gln Gln Val Ala Gln Lys Thr Gly Val Ser Asn Thr Leu Glu Asn
             35                  40                  45

Glu Phe Lys Gly Arg Ala Ser Glu Leu Gln Arg Met Glu Thr Asp Leu
         50                  55                  60

Gln Ala Lys Met Lys Lys Leu Gln Ser Met Lys Ala Gly Ser Asp Arg
 65                  70                  75                  80

Thr Lys Leu Glu Lys Asp Val Met Ala Gln Arg Gln Thr Phe Ala Gln
             85                  90                  95

Lys Ala Gln Ala Phe Glu Gln Asp Arg Ala Arg Arg Ser Asn Glu Glu
            100                 105                 110
```

Arg Gly Lys Leu Val Thr Arg Ile Gln Thr Ala Val Lys Ser Val Ala
        115                 120                 125

Asn Ser Gln Glu Ile Asp Leu Val Val Asp Ala Asn Ala Val Ala Tyr
    130                 135                 140

Asn Ser Ser Asp Val Lys Asp Ile Thr Ala Asp Val Leu Lys Gln Val
145                 150                 155                 160

Lys His His His His His
                165

<210> SEQ ID NO 36
<211> LENGTH: 10
<212> TYPE: PRT
<213> ORGANISM: Artificial Sequence
<220> FEATURE:
<223> OTHER INFORMATION: CA170_1519 Ab CDRH1

<400> SEQUENCE: 36

Gly Phe Thr Phe Ser Asn Tyr Gly Met Val
1               5                   10

<210> SEQ ID NO 37
<211> LENGTH: 17
<212> TYPE: PRT
<213> ORGANISM: Artificial Sequence
<220> FEATURE:
<223> OTHER INFORMATION: CA170_1519 Ab CDRH2

<400> SEQUENCE: 37

Tyr Ile Asp Ser Asp Gly Asp Asn Thr Tyr Tyr Arg Asp Ser Val Lys
1               5                   10                  15

Gly

<210> SEQ ID NO 38
<211> LENGTH: 8
<212> TYPE: PRT
<213> ORGANISM: Artificial Sequence
<220> FEATURE:
<223> OTHER INFORMATION: CA170_1519 Ab CDRH3

<400> SEQUENCE: 38

Gly Ile Val Arg Pro Phe Leu Tyr
1               5

<210> SEQ ID NO 39
<211> LENGTH: 16
<212> TYPE: PRT
<213> ORGANISM: Artificial Sequence
<220> FEATURE:
<223> OTHER INFORMATION: CA170_1519 Ab CDRL1

<400> SEQUENCE: 39

Lys Ser Ser Gln Ser Leu Val Gly Ala Ser Gly Lys Thr Tyr Leu Tyr
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: CA170_1519 Ab CDRL2

<400> SEQUENCE: 40

Leu Val Ser Thr Leu Asp Ser
1               5

<210> SEQ ID NO 41
<211> LENGTH: 9
<212> TYPE: PRT
<213> ORGANISM: Artificial Sequence
<220> FEATURE:
<223> OTHER INFORMATION: CA170_1519 Ab CDRL3

<400> SEQUENCE: 41

Leu Gln Gly Thr His Phe Pro His Thr
1               5

<210> SEQ ID NO 42
<211> LENGTH: 112
<212> TYPE: PRT
<213> ORGANISM: Artificial Sequence
<220> FEATURE:
<223> OTHER INFORMATION: Rat Ab 1519 VL region

<400> SEQUENCE: 42

Asp Val Val Met Thr Gln Thr Pro Leu Ser Leu Ser Val Ala Leu Gly
1               5                   10                  15

Gln Pro Ala Ser Ile Ser Cys Lys Ser Ser Gln Ser Leu Val Gly Ala
            20                  25                  30

Ser Gly Lys Thr Tyr Leu Tyr Trp Leu Phe Gln Arg Ser Gly Gln Ser
        35                  40                  45

Pro Lys Arg Leu Ile Tyr Leu Val Ser Thr Leu Asp Ser Gly Ile Pro
    50                  55                  60

Asp Arg Phe Ser Gly Ser Gly Ala Glu Thr Asp Phe Thr Leu Lys Ile
65                  70                  75                  80

Arg Arg Val Glu Ala Asp Asp Leu Gly Val Tyr Tyr Cys Leu Gln Gly
                85                  90                  95

Thr His Phe Pro His Thr Phe Gly Ala Gly Thr Lys Leu Glu Leu Lys
            100                 105                 110

<210> SEQ ID NO 43
<211> LENGTH: 336
<212> TYPE: DNA
<213> ORGANISM: Artificial Sequence
<220> FEATURE:
<223> OTHER INFORMATION: Rat Ab 1519 VL region

<400> SEQUENCE: 43
gatgttgtga tgacccagac tccactgtct ttgtcggttg cccttggaca accagcctcc      60
atctcttgca agtcaagtca gagcctcgta ggtgctagtg gaaagacata tttgtattgg     120
ttatttcaga ggtccggcca gtctccaaag cgactaatct atctggtgtc cacactggac     180
tctggaattc ctgataggtt cagtggcagt ggagcagaga cagattttac tcttaaaatc     240
cgcagagtgg aagccgatga tttgggagtt tattactgct tgcaaggtac acatttccct     300
cacacgtttg gagctgggac caagctggaa ttgaaa                               336

<210> SEQ ID NO 44
<211> LENGTH: 132
<212> TYPE: PRT
<213> ORGANISM: Artificial Sequence
<220> FEATURE:
<223> OTHER INFORMATION: Rat Ab 1519 VL region

<400> SEQUENCE: 44

Met Met Ser Pro Ala Gln Phe Leu Phe Leu Leu Met Leu Trp Ile Gln
1               5                   10                  15

```
Gly Thr Ser Gly Asp Val Val Met Thr Gln Thr Pro Leu Ser Leu Ser
            20                  25                  30

Val Ala Leu Gly Gln Pro Ala Ser Ile Ser Cys Lys Ser Ser Gln Ser
        35                  40                  45

Leu Val Gly Ala Ser Gly Lys Thr Tyr Leu Tyr Trp Leu Phe Gln Arg
    50                  55                  60

Ser Gly Gln Ser Pro Lys Arg Leu Ile Tyr Leu Val Ser Thr Leu Asp
65                  70                  75                  80

Ser Gly Ile Pro Asp Arg Phe Ser Gly Ser Gly Ala Glu Thr Asp Phe
                85                  90                  95

Thr Leu Lys Ile Arg Arg Val Glu Ala Asp Asp Leu Gly Val Tyr Tyr
            100                 105                 110

Cys Leu Gln Gly Thr His Phe Pro His Thr Phe Gly Ala Gly Thr Lys
            115                 120                 125

Leu Glu Leu Lys
    130
```

<210> SEQ ID NO 45
<211> LENGTH: 396
<212> TYPE: DNA
<213> ORGANISM: Artificial Sequence
<220> FEATURE:
<223> OTHER INFORMATION: Rat Ab 1519 VL region

<400> SEQUENCE: 45

```
atgatgagtc ctgcccagtt cctgtttctg ctgatgctct ggattcaggg aaccagtggt      60
gatgttgtga tgacccagac tccactgtct ttgtcggttg cccttggaca accagcctcc     120
atctcttgca agtcaagtca gagcctcgta ggtgctagtg gaaagacata tttgtattgg     180
ttatttcaga ggtccggcca gtctccaaag cgactaatct atctggtgtc cacactggac     240
tctggaattc ctgataggtt cagtggcagt ggagcagaga cagattttac tcttaaaatc     300
cgcagagtgg aagccgatga tttgggagtt tattactgct tgcaaggtac acattttcct     360
cacacgtttg gagctgggac caagctggaa ttgaaa                              396
```

<210> SEQ ID NO 46
<211> LENGTH: 116
<212> TYPE: PRT
<213> ORGANISM: Artificial Sequence
<220> FEATURE:
<223> OTHER INFORMATION: Rat Ab 1519 VH region

<400> SEQUENCE: 46

```
Glu Val Pro Leu Val Glu Ser Gly Gly Gly Ser Val Gln Pro Gly Arg
1               5                   10                  15

Ser Met Lys Leu Ser Cys Val Val Ser Gly Phe Thr Phe Ser Asn Tyr
            20                  25                  30

Gly Met Val Trp Val Arg Gln Ala Pro Lys Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asn Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Thr Gly Ile Val Arg Pro Phe Leu Tyr Trp Gly Gln Gly Thr Thr
            100                 105                 110
```

Val Thr Val Ser
        115

<210> SEQ ID NO 47
<211> LENGTH: 348
<212> TYPE: DNA
<213> ORGANISM: Artificial Sequence
<220> FEATURE:
<223> OTHER INFORMATION: Rat Ab 1519 VH region

<400> SEQUENCE: 47

```
gaggtgccgc tggtggagtc tgggggcggc tcagtgcagc ctgggaggtc catgaaactc     60
tcctgtgtag tctcaggatt cactttcagt aattatggca tggtctgggt ccgccaggct    120
ccaaagaagg gtctggagtg ggtcgcatat attgattctg atggtgataa tacttactac    180
cgagattccg tgaagggccg attcactatc tccagaaata tgcaaaaag caccctatat     240 ttgcaaatgg acagtctgag gtctgaggac acggccactt attactgtac aacagggatt    300 gtccggcccct ttctctattg gggccaagga accacggtca ccgtctcg               348
```

<210> SEQ ID NO 48
<211> LENGTH: 135
<212> TYPE: PRT
<213> ORGANISM: Artificial Sequence
<220> FEATURE:
<223> OTHER INFORMATION: Rat Ab 1519 VH region

<400> SEQUENCE: 48

Met Asp Ile Ser Leu Ser Leu Ala Phe Leu Val Leu Phe Ile Lys Gly
1               5                   10                  15

Val Arg Cys Glu Val Pro Leu Val Glu Ser Gly Gly Gly Ser Val Gln
            20                  25                  30

Pro Gly Arg Ser Met Lys Leu Ser Cys Val Val Ser Gly Phe Thr Phe
        35                  40                  45

Ser Asn Tyr Gly Met Val Trp Val Arg Gln Ala Pro Lys Lys Gly Leu
    50                  55                  60

Glu Trp Val Ala Tyr Ile Asp Ser Asp Gly Asp Asn Thr Tyr Tyr Arg
65                  70                  75                  80

Asp Ser Val Lys Gly Arg Phe Thr Ile Ser Arg Asn Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Thr Thr Gly Ile Val Arg Pro Phe Leu Tyr Trp Gly Gln
        115                 120                 125

Gly Thr Thr Val Thr Val Ser
    130                 135

<210> SEQ ID NO 49
<211> LENGTH: 405
<212> TYPE: DNA
<213> ORGANISM: Artificial Sequence
<220> FEATURE:
<223> OTHER INFORMATION: Rat Ab 1519 VH region

<400> SEQUENCE: 49

```
atggacatca gtctcagctt ggctttcctt gtccttttca taaaggtgt ccggtgtgag      60 gtgccgctgg tggagtctgg gggcggctca gtgcagcctg ggaggtccat gaaactctcc    120
tgtgtagtct caggattcac tttcagtaat tatggcatgg tctgggtccg ccaggctcca    180
```

```
aagaagggtc tggagtgggt cgcatatatt gattctgatg gtgataatac ttactaccga    240
gattccgtga agggccgatt cactatctcc agaaataatg caaaaagcac cctatatttg    300
caaatggaca gtctgaggtc tgaggacacg gccacttatt actgtacaac agggattgtc    360
cggccctttc tctattgggg ccaaggaacc acggtcaccg tctcg                    405
```

<210> SEQ ID NO 50
<211> LENGTH: 112
<212> TYPE: PRT
<213> ORGANISM: Artificial Sequence
<220> FEATURE:
<223> OTHER INFORMATION: 1519 gL20 V-region

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
            20                  25                  30

Ser Gly Lys Thr Tyr Leu Tyr Trp Leu Phe Gln Lys Pro Gly Lys Ala
        35                  40                  45

Pro Lys Arg Leu Ile Tyr Leu Val Ser Thr Leu Asp Ser Gly Ile Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Phe Pro His Thr Phe Gly Gln Gly Thr Lys Leu Glu Ile Lys
            100                 105                 110
```

<210> SEQ ID NO 51
<211> LENGTH: 336
<212> TYPE: DNA
<213> ORGANISM: Artificial Sequence
<220> FEATURE:
<223> OTHER INFORMATION: 1519 gL20 V-region

<400> SEQUENCE: 51

```
gatatccaga tgacccagag tccaagcagt ctctccgcca gcgtaggcga tcgtgtgact     60
attacctgta aaagctccca gtccctggtg ggtgcaagcg gcaaaaccta cctgtactgg    120
ctcttccaga aaccgggcaa agctccgaaa cgcctgatct atctggtgtc taccctggat    180
agcggtattc cgtctcgttt ctccggtagc ggtagcggta ccgaattcac gctgaccatt    240
agctccctcc agccggagga ctttgctacc tattactgcc tccagggcac tcattttccg    300
cacactttcg gccagggtac caaactggaa atcaaa                              336
```

<210> SEQ ID NO 52
<211> LENGTH: 133
<212> TYPE: PRT
<213> ORGANISM: Artificial Sequence
<220> FEATURE:
<223> OTHER INFORMATION: 1519 gL20 V-region

<400> SEQUENCE: 52

```
Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
            20                  25                  30

Ser Ala Ser Val Gly Asp Arg Val Thr Ile Thr Cys Lys Ser Ser Gln
        35                  40                  45
```

Ser Leu Val Gly Ala Ser Gly Lys Thr Tyr Leu Tyr Trp Leu Phe Gln
    50                  55                  60

Lys Pro Gly Lys Ala Pro Lys Arg Leu Ile Tyr Leu Val Ser Thr Leu
65                  70                  75                  80

Asp Ser Gly Ile Pro Ser Arg Phe Ser Gly Ser Gly Ser Gly Thr Glu
                85                  90                  95

Phe Thr Leu Thr Ile Ser Ser Leu Gln Pro Glu Asp Phe Ala Thr Tyr
                100                 105                 110

Tyr Cys Leu Gln Gly Thr His Phe Pro His Thr Phe Gly Gln Gly Thr
            115                 120                 125

Lys Leu Glu Ile Lys
    130

<210> SEQ ID NO 53
<211> LENGTH: 399
<212> TYPE: DNA
<213> ORGANISM: Artificial Sequence
<220> FEATURE:
<223> OTHER INFORMATION: 1519 gL20 V-region

<400> SEQUENCE: 53
atgaaaaaga cagctatcgc aattgcagtg gccttggctg gtttcgctac cgtagcgcaa      60
gctgatatcc agatgaccca gagtccaagc agtctctccg ccagcgtagg cgatcgtgtg     120
actattacct gtaaaagctc ccagtccctg gtgggtgcaa gcggcaaaac ctacctgtac     180
tggctcttcc agaaaccggg caaagctccg aaacgcctga tctatctggt gtctacccta     240
gatagcggta ttccgtctcg tttctccggt agcggtagcg gtaccgaatt cacgctgacc     300
attagctccc tccagccgga ggactttgct acctattact gcctccaggg cactcatttt     360
ccgcacactt tcggccaggg taccaaactg gaaatcaaa                            399

<210> SEQ ID NO 54
<211> LENGTH: 219
<212> TYPE: PRT
<213> ORGANISM: Artificial Sequence
<220> FEATURE:
<223> OTHER INFORMATION: 1519 gL20 light chain (V + constant)

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
                20                  25                  30

Ser Gly Lys Thr Tyr Leu Tyr Trp Leu Phe Gln Lys Pro Gly Lys Ala
            35                  40                  45

Pro Lys Arg Leu Ile Tyr Leu Val Ser Thr Leu Asp Ser Gly Ile Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Phe Pro His Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 55
<211> LENGTH: 657
<212> TYPE: DNA
<213> ORGANISM: Artificial Sequence
<220> FEATURE:
<223> OTHER INFORMATION: 1519 gL20 light chain (V + constant)

<400> SEQUENCE: 55
gatatccaga tgacccagag tccaagcagt ctctccgcca gcgtaggcga tcgtgtgact      60
attacctgta aaagctccca gtccctggtg ggtgcaagcg gcaaaaccta cctgtactgg     120
ctcttccaga aacgggcaa agctccgaaa cgcctgatct atctggtgtc taccctggat      180
agcggtattc cgtctcgttt ctccggtagc ggtagcggta ccgaattcac gctgaccatt     240
agctccctcc agccggagga ctttgctacc tattactgcc tccagggcac tcattttccg     300
cacactttcg gccagggtac caaactggaa atcaaacgta cggtagcggc cccatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcaccagta acaaaaagtt ttaatagagg ggagtgt        657

<210> SEQ ID NO 56
<211> LENGTH: 240
<212> TYPE: PRT
<213> ORGANISM: Artificial Sequence
<220> FEATURE:
<223> OTHER INFORMATION: 1519 gL20 light chain

<400> SEQUENCE: 56

Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
            20                  25                  30

Ser Ala Ser Val Gly Asp Arg Val Thr Ile Thr Cys Lys Ser Ser Gln
        35                  40                  45

Ser Leu Val Gly Ala Ser Gly Lys Thr Tyr Leu Tyr Trp Leu Phe Gln
    50                  55                  60

Lys Pro Gly Lys Ala Pro Lys Arg Leu Ile Tyr Leu Val Ser Thr Leu
65                  70                  75                  80

Asp Ser Gly Ile Pro Ser Arg Phe Ser Gly Ser Gly Ser Gly Thr Glu
                85                  90                  95

Phe Thr Leu Thr Ile Ser Ser Leu Gln Pro Glu Asp Phe Ala Thr Tyr
            100                 105                 110

```
Tyr Cys Leu Gln Gly Thr His Phe Pro His Thr Phe Gly Gln Gly Thr
            115                 120                 125
Lys Leu Glu Ile Lys Arg Thr Val Ala Ala Pro Ser Val Phe Ile Phe
    130                 135                 140
Pro Pro Ser Asp Glu Gln Leu Lys Ser Gly Thr Ala Ser Val Val Cys
145                 150                 155                 160
Leu Leu Asn Asn Phe Tyr Pro Arg Glu Ala Lys Val Gln Trp Lys Val
                165                 170                 175
Asp Asn Ala Leu Gln Ser Gly Asn Ser Gln Glu Ser Val Thr Glu Gln
            180                 185                 190
Asp Ser Lys Asp Ser Thr Tyr Ser Leu Ser Ser Thr Leu Thr Leu Ser
        195                 200                 205
Lys Ala Asp Tyr Glu Lys His Lys Val Tyr Ala Cys Glu Val Thr His
    210                 215                 220
Gln Gly Leu Ser Ser Pro Val Thr Lys Ser Phe Asn Arg Gly Glu Cys
225                 230                 235                 240
```

<210> SEQ ID NO 57
<211> LENGTH: 720
<212> TYPE: DNA
<213> ORGANISM: Artificial Sequence
<220> FEATURE:
<223> OTHER INFORMATION: 1519 gL20 light chain

<400> SEQUENCE: 57

| | | |
|---|---|---|
| atgaaaaaga cagctatcgc aattgcagtg gccttggctg gtttcgctac cgtagcgcaa | 60 |
| gctgatatcc agatgaccca gagtccaagc agtctctccg ccagcgtagg cgatcgtgtg | 120 |
| actattacct gtaaaagctc ccagtccctg gtgggtgcaa gcggcaaaac ctacctgtac | 180 |
| tggctcttcc agaaaccggg caaagctccg aaacgcctga tctatctggt gtctaccctg | 240 |
| gatagcggta ttccgtctcg tttctccggt agcggtagcg gtaccgaatt cacgctgacc | 300 |
| attagctccc tccagccgga ggactttgct acctattact gctcccaggg cactcatttt | 360 |
| ccgcacactt tcggccaggg taccaaactg gaaatcaaac gtacggtagc ggccccatct | 420 |
| gtcttcatct tcccgccatc tgatgagcag ttgaaatctg gaactgcctc tgttgtgtgc | 480 |
| ctgctgaata acttctatcc cagagaggcc aaagtacagt ggaaggtgga taacgccctc | 540 |
| caatcgggta actcccagga gagtgtcaca gagcaggaca gcaaggacag cacctacagc | 600 |
| ctcagcagca ccctgacgct gagcaaagca gactacgaga aacacaaagt ctacgcctgc | 660 |
| gaagtcaccc atcagggcct gagctcacca gtaacaaaaa gttttaatag aggggagtgt | 720 |

<210> SEQ ID NO 58
<211> LENGTH: 116
<212> TYPE: PRT
<213> ORGANISM: Artificial Sequence
<220> FEATURE:
<223> OTHER INFORMATION: 1519 gH20 V-region

<400> SEQUENCE: 58

```
Glu Val Pro Leu Val Glu Ser Gly Gly Gly Leu Val Gln Pro Gly Gly
1               5                   10                  15
Ser Leu Arg Leu Ser Cys Ala Val Ser Gly Phe Thr Phe Ser Asn Tyr
            20                  25                  30
Gly Met Val Trp Val Arg Gln Ala Pro Gly Lys Gly Leu Glu Trp Val
        35                  40                  45
Ala Tyr Ile Asp Ser Asp Gly Asp Asn Thr Tyr Tyr Arg Asp Ser Val
    50                  55                  60
```

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
            85                  90                  95

Thr Thr Gly Ile Val Arg Pro Phe Leu Tyr Trp Gly Gln Gly Thr Leu
        100                 105                 110

Val Thr Val Ser
        115

<210> SEQ ID NO 59
<211> LENGTH: 348
<212> TYPE: DNA
<213> ORGANISM: Artificial Sequence
<220> FEATURE:
<223> OTHER INFORMATION: 1519 gH20 V-region

<400> SEQUENCE: 59
gaggttccgc tggtcgagtc tggaggcggg cttgtccagc ctggagggag cctgcgtctc    60
tcttgtgcag tatctggctt cacgttctcc aactacggta tggtgtgggt tcgtcaggct   120
ccaggtaaag gtctggaatg ggtggcgtat attgactccg acggcgacaa cacctactat   180
cgcgactctg tgaaaggtcg cttcaccatt tcccgcgata cgccaaatc cagcctgtac    240 ctgcagatga acagcctgcg tgctgaagat actgcggtgt actattgcac cactggcatc   300
gtgcgtccgt ttctgtattg gggtcagggt accctcgtta ctgtctcg                348

<210> SEQ ID NO 60
<211> LENGTH: 137
<212> TYPE: PRT
<213> ORGANISM: Artificial Sequence
<220> FEATURE:
<223> OTHER INFORMATION: 1519 gH20 V-region

<400> SEQUENCE: 60

Met Lys Lys Thr Ala Ile Ala Ile Ala Val Ala Leu Ala Gly Phe Ala
1               5                   10                  15

Thr Val Ala Gln Ala Glu Val Pro Leu Val Glu Ser Gly Gly Gly Leu
            20                  25                  30

Val Gln Pro Gly Gly Ser Leu Arg Leu Ser Cys Ala Val Ser Gly Phe
        35                  40                  45

Thr Phe Ser Asn Tyr Gly Met Val Trp Val Arg Gln Ala Pro Gly Lys
    50                  55                  60

Gly Leu Glu Trp Val Ala Tyr Ile Asp Ser Asp Gly Asp Asn Thr Tyr
65                  70                  75                  80

Tyr Arg Asp Ser Val Lys Gly Arg Phe Thr Ile Ser Arg Asp Asn Ala
            85                  90                  95

Lys Ser Ser Leu Tyr Leu Gln Met Asn Ser Leu Arg Ala Glu Asp Thr
        100                 105                 110

Ala Val Tyr Tyr Cys Thr Thr Gly Ile Val Arg Pro Phe Leu Tyr Trp
    115                 120                 125

Gly Gln Gly Thr Leu Val Thr Val Ser
    130                 135

<210> SEQ ID NO 61
<211> LENGTH: 411
<212> TYPE: DNA
<213> ORGANISM: Artificial Sequence
<220> FEATURE:
<223> OTHER INFORMATION: 1519 gH20 V-region

<400> SEQUENCE: 61

```
atgaagaaga ctgctatagc aattgcagtg gcgctagctg gtttcgccac cgtggcgcaa    60
gctgaggttc cgctggtcga gtctggaggc gggcttgtcc agcctggagg gagcctgcgt   120
ctctcttgtg cagtatctgg cttcacgttc tccaactacg gtatggtgtg ggttcgtcag   180
gctccaggta aagtctggaa tgggtggcg tatattgact ccgacggcga caacacctac   240
tatcgcgact ctgtgaaagg tcgcttcacc atttcccgcg ataacgccaa atccagcctg   300
tacctgcaga tgaacagcct gcgtgctgaa gatactgcgg tgtactattg caccactggc   360
atcgtgcgtc cgtttctgta ttggggtcag ggtaccctcg ttactgtctc g            411
```

<210> SEQ ID NO 62
<211> LENGTH: 228
<212> TYPE: PRT
<213> ORGANISM: Artificial Sequence
<220> FEATURE:
<223> OTHER INFORMATION: 1519gH20 Fab' heavy chain (V + human gamma-1
      CH1 + hinge)

<400> SEQUENCE: 62

```
Glu Val Pro Leu Val Glu Ser Gly Gly Gly Leu Val Gln Pro Gly Gly
1               5                   10                  15
Ser Leu Arg Leu Ser Cys Ala Val Ser Gly Phe Thr Phe Ser Asn Tyr
            20                  25                  30
Gly Met Val Trp Val Arg Gln Ala Pro Gly Lys Gly Leu Glu Trp Val
        35                  40                  45
Ala Tyr Ile Asp Ser Asp Gly Asp Asn Thr Tyr Tyr Arg Asp Ser Val
    50                  55                  60
Lys Gly Arg Phe Thr Ile Ser Arg Asp Asn Ala Lys Ser Ser Leu Tyr
65                  70                  75                  80
Leu Gln Met Asn Ser Leu Arg Ala Glu Asp Thr Ala Val Tyr Tyr Cys
                85                  90                  95
Thr Thr Gly Ile Val Arg Pro Phe Leu Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Ala Ala
225
```

<210> SEQ ID NO 63
<211> LENGTH: 684
<212> TYPE: DNA
<213> ORGANISM: Artificial Sequence
<220> FEATURE:

<223> OTHER INFORMATION: 1519gH20 Fab' heavy chain (V + human gamma-1 CH1 + hinge)

<400> SEQUENCE: 63

```
gaggttccgc tggtcgagtc tggaggcggg cttgtccagc tggagggag cctgcgtctc      60
tcttgtgcag tatctggctt cacgttctcc aactacggta tggtgtgggt cgtcaggct     120
ccaggtaaag gtctggaatg ggtggcgtat attgactccg acggcgacaa cacctactat    180
cgcgactctg tgaaaggtcg cttcaccatt tcccgcgata cgccaaatc agcctgtac      240
ctgcagatga acagcctgcg tgctgaagat actgcggtgt actattgcac cactggcatc    300
gtgcgtccgt ttctgtattg gggtcagggt accctcgtta ctgtctcgag cgcttctaca    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtcgacaaga agttgagcc caaatcttgt    660
gacaaaactc acacatgcgc cgcg                                            684
```

<210> SEQ ID NO 64
<211> LENGTH: 249
<212> TYPE: PRT
<213> ORGANISM: Artificial Sequence
<220> FEATURE:
<223> OTHER INFORMATION: 1519 gH20 Fab' heavy chain

<400> SEQUENCE: 64

```
Met Lys Lys Thr Ala Ile Ala Ile Ala Val Ala Leu Ala Gly Phe Ala
1               5                   10                  15

Thr Val Ala Gln Ala Glu Val Pro Leu Val Glu Ser Gly Gly Gly Leu
            20                  25                  30

Val Gln Pro Gly Gly Ser Leu Arg Leu Ser Cys Ala Val Ser Gly Phe
        35                  40                  45

Thr Phe Ser Asn Tyr Gly Met Val Trp Val Arg Gln Ala Pro Gly Lys
    50                  55                  60

Gly Leu Glu Trp Val Ala Tyr Ile Asp Ser Asp Gly Asp Asn Thr Tyr
65                  70                  75                  80

Tyr Arg Asp Ser Val Lys Gly Arg Phe Thr Ile Ser Arg Asp Asn Ala
                85                  90                  95

Lys Ser Ser Leu Tyr Leu Gln Met Asn Ser Leu Arg Ala Glu Asp Thr
            100                 105                 110

Ala Val Tyr Tyr Cys Thr Thr Gly Ile Val Arg Pro Phe Leu Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
```

His Lys Pro Ser Asn Thr Lys Val Asp Lys Lys Val Glu Pro Lys Ser
225                 230                 235                 240

Cys Asp Lys Thr His Thr Cys Ala Ala
                245

<210> SEQ ID NO 65
<211> LENGTH: 747
<212> TYPE: DNA
<213> ORGANISM: Artificial Sequence
<220> FEATURE:
<223> OTHER INFORMATION: 1519 gH20 Fab' heavy chain

<400> SEQUENCE: 65
atgaagaaga ctgctatagc aattgcagtg gcgctagctg gtttcgccac cgtggcgcaa    60
gctgaggttc cgctggtcga gtctggaggc gggcttgtcc agcctggagg gagcctgcgt   120
ctctcttgtg cagtatctgg cttcacgttc tccaactacg gtatggtgtg ggttcgtcag   180
gctccaggta aaggtctgga atgggtggcg tatattgact ccgacggcga caacacctac   240
tatcgcgact ctgtgaaagg tcgcttcacc atttccgcg ataacgccaa atccagcctg   300
tacctgcaga tgaacagcct gcgtgctgaa gatactgcgg tgtactattg caccactggc   360
atcgtgcgtc cgtttctgta ttggggtcag ggtaccctcg ttactgtctc gagcgcttct   420
acaaagggcc catcggtctt ccccctggca ccctcctcca agagcacctc tgggggcaca   480
gcggccctgg gctgcctggt caaggactac ttccccgaac cggtgacggt gtcgtggaac   540
tcaggcgccc tgaccagcgg cgtgcacacc ttcccggctg tcctacagtc ctcaggactc   600
tactccctca gcagcgtggt gaccgtgccc tccagcagct gggcaccca gacctacatc   660 tgcaacgtga atcacaagcc cagcaacacc aaggtcgaca gaaagttga gcccaaatct   720 tgtgacaaaa ctcacacatg cgccgcg                                       747

<210> SEQ ID NO 66
<211> LENGTH: 444
<212> TYPE: PRT
<213> ORGANISM: Artificial Sequence
<220> FEATURE:
<223> OTHER INFORMATION: 1519gH20 IgG4 heavy chain (V + human gamma-4P
      constant)

<400> SEQUENCE: 66

Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Thr Gly Ile Val Arg Pro Phe Leu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 67
<211> LENGTH: 1939
<212> TYPE: DNA
<213> ORGANISM: Artificial Sequence
<220> FEATURE:
<223> OTHER INFORMATION: 1519gH20 IgG4 heavy chain (V + human gamma-4P
      constant, exons)

<400> SEQUENCE: 67
gaggtaccac ttgtggaaag cggaggaggt cttgtgcagc tggaggaag tttacgtctc      60 tcttgtgctg tgtctggctt caccttctcc aattacggaa tggtctgggt cagacaagca     120
cctggaaagg gtcttgaatg ggtggcctat attgactctg acggggacaa cacctactat     180
cgggattccg tgaaaggacg cttcacaatc tcccgagata cgccaagag ctcactgtac      240

```
ctgcagatga atagcctgag agccgaggat actgccgtgt actattgcac aacgggaatc    300
gttaggcctt ttctgtactg gggacagggc accttggtta ctgtctcgag cgcttctaca    360
aagggcccat ccgtcttccc cctggcgccc tgctccagga gcacctccga gagcacagcc    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacgaagac ctacacctgc    600
aacgtagatc acaagcccag caacaccaag gtggacaaga gagttggtga gaggccagca    660
caggagggga gggtgtctgc tggaagccag gctcagccct cctgcctgga cgcaccccgg    720
ctgtgcagcc ccagcccagg gcagcaaggc atgcccatc tgtctcctca cccggaggcc    780
tctgaccacc ccactcatgc ccaggggagg ggtcttctgg attttccac caggctccgg    840
gcagccacag gctggatgcc cctaccccag gccctgcgca tacaggggca ggtgctgcgc    900
tcagacctgc caagagccat atccgggagg accctgcccc tgacctaagc ccaccccaaa    960
ggccaaactc tccactccct cagctcagac accttctctc ctcccagatc tgagtaactc   1020
ccaatcttct ctctgcagag tccaaatatg gtccccatg cccaccatgc ccaggtaagc   1080
caacccaggc ctcgccctcc agctcaaggc gggacaggtg ccctagagta gcctgcatcc   1140
agggacaggc cccagccggg tgctgacgca tccacctcca tctcttcctc agcacctgag   1200
ttcctggggg gaccatcagt cttcctgttc cccccaaaac ccaaggacac tctcatgatc   1260
tcccggaccc ctgaggtcac gtgcgtggtg gtggacgtga gccaggaaga ccccgaggtc   1320
cagttcaact ggtacgtgga tggcgtggag gtgcataatg ccaagacaaa gccgcgggag   1380
gagcagttca acagcacgta ccgtgtggtc agcgtcctca ccgtcctgca ccaggactgg   1440
ctgaacggca aggagtacaa gtgcaaggtc tccaacaaag gcctcccgtc ctccatcgag   1500
aaaaccatct ccaaagccaa aggtgggacc cacggggtgc gagggccaca tggacagagg   1560
tcagctcggc ccaccctctg ccctgggagt gaccgctgtg ccaacctctg tccctacagg   1620
gcagccccga gagccacagg tgtacaccct gccccatcc aggaggaga tgaccaagaa   1680
ccaggtcagc ctgacctgcc tggtcaaagg cttctacccc agcgacatcg ccgtggagtg   1740
ggagagcaat gggcagccgg agaacaacta caagaccacg cctcccgtgc tggactccga   1800
cggctccttc ttcctctaca gcaggctaac cgtggacaag agcaggtggc aggaggggaa   1860
tgtcttctca tgctccgtga tgcatgaggc tctgcacaac cactacacac agaagagcct   1920
ctccctgtct ctgggtaaa                                                 1939

<210> SEQ ID NO 68
<211> LENGTH: 347
<212> TYPE: PRT
<213> ORGANISM: Artificial Sequence
<220> FEATURE:
<223> OTHER INFORMATION: 1519gL20 FabFv light chain

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
            20                  25                  30

Ser Gly Lys Thr Tyr Leu Tyr Trp Leu Phe Gln Lys Pro Gly Lys Ala
        35                  40                  45

Pro Lys Arg Leu Ile Tyr Leu Val Ser Thr Leu Asp Ser Gly Ile Pro
    50                  55                  60
```

Ser Arg Phe Ser Gly Ser Gly Ser Gly Thr Glu Phe Thr Leu Thr Ile
 65                  70                  75                  80

Ser Ser Leu Gln Pro Glu Asp Phe Ala Thr Tyr Tyr Cys Leu Gln Gly
                 85                  90                  95

Thr His Phe Pro His Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Ser Gly Gly Gly
210                 215                 220

Ser Gly Gly Gly Ser Gly Gly Gly Ser Asp Ile Gln Met Thr
225                 230                 235                 240

Gln Ser Pro Ser Ser Val Ser Ala Ser Val Gly Asp Arg Val Thr Ile
                245                 250                 255

Thr Cys Gln Ser Ser Pro Ser Val Trp Ser Asn Phe Leu Ser Trp Tyr
            260                 265                 270

Gln Gln Lys Pro Gly Lys Ala Pro Lys Leu Leu Ile Tyr Glu Ala Ser
        275                 280                 285

Lys Leu Thr Ser Gly Val Pro Ser Arg Phe Ser Gly Ser Gly Ser Gly
290                 295                 300

Thr Asp Phe Thr Leu Thr Ile Ser Ser Leu Gln Pro Glu Asp Phe Ala
305                 310                 315                 320

Thr Tyr Tyr Cys Gly Gly Gly Tyr Ser Ser Ile Ser Asp Thr Thr Phe
                325                 330                 335

Gly Cys Gly Thr Lys Val Glu Ile Lys Arg Thr
            340                 345

<210> SEQ ID NO 69
<211> LENGTH: 1041
<212> TYPE: DNA
<213> ORGANISM: Artificial Sequence
<220> FEATURE:
<223> OTHER INFORMATION: 1519gL20 FabFv light chain

<400> SEQUENCE: 69
gatatccaga tgacccagag cccatctagc ttatccgctt ccgttggtga tcgcgtgaca      60
attacgtgta agagctccca atctctcgtg ggtgcaagtg caagaccta tctgtactgg     120 ctctttcaga agcctggcaa ggcaccaaaa cggctgatct atctggtgtc taccctggac   180
tctgggatac cgtcacgatt ttccggatct gggagcggaa ctgagttcac actcacgatt   240
tcatcgctgc aacccgagga ctttgctacc tactactgcc tgcaaggcac tcatttccct   300
cacactttcg gccaggggac aaaactcgaa atcaaacgta cggtagcggc ccatctgtc   360 ttcatcttcc cgccatctga tgagcagttg aaatctggaa ctgcctctgt tgtgtgcctg   420

-continued

```
ctgaataact tctatcccag agaggccaaa gtacagtgga aggtggataa cgccctccaa      480
tcgggtaact cccaggagag tgtcacagag caggacagca aggacagcac ctacagcctg      540
agcagcaccc tgacgctgtc taaagcagac tacgagaaac acaaagtgta cgcctgcgaa      600
gtcacccatc agggcctgag ctcaccagta acaaaaagtt ttaatagagg ggagtgtagc      660
ggtggcggtg gcagtggtgg gggaggctcc ggaggtggcg gttcagacat acaaatgacc      720
cagagtcctt catcggtatc cgcgtccgtt ggcgataggg tgactattac atgtcaaagc      780
tctcctagcg tctggagcaa ttttctatcc tggtatcaac agaaaccggg gaaggctcca      840
aaacttctga tttatgaagc ctcgaaactc accgtggag ttccgtcaag attcagtggc       900
tctggatcag ggacagactt cacgttgaca atcagttcgc tgcaaccaga ggactttgcg      960
acctactatt gtggtggagg ttacagtagc ataagtgata cgacatttgg gtgcggtact     1020
aaggtggaaa tcaaacgtac c                                               1041
```

<210> SEQ ID NO 70
<211> LENGTH: 367
<212> TYPE: PRT
<213> ORGANISM: Artificial Sequence
<220> FEATURE:
<223> OTHER INFORMATION: 1519gL20 FabFv light chain

<400> SEQUENCE: 70

```
Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Val Gly Ala Ser Gly Lys Thr Tyr Leu Tyr Trp Leu Phe Gln Lys
    50                  55                  60

Pro Gly Lys Ala Pro Lys Arg Leu Ile Tyr Leu Val Ser Thr Leu Asp
65                  70                  75                  80

Ser Gly Ile Pro Ser Arg Phe Ser Gly Ser Gly Ser Gly Thr Glu Phe
                85                  90                  95

Thr Leu Thr Ile Ser Ser Leu Gln Pro Glu Asp Phe Ala Thr Tyr Tyr
            100                 105                 110

Cys Leu Gln Gly Thr His Phe Pro His Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys Ser
225                 230                 235                 240

Gly Gly Gly Gly Ser Gly Gly Gly Ser Gly Gly Gly Gly Ser Asp
                245                 250                 255
```

Ile Gln Met Thr Gln Ser Pro Ser Val Ser Ala Ser Val Gly Asp
            260                 265                 270

Arg Val Thr Ile Thr Cys Gln Ser Pro Ser Val Trp Ser Asn Phe
            275                 280                 285

Leu Ser Trp Tyr Gln Gln Lys Pro Gly Lys Ala Pro Lys Leu Leu Ile
            290                 295                 300

Tyr Glu Ala Ser Lys Leu Thr Ser Gly Val Pro Ser Arg Phe Ser Gly
305                 310                 315                 320

Ser Gly Ser Gly Thr Asp Phe Thr Leu Thr Ile Ser Ser Leu Gln Pro
                325                 330                 335

Glu Asp Phe Ala Thr Tyr Tyr Cys Gly Gly Tyr Ser Ser Ile Ser
            340                 345                 350

Asp Thr Thr Phe Gly Cys Gly Thr Lys Val Glu Ile Lys Arg Thr
            355                 360                 365

<210> SEQ ID NO 71
<211> LENGTH: 1101
<212> TYPE: DNA
<213> ORGANISM: Artificial Sequence
<220> FEATURE:
<223> OTHER INFORMATION: 1519gL20 FabFv light chain

<400> SEQUENCE: 71

| | |
|---|---:|
| atgtctgtcc ccacccaagt cctcggactc ctgctactct ggcttacaga tgccagatgc | 60 |
| gatatccaga tgacccagag cccatctagc ttatccgctt ccgttggtga tcgcgtgaca | 120 |
| attacgtgta agagctccca atctctcgtg ggtgcaagtg caagaccta tctgtactgg | 180 |
| ctctttcaga agcctggcaa ggcaccaaaa cggctgatct atctggtgtc taccttgac | 240 |
| tctgggatac cgtcacgatt ttccggatct gggagcggaa ctgagttcac actcacgatt | 300 |
| tcatcgctgc aacccgagga ctttgctacc tactactgcc tgcaaggcac tcatttccct | 360 |
| cacactttcg gccagggac aaaactcgaa atcaaacgta cggtagcggc cccatctgtc | 420 |
| ttcatcttcc cgccatctga tgagcagttg aaatctggaa ctgcctctgt tgtgtgcctg | 480 |
| ctgaataact tctatcccag agaggccaaa gtacagtgga aggtggataa cgccctccaa | 540 |
| tcgggtaact cccaggagag tgtcacagag caggacagca aggacagcac ctacagcctg | 600 |
| agcagcaccc tgacgctgtc taaagcagac tacgagaaac acaaagtgta cgcctgcgaa | 660 |
| gtcacccatc agggcctgag ctcaccagta acaaaaagtt ttaatagagg ggagtgtagc | 720 |
| ggtggcggtg gcagtggtgg gggaggctcc ggaggtggcg gttcagacat acaaatgacc | 780 |
| cagagtcctt catcggtatc cgcgtccgtt ggcgataggg tgactattac atgtcaaagc | 840 |
| tctcctagcg tctggagcaa ttttctatcc tggtatcaac agaaaccggg gaaggctcca | 900 |
| aaacttctga tttatgaagc ctcgaaactc accagtggag ttccgtcaag attcagtggc | 960 |
| tctggatcag ggacagactt cacgttgaca atcagttcgc tgcaaccaga ggactttgcg | 1020 |
| acctactatt gtggtggagg ttacagtagc ataagtgata cgacatttgg gtgcggtact | 1080 |
| aaggtggaaa tcaaacgtac c | 1101 |

<210> SEQ ID NO 72
<211> LENGTH: 357
<212> TYPE: PRT
<213> ORGANISM: Artificial Sequence
<220> FEATURE:
<223> OTHER INFORMATION: 1519gH20 FabFv heavy chain

<400> SEQUENCE: 72

Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Thr Gly Ile Val Arg Pro Phe Leu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Ser Gly Gly Gly
    210                 215                 220

Gly Ser Gly Gly Gly Gly Thr Gly Gly Gly Gly Ser Glu Val Gln Leu
225                 230                 235                 240

Leu Glu Ser Gly Gly Gly Leu Val Gln Pro Gly Gly Ser Leu Arg Leu
                245                 250                 255

Ser Cys Ala Val Ser Gly Ile Asp Leu Ser Asn Tyr Ala Ile Asn Trp
            260                 265                 270

Val Arg Gln Ala Pro Gly Lys Cys Leu Glu Trp Ile Gly Ile Ile Trp
        275                 280                 285

Ala Ser Gly Thr Thr Phe Tyr Ala Thr Trp Ala Lys Gly Arg Phe Thr
    290                 295                 300

Ile Ser Arg Asp Asn Ser Lys Asn Thr Val Tyr Leu Gln Met Asn Ser
305                 310                 315                 320

Leu Arg Ala Glu Asp Thr Ala Val Tyr Tyr Cys Ala Arg Thr Val Pro
                325                 330                 335

Gly Tyr Ser Thr Ala Pro Tyr Phe Asp Leu Trp Gly Gln Gly Thr Leu
            340                 345                 350

Val Thr Val Ser Ser
        355

<210> SEQ ID NO 73
<211> LENGTH: 1071
<212> TYPE: DNA
<213> ORGANISM: Artificial Sequence
<220> FEATURE:
<223> OTHER INFORMATION: 1519gH20 FabFv heavy chain

<400> SEQUENCE: 73

```
gaggtaccac ttgtggaaag cggaggaggt cttgtgcagc ctggaggaag tttacgtctc      60
tcttgtgctg tgtctggctt caccttctcc aattacggaa tggtctgggt cagacaagca     120
cctggaaagg tcttgaatg gtggcctat attgactctg acggggacaa cacctactat      180
cgggattccg tgaaaggacg cttcacaatc tcccgagata cgccaagag ctcactgtac      240
ctgcagatga atagcctgag agccgaggat actgccgtgt actattgcac aacgggaatc     300
gttaggcctt ttctgtactg gggacaggc accttggtta ctgtctcgag cgcgtccaca     360
aagggcccat cggtcttccc cctggcaccc tcctccaaga gcacctctgg gggcacagcg     420
gccctgggct gcctggtcaa ggactacttc cccgaaccag tgacggtgtc gtggaactca     480
ggtgccctga ccagcggcgt tcacaccttc ccggctgtcc tacagtcttc aggactctac     540
tccctgagca gcgtggtgac cgtgccctcc agcagcttgg gcacccagac ctacatctgc     600
aacgtgaatc acaagcccag caacaccaag gtcgataaga agttgagcc caaatcttgt     660
agtggaggtg ggggctcagg tggaggcggg accggtggag gtggcagcga ggttcaactg     720
cttgagtctg gaggaggcct agtccagcct ggagggagcc tgcgtctctc ttgtgcagta     780
agcggcatcg acctgagcaa ttacgccatc aactgggtga caagctcc ggggaagtgt     840
ttagaatgga tcggtataat atgggccagt gggacgacct tttatgctac atgggcgaaa     900
ggaaggttta caattagccg ggacaatagc aaaaacaccg tgtatctcca aatgaactcc     960
ttgcgagcag aggacacggc ggtgtactat tgtgctcgca ctgtcccagg ttatagcact    1020
gcaccctact cgatctgtg gggacaaggg accctggtga ctgtttcaag t             1071
```

<210> SEQ ID NO 74
<211> LENGTH: 376
<212> TYPE: PRT
<213> ORGANISM: Artificial Sequence
<220> FEATURE:
<223> OTHER INFORMATION: 1519gH20 FabFv heavy chain

<400> SEQUENCE: 74

```
Met Glu Trp Ser Trp Val Phe Leu Phe Phe Leu Ser Val Thr Thr Gly
1               5                   10                  15

Val His Ser Glu Val Pro Leu Val Glu Ser Gly Gly Gly Leu Val Gln
            20                  25                  30

Pro Gly Gly Ser Leu Arg Leu Ser Cys Ala Val Ser Gly Phe Thr Phe
        35                  40                  45

Ser Asn Tyr Gly Met Val Trp Val Arg Gln Ala Pro Gly Lys Gly Leu
    50                  55                  60

Glu Trp Val Ala Tyr Ile Asp Ser Asp Gly Asp Asn Thr Tyr Tyr Arg
65                  70                  75                  80

Asp Ser Val Lys Gly Arg Phe Thr Ile Ser Arg Asp Asn Ala Lys Ser
                85                  90                  95

Ser Leu Tyr Leu Gln Met Asn Ser Leu Arg Ala Glu Asp Thr Ala Val
            100                 105                 110

Tyr Tyr Cys Thr Thr Gly Ile Val Arg Pro Phe Leu Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175
```

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Ser
225                 230                 235                 240

Gly Gly Gly Gly Ser Gly Gly Gly Thr Gly Gly Gly Ser Glu
                245                 250                 255

Val Gln Leu Leu Glu Ser Gly Gly Gly Leu Val Gln Pro Gly Gly Ser
        260                 265                 270

Leu Arg Leu Ser Cys Ala Val Ser Gly Ile Asp Leu Ser Asn Tyr Ala
    275                 280                 285

Ile Asn Trp Val Arg Gln Ala Pro Gly Lys Cys Leu Glu Trp Ile Gly
        290                 295                 300

Ile Ile Trp Ala Ser Gly Thr Thr Phe Tyr Ala Thr Trp Ala Lys Gly
305                 310                 315                 320

Arg Phe Thr Ile Ser Arg Asp Asn Ser Lys Asn Thr Val Tyr Leu Gln
                325                 330                 335

Met Asn Ser Leu Arg Ala Glu Asp Thr Ala Val Tyr Tyr Cys Ala Arg
            340                 345                 350

Thr Val Pro Gly Tyr Ser Thr Ala Pro Tyr Phe Asp Leu Trp Gly Gln
        355                 360                 365

Gly Thr Leu Val Thr Val Ser Ser
        370                 375

<210> SEQ ID NO 75
<211> LENGTH: 22
<212> TYPE: PRT
<213> ORGANISM: Artificial Sequence
<220> FEATURE:
<223> OTHER INFORMATION: Wild type Tsp 5'

<400> SEQUENCE: 75

Met Asn Met Phe Phe Arg Leu Thr Ala Leu Ala Gly Leu Leu Ala Ile
1               5                   10                  15

Ala Gly Gln Thr Phe Ala
            20

<210> SEQ ID NO 76
<211> LENGTH: 66
<212> TYPE: DNA
<213> ORGANISM: Artificial Sequence
<220> FEATURE:
<223> OTHER INFORMATION: Wild type Tsp 5'

<400> SEQUENCE: 76
atgaacatgt tttttaggct taccgcgtta gctggcctgc ttgcaatagc aggccagacc    60
ttcgct                                                              66

<210> SEQ ID NO 77
<211> LENGTH: 19
<212> TYPE: PRT
<213> ORGANISM: Artificial Sequence
<220> FEATURE:
<223> OTHER INFORMATION: Mutated Tsp 5' fragment

<400> SEQUENCE: 77

```
Met Asn Ser Phe Leu Gly Leu Pro Arg Leu Ala Cys Leu Gln Gln Ala
1               5                   10                  15

Arg His Leu

<210> SEQ ID NO 78
<211> LENGTH: 66
<212> TYPE: DNA
<213> ORGANISM: Artificial Sequence
<220> FEATURE:
<223> OTHER INFORMATION: Mutated Tsp 5' fragment

<400> SEQUENCE: 78
atgaattcgt ttttaggctt accgcgttag ctggcctgct tgcaatagca ggccagacat    60
taattg                                                                66

<210> SEQ ID NO 79
<211> LENGTH: 20
<212> TYPE: PRT
<213> ORGANISM: Artificial
<220> FEATURE:
<223> OTHER INFORMATION: Mutated delta ptr (protease III) 5'

<400> SEQUENCE: 79

Ile Pro Arg Ser Thr Trp Phe Lys Ala Leu Leu Leu Val Ala Leu
1               5                   10                  15

Trp Ala His Cys
            20

<210> SEQ ID NO 80
<211> LENGTH: 66
<212> TYPE: DNA
<213> ORGANISM: Artificial
<220> FEATURE:
<223> OTHER INFORMATION: Mutated delta ptr (protease III) 5'

<400> SEQUENCE: 80
tgaattcccc gcagcacctg gttcaaagca ttattgttgt tagttgccct ttgggcacat    60
taatgt                                                                66

<210> SEQ ID NO 81
<211> LENGTH: 21
<212> TYPE: PRT
<213> ORGANISM: Artificial
<220> FEATURE:
<223> OTHER INFORMATION: Wild-type ptr (protease III) 5'

<400> SEQUENCE: 81

Met Pro Arg Ser Thr Trp Phe Lys Ala Leu Leu Leu Leu Val Ala Leu
1               5                   10                  15

Trp Ala Pro Leu Ser
            20

<210> SEQ ID NO 82
<211> LENGTH: 66
<212> TYPE: DNA
<213> ORGANISM: Artificial
<220> FEATURE:
<223> OTHER INFORMATION: Wild-type ptr (protease III) 5'

<400> SEQUENCE: 82
tgaatgcccc gcagcacctg gttcaaagca ttattgttgt tagttgccct ttgggcaccc    60
ttaagt                                                                66
```

```
<210> SEQ ID NO 83
<211> LENGTH: 11
<212> TYPE: PRT
<213> ORGANISM: Artificial
<220> FEATURE:
<223> OTHER INFORMATION: Wild type DegP

<400> SEQUENCE: 83

Asp Ala Ala Ile Asn Arg Gly Asn Ser Gly Gly
1               5                   10

<210> SEQ ID NO 84
<211> LENGTH: 33
<212> TYPE: DNA
<213> ORGANISM: Artificial
<220> FEATURE:
<223> OTHER INFORMATION: Wild type DegP

<400> SEQUENCE: 84
gatgcagcga tcaaccgtgg taactccggt ggt                              33

<210> SEQ ID NO 85
<211> LENGTH: 11
<212> TYPE: PRT
<213> ORGANISM: Artificial
<220> FEATURE:
<223> OTHER INFORMATION: Mutated DegP S210A

<400> SEQUENCE: 85

Asp Ala Ala Ile Asn Arg Gly Asn Ala Gly Gly
1               5                   10

<210> SEQ ID NO 86
<211> LENGTH: 33
<212> TYPE: DNA
<213> ORGANISM: Artificial
<220> FEATURE:
<223> OTHER INFORMATION: Mutated DegP S210A

<400> SEQUENCE: 86
gatgcagcga ttaatcgtgg taacgccggt ggt                              33
```

RECOMBINANT BACTERIAL HOST CELL FOR PROTEIN EXPRESSION

CROSS REFERENCE TO RELATED APPLICATIONS

This application a continuation of U.S. application Ser. No. 14/400,068, filed Nov. 10, 2014, now U.S. Pat. No. 9,951,365, which is the U.S. national phase of International Application No. PCT/EP2013/059803, filed May 13, 2013, which claims priority to Great Britain Patent Application No. 1208367.1, filed May 14, 2012, the disclosures of each of which are explicitly incorporated by reference in their entirety herein.

The Sequence Listing for this application is labeled "Seq-List.txt" which was created on Apr. 9, 2016 and is 118 KB. The entire content of the sequence listing is incorporated herein by reference in its entirety.

The invention relates to a recombinant bacterial host strain, particularly E. coli. The invention also relates to a method for producing a protein of interest in such a cell.

BACKGROUND OF THE INVENTION

Bacterial cells, such as E. coli, are commonly used for producing recombinant proteins. There are many advantages to using bacterial cells, such as E. coli, for producing recombinant proteins particularly due to the versatile nature of bacterial cells as host cells allowing the gene insertion via plasmids. E. coli have been used to produce many recombinant proteins including human insulin.

Despite the many advantages to using bacterial cells to produce recombinant proteins, there are still significant limitations including the difficulty of producing protease sensitive proteins. Proteases play an important role in turning over old, damaged or mis-folded proteins in the E. coli periplasm and cytoplasm. Bacterial proteases act to degrade the recombinant protein of interest, thereby often significantly reducing the yield of active protein.

A number of bacterial proteases have been identified. In E. coli proteases including Protease III (ptr), DegP, OmpT, Tsp, prlC, ptrA, ptrB, pepA-T, tsh, espc, eatA, clpP and lon have been identified.

Tsp (also known as Prc) is a 60 kDa periplasmic protease. The first known substrate of Tsp was Penicillin-binding protein-3 (PBP3) (Determination of the cleavage site involved in C-terminal processing of penicillin-binding protein 3 of Escherichia coli; Nagasawa H, Sakagami Y, Suzuki A, Suzuki H, Hara H, Hirota Y. J Bacteriol. 1989 November; 171(11):5890-3 and Cloning, mapping and characterization of the Escherichia coli Tsp gene which is involved in C-terminal processing of penicillin-binding protein 3; Hara H, Yamamoto Y, Higashitani A, Suzuki H, Nishimura Y. J Bacteriol. 1991 August; 173 (15):4799-813) but it was later discovered that the Tsp was also able to cleave phage tail proteins and, therefore, it was renamed as Tail Specific Protease (Tsp) (Silber et al., Proc. Natl. Acad. Sci. USA, 89: 295-299 (1992)). Silber et al. (Deletion of the prc(tsp) gene provides evidence for additional tail-specific proteolytic activity in Escherichia coli K-12; Silber, K. R., Sauer, R. T.; Mol Gen Genet 1994 242:237-240) describes a prc deletion strain (KS1000) wherein the mutation was created by replacing a segment of the prc gene with a fragment comprising a Kan$^r$ marker.

The reduction of Tsp (prc) activity is desirable to reduce the proteolysis of proteins of interest. However, it was found that cells lacking protease prc show thermosensitive growth at low osmolarity. Hara et al isolated thermoresistant revertants containing extragenic suppressor (spr) mutations (Hara et al., Microbial Drug Resistance, 2: 63-72 (1996)). Spr is an 18 kDa membrane bound periplasmic protease and the substrates of spr are Tsp and peptidoglycans in the outer membrane involved in cell wall hydrolysis during cell division. The spr gene is designated as UniProtKB/Swiss-Prot P0AFV4 (SPR_ECOLI).

Improved protease deficient strains comprising a mutant spr gene have been described. Chen et al describes the construction of E. coli strains carrying different combinations of mutations in prc (Tsp) and another protease, DegP, created by amplifying the upstream and downstream regions of the gene and ligating these together on a vector comprising selection markers and a sprW174R mutation (High-level accumulation of a recombinant antibody fragment in the periplasm of Escherichia coli requires a triple-mutant (ΔDegP Δprc sprW174R) host strain (Chen C, Snedecor B, Nishihara J C, Joly J C, McFarland N, Andersen D C, Battersby J E, Champion K M. Biotechnol Bioeng. 2004 Mar. 5; 85(5):463-74). The combination of the ΔDegP, Δprc and sprW174R mutations were found to provide the highest levels of antibody light chain, antibody heavy chain and F(ab')2-LZ. EP1341899 discloses an E. coli strain that is deficient in chromosomal DegP and prc encoding proteases DegP and Prc, respectively, and harbors a mutant spr gene that encodes a protein that suppresses growth phenotypes exhibited by strains harboring prc mutants.

Other improved protease deficient strains containing mutations in both Tsp and spr have been described in WO2011/086136.

Strains disclosed in WO02/48376 are lac$^-$ and cannot grow in cultures where thymidine, fucose or maltose are employed as the carbon source. This can be a severe disadvantage for strains intended for use on a commercial scale. There may be further disadvantages associated with the strains, for example the lack of production of alkaline phosphatase. The latter is a periplasmic protein involved in phosphate utilization from culture media.

Certain proteins exhibit peptidyl-prolyl isomerase and/or isomerase activity and/or chaperone activity and have been found to provide advantageous properties when employed in cell lines employed for recombinant protein expression.

The present invention provides new bacterial strains carrying both Tsp and spr mutations and at least one gene encoding a protein or proteins capable of facilitating protein folding which provide advantageous means for producing recombinant proteins.

SUMMARY OF THE INVENTION

In a first aspect of the present invention there is provided a recombinant gram-negative bacterial cell comprising:
  a. a mutant spr gene encoding a spr protein having a mutation at one or more amino acids selected from D133, H145, H157, N31, R62, I70, Q73, C94, S95, V98, Q99, R100, L108, Y115, V135, L136, G140, R144 and G147 and
  b. a gene or genes capable of expressing or overexpressing one or more proteins capable of facilitating protein folding, such as FkpA, Skp, SurA, PPiA and PPiD
wherein the cell has reduced Tsp protein activity compared to a wild-type cell.

In one embodiment of the present invention there is provided a recombinant gram-negative bacterial cell encoding:

a. a mutant spr gene encoding a spr protein having a mutation at one or more amino acids selected from D133, H145, H157, N31, R62, I70, Q73, C94, S95, V98, Q99, R100, L108, Y115, V135, L136, G140, R144 and G147, b. a gene or genes capable of expressing or overexpressing one or more proteins capable of facilitating protein folding, such as FkpA, Skp, SurA, PPiA and PPiD, c. a gene capable of expressing a protein of interest, for example an antibody or binding fragment thereof wherein the cell has reduced Tsp protein activity compared to a wild-type cell and the remainder of cell genomic DNA is isogenic with the wild-type cell from which the recombinant cell was derived.

In one embodiment, the cell's genome is isogenic to a wild-type bacterial cell except for the mutated spr gene, the modification required to reduce Tsp protein activity compared to a wild-type cell and the gene or genes expressing a protein capable of facilitating protein folding.

In a second aspect the present invention provides a recombinant gram-negative bacterial cell having reduced Tsp protein activity compared to a wild-type cell and comprising a mutant spr gene encoding a spr protein, wherein the cell's genome is isogenic to a wild-type bacterial cell except for the modification required to reduce Tsp protein activity compared to a wild-type cell, the mutated spr gene and the gene or genes introduced for expressing a protein capable of facilitating protein folding.

The cells provided by the first and second aspects of the present invention show advantageous growth and protein production phenotypes.

In a third aspect, the present invention provides a method for producing a protein of interest comprising expressing the protein of interest in a recombinant gram-negative bacterial cell as defined above.

In a fourth aspect, the present invention also extends to proteins expressed from the process described herein.

BRIEF DESCRIPTION OF THE DRAWINGS

FIG. 2 shows the results of feed rate variation experiments at post induction feed rates 5.4, 6.0 and 7.0 g/h, for MXE016 the majority of the additional Fab' made at higher feed rates was lost in the supernatant.

FIGS. 3A-3B show cell viability (3A) and Fab' titres (3B) for MXE016+/−FkpA.

FIG. 4 shows the primary recovery data for 20 L pilot scale production.

FIG. 5 shows the primary recovery on SDS-PAGE stained gel under non-reducing conditions of a 20 L pilot scale production. Other than the FkpA related bands the protein profile appears very similar between the two strains.

FIG. 6 shows a His-tag western blot under non-reducing conditions for a 20 L pilot scale process. Full length FkpA detected and corresponds to the ~30 kDa band and no signal was detected in MXE016 alone as expected.

FIGS. 7A-7C show various mutations in various genes.

FIG. 7D shows a diagrammatic representation of the creation of a vector comprising a polynucleotide sequence encoding a light chain of an antibody (LC), a heavy chain of an antibody (HC), a FkpA polynucleotide sequence and/or Skp polynucleotide.

FIGS. 8A-8O show various polynucleotide and amino acid sequences.

BRIEF DESCRIPTION OF THE SEQUENCES

Figure 1:
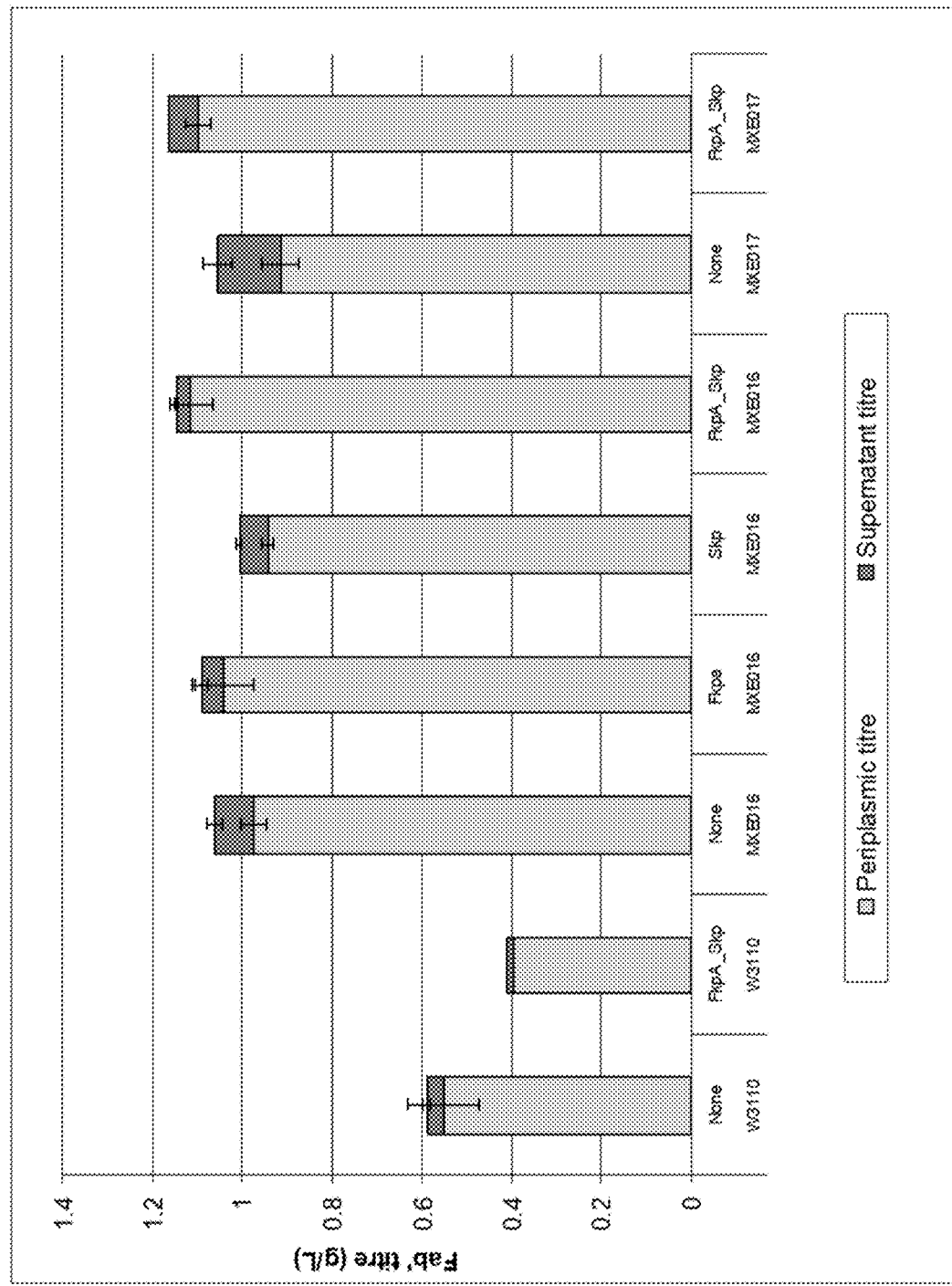
FIG. 1 shows the results of fermentations on the 5 L scale performed with various combinations of host cells and "chaperone". W3110 is a wild-type *E coli* strain. The various combinations were: wild type with no chaperone; wild-type with FkpA and Skp; MXE016 mutant spr and A Tsp as published in WO2011/086136; MXE016 and FkpA; MXE016 and Skp; MXE016 and FkpA and Skp; MXE017 disclosed in WO2011/086136; MXE017 and FkpA and Skp.

SEQ ID NO:1 is the DNA sequence of the wild-type Tsp gene including the 6 nucleotides ATGAAC upstream of the start codon.

SEQ ID NO:2 is the amino acid sequence of the wild-type Tsp protein.

SEQ ID NO:3 is the DNA sequence of a mutated knock-out Tsp gene including the 6 nucleotides ATGAAT upstream of the start codon.

SEQ ID NO:4 is the DNA sequence of the wild-type Protease III gene.

SEQ ID NO:5 is the amino acid sequence of the wild-type Protease III protein.

SEQ ID NO:6 is the DNA sequence of a mutated knock-out Protease III gene.

SEQ ID NO:7 is the DNA sequence of the wild-type DegP gene.

SEQ ID NO:8 is the amino acid sequence of the wild-type DegP protein.

SEQ ID NO:9 is the DNA sequence of a mutated DegP gene.

SEQ ID NO:10 is the amino acid sequence of a mutated DegP protein.

SEQ ID NO: 11 is the sequence of the 5' oligonucleotide primer for the region of the mutated DegP gene comprising the Ase I restriction site.

SEQ ID NO: 12 is the sequence of the 3' oligonucleotide primer for the region of the mutated DegP gene comprising the Ase I restriction site.

SEQ ID NO: 13 is the sequence of the 5' oligonucleotide primer for the region of the mutated Tsp gene comprising the Ase I restriction site.

SEQ ID NO: 14 is the sequence of the 3' oligonucleotide primer for the region of the mutated Protease III gene comprising the Ase I restriction site.

SEQ ID NO: 15 is the sequence of the 5' oligonucleotide primer for the region of the mutated Protease III gene comprising the Ase I restriction site.

SEQ ID NO: 16 is the sequence of the 3' oligonucleotide primer for the region of the mutated Tsp gene comprising the Ase I restriction site.

SEQ ID NO: 17 is the DNA sequence of the wild-type spr gene.

SEQ ID NO: 18 is the sequence of the wild-type spr gene including the signal sequence which is the first 26 amino acid residues.

SEQ ID NO: 19 is the sequence of the non-mutated spr gene without the signal sequence.

SEQ ID NO: 20 is the nucleotide sequence of a mutated OmpT sequence comprising D210A and H212A mutations.

SEQ ID NO: 21 is the amino acid sequence of a mutated OmpT sequence comprising D210A and H212A mutations.

SEQ ID NO: 22 is the nucleotide sequence of a mutated knockout OmpT sequence.

SEQ ID NO: 23 shows the sequence of the OmpA oligonucleotide adapter.

SEQ ID NO: 24 shows the oligonucleotide cassette encoding intergenic sequence 1 (IGS1) for *E. coli* Fab expression.

SEQ ID NO: 25 shows the oligonucleotide cassette encoding intergenic sequence 2 (IGS2) for *E. coli* Fab expression.

SEQ ID NO: 26 shows the oligonucleotide cassette encoding intergenic sequence 3 (IGS3) for *E. coli* Fab expression.

SEQ ID NO: 27 shows the oligonucleotide cassette encoding intergenic sequence 4 (IGS4) for *E. coli* Fab expression.

SEQ ID NO: 28 is the DNA sequence of the wild-type FkpA gene.

SEQ ID NO: 29 is the protein sequence of the wild-type FkpA gene.

SEQ ID NO: 30 is the DNA sequence of the FkpA his tagged gene.

SEQ ID NO: 31 is the protein sequence of the FkpA his tagged gene.

SEQ ID NO: 32 is the DNA sequence of the wild-type skp gene.

SEQ ID NO: 33 is the protein sequence of the wild-type skp gene.

SEQ ID NO: 34 is the DNA sequence of the skp his tagged gene.

SEQ ID NO: 35 is the protein sequence of the skp his tagged gene.

SEQ ID NO: 36 to 74 show various amino acid and DNA sequences of FcRn antibodies or fragments thereof, which are suitable for expression in the cell line of the present invention. In particular SEQ ID NO: 50 is the amino acid sequence of the light chain variable region of an anti-FcRn antibody light chain 1519gH20 and SEQ ID NO:58 is the amino acid sequence of the heavy chain variable region of an anti-FcRn antibody heavy chain 1519gH20.

DETAILED DESCRIPTION OF THE PREFERRED EMBODIMENTS OF THE INVENTION

The present inventors have provided improved recombinant gram-negative bacterial cells suitable for expressing a recombinant protein of interest.

In one embodiment the protein is an antibody or binding fragment thereof, in particular a therapeutic antibody.

In particular, the inventors have provided improved recombinant gram-negative bacterial cells suitable for expressing a recombinant protein of interest by incorporating one or more gene or genes, encoding a protein for facilitating protein folding, into gram-negative bacterial cells carrying a mutated Tsp gene and a mutated spr gene.

In one embodiment the gene or genes, encoding the protein for facilitating protein folding, are integrated into the cells genome, for example to provide a stable cell line. In one embodiment a recombinant protein for expression (such as a therapeutic protein) is transfected into a stable cell line to provide expression of the desired recombinant protein.

In one embodiment the gene or genes, encoding a protein for facilitating protein folding, are provided on one or more plasmids, for example the plasmids are transiently transfected into a cell to provide a cell line of the present disclosure.

In one embodiment the gene or genes, encoding a protein for facilitating protein folding, are provided on a plasmid also containing the coding sequence for a recombinant protein of interest.

In one embodiment the gene or genes, encoding a protein for facilitating protein folding, are provided on a plasmid that does not contain the coding sequence for a recombinant protein of interest.

In one embodiment the invention provides new strains having improved cell growth phenotype compared to wild-type bacterial cells and cells carrying just a mutated Tsp gene or a mutated Tsp and a mutated spr gene.

The cells of the present invention possess many advantages. The inventors have surprisingly found that cells according to the present disclosure may exhibit increased cell viability compared to a wild-type cell or a cell comprising a mutated Tsp gene and mutated spr gene.

Cell viability is of particular importance in practical terms because cells that are not viable tend to lyse and create DNA debris in the culture. This DNA debris increases the, difficulty, cost and expense of purifying the desired protein. Therefore minimizing the DNA debris from lysed non-viable cells is a significant issue in manufacturing recombinant proteins efficiently, see for example U.S. Pat. No. 6,258,560.

Cell viability may be measured by any one of a number of routine techniques, for example employing a fluorescent dye and FACS analysis or similar.

Specifically, the cells according to the disclosure generally exhibit reduced cell lysis phenotype compared to cells carrying a mutated Tsp gene and a mutated spr gene.

Furthermore, the new strains may reduce leakage of protein from the cells and allow prolonged periplasmic accumulation compared to cells carrying a mutated Tsp gene and mutated spr gene. This is particularly important because, for example where total expression levels of target protein are similar but more protein is accumulated into the periplasm or less protein is accumulated in the supernatant because the strain is less leaky then cells with these less leaky properties will generally be more suitable for plant scale production because they facilitate protein recovery.

Further, the cells according to the present disclosure may exhibit increased yield of a protein of interest compared to a wild-type bacterial cell or a cell comprising a mutated Tsp gene and a mutated spr gene in the absence of a genes or genes encoding a protein such as FkpA. The improved protein yield may be the periplasmic protein yield and/or the supernatant protein yield. In one embodiment the cells of the present invention show improved periplasmic protein yield compared to a cell carrying a mutated Tsp gene and mutated spr gene due to reduced leakage from the cell.

The recombinant bacterial cells may be capable of faster rate of production of a protein of interest and, therefore, the same quantity of a protein of interest may be produced in a shorter time compared to a wild-type bacterial cell or a cell comprising a mutated Tsp gene and a mutated spr gene. The faster rate of production of a protein of interest may be especially significant over the initial period of growth of the cell, for example over the first 5, 10, 20 or 30 hours post induction of protein expression.

The cells according to the present invention preferably express a maximum yield in the periplasm and/or media of approximately 1.0 g/L, 1.5 g/L, 1.8 g/L, 2.0 g/L, 2.4 g/L, 2.5 g/L, 3.0 g/L, 3.5 g/L or 4.0 g/L of a protein of interest.

Additionally the expression of a protein or proteins that facilitates folding further optimizes the expression by maximizing the protein provided with proper folding. The skilled person is well aware that appropriate folding is essential for biological function and thus isolating protein with the desired folding is vitally important. This is particularly important when the protein is expressed in a gram-negative cell because the protein expressed will not be natural to cell and thus the cell may not automatically express the protein with the appropriate folding. Inappropriate folding may express itself as aggregation or other impurities. The isolation of the desired protein may require extensive purification, which has cost implications and may also result in a low yield of the desired protein. Maximizing the amount of properly folded protein expressed minimizes the amount of purification required and may optimize the useable yield and thus is advantageous.

Advantages associated with the expression of a protein that facilitates folding include one or more of the following: Higher titre (e.g. increased to about 1.05 g/L in comparison to wild-type 0.5 g/L); Higher viability at harvest (e.g. >95%); Increased titre with increasing feed rate (better prospects for process development); Higher titre at commercial production scales such as 20 L scale and higher viability at harvest; and Easier clarification of extract, in particular at 20 L scale.

The cells provided by the present invention have reduced protease activity of Tsp compared to a wild-type cell, which may reduce proteolysis of a protein of interest, particularly proteins of interest which are proteolytically sensitive to Tsp. Therefore, the cells provided by the present invention may provide higher yield of the intact proteins, preferably of the protein of interest and a lower yield, or preferably no proteolytic fragments of proteins, preferably of the protein of interest, compared to a wild-type bacterial cell.

In one embodiment of the invention, the cells carry only the minimal mutations to the genome required to introduce the modifications according to the present disclosure. The bacterial cell may only differ from a wild-type bacterial cell by the one or more mutations to the spr gene and the modification required to reduce Tsp protein activity compared to a wild-type cell because for example the gene or genes encoding a protein for facilitating protein folding may be introduced transiently into the cell, such as on a plasmid. In one embodiment the cells do not carry any other mutations which may have deleterious effects on the cell's growth and/or ability to express a protein of interest.

Accordingly, one or more of the recombinant host cells of the present invention may exhibit improved protein expression and/or improved growth characteristics compared to cells comprising further genetically engineered mutations to the genomic sequence. The cells provided by the present invention are also more suitable for use to produce therapeutic proteins compared to cells comprising further disruptions to the cell genome.

The skilled person would easily be able to test a candidate cell clone to see if it has the desired yield of a protein of interest using methods well known in the art including a fermentation method, ELISA and protein G HPLC. Suitable fermentation methods are described in Humphreys D P, et al. (1997). Formation of dimeric Fabs in *E. coli*: effect of hinge size and isotype, presence of interchain disulphide bond, Fab' expression levels, tail piece sequences and growth conditions. *J. IMMUNOL. METH.* 209: 193-202; Backlund E. Reeks D. Markland K. Weir N. Bowering L. Larsson G. Fedbatch design for periplasmic product retention in *Escherichia coli*, Journal Article. Research Support, Non-U.S. Gov't Journal of Biotechnology. 135(4):358-65, 2008 Jul. 31; Champion K M. Nishihara J C. Joly J C. Arnott D. Similarity of the *Escherichia coli* proteome upon completion of different biopharmaceutical fermentation processes. [Journal Article] Proteomics. 1(9):1133-48, 2001 September; and Horn U. Strittmatter W. Krebber A. Knupfer U. Kujau M. Wenderoth R. Muller K. Matzku S. Pluckthun A. Riesenberg D. High volumetric yields of functional dimeric miniantibodies in *Escherichia coli*, using an optimized expression vector and high-cell-density fermentation under non-limited growth conditions, Journal Article. Research Support, Non-U.S. Gov't Applied Microbiology & Biotechnology. 46(5-6):524-32, 1996 December. The skilled person would also easily be able to test secreted protein to see if the protein is correctly folded using methods well known in the art, such as protein G HPLC, circular dichroism, NMR, X-Ray crystallography and epitope affinity measurement methods.

The present invention will now be described in more detail.

The terms "protein" and "polypeptide" are used interchangeably herein, unless the context indicates otherwise. "Peptide" is intended to refer to 10 or less amino acids.

The terms "polynucleotide" includes a gene, DNA, cDNA, RNA, mRNA etc. unless the context indicates otherwise.

'Reduced activity' as employed herein refers to 'lower levels of enzymatic activity, such as Tsp enzymic activity in comparison to the corresponding enzymic activity in a wild type strain when measured under comparable conditions in a suitable assay. In one embodiment the reduced activity is 50% or less, 40% or less, 30% or less, 20% or less, 10% or less or 5% or less of the enzymic activity of a wild-type comparator. In one embodiment the analysis to determine the levels of enzymic activity are performed concomitantly when the results are to be employed in a direct comparison.

Direct comparison as employed herein refers to where the numerical value of two or more results are compared for the purpose of evaluating if there is reduced activity as defined herein or ranking the activity results obtained from an assay.

As used herein, the term "comprising" in context of the present specification should be interpreted as "including".

Wild-type cell as employed herein employed interchangeably with non-mutated cell or control cell.

The non-mutated cell or control cell in the context of the present invention means a cell of the same type as the recombinant gram-negative cell of the invention wherein the cell has not been modified to carry the above reduce Tsp protein activity and to carry the mutant spr gene. For example, a non-mutated cell may be a wild-type cell and may be derived from the same population of host cells as the cells of the invention before modification to introduce any mutations.

The expressions "cell", "cell line", "cell culture" and "strain" are used interchangeably.

The expression "phenotype of a cell comprising a mutated Tsp gene" in the context of the present invention means the phenotype exhibited by a cell having a mutant Tsp gene. Typically cells comprising a mutant Tsp gene may lyse, especially at high cell densities. The lysis of these cells causes any recombinant protein to leak into the supernatant. Cells carrying mutated Tsp gene may also show thermosensitive growth at low osmolarity. For example, the cells exhibit no or reduced growth rate or the cells die in hypotonic media at a high temperature, such as at 40° C. or more.

The term "isogenic" in the context of the present invention means that the genome of the cell of the present invention has substantially the same or the same genomic sequence compared to the wild-type cell from which the cell is derived except for a mutated spr gene and the modification required to reduce Tsp protein activity compared to a wild-type cell. In this embodiment the genome of the cell comprises no further non-naturally occurring or genetically engineered mutations. In one embodiment the cell according to the present invention may have substantially the same genomic sequence compared to the wild-type cell except for the mutated spr gene and the modification required to reduce Tsp protein activity compared to a wild-type cell taking into account any naturally occurring mutations which may occur. In one embodiment, the cell according to the present invention may have exactly the same genomic sequence compared to the wild-type cell except for the mutated spr gene and the modification required to reduce Tsp protein activity compared to a wild-type cell.

The term "wild-type" in the context of the present invention means a strain of a gram-negative bacterial cell as it may occur in nature or may be isolated from the environment, which does not carry any genetically engineered mutations. An example of a wild-type strain of *E. coli* is W3110, such as W3110 K-12 strain.

Any suitable gram-negative bacterium may be used as the parental cell for producing the recombinant cell of the present invention. Suitable gram-negative bacterium include *Salmonella typhimurium, Pseudomonas fluorescens, Erwinia carotovora, Shigella, Klebsiella pneumoniae, Legionella pneumophila, Pseudomonas aeruginosa, Acinetobacter baumannii* and *E. coli*. Preferably the parental cell is *E. coli*. Any suitable strain of *E. coli* may be used in the present invention but preferably a wild-type W3110 strain, such as K-12 W3110, is used.

A drawback associated with the protease deficient bacterial strains previously created and used to express recombinant proteins is that they comprise additional mutations of genes involved in cell metabolism and DNA replication such as, for example phoA, fhuA, lac, rec, gal, ara, arg, thi and pro in *E. coli* strains. These mutations may have many deleterious effects on the host cell including effects on cell growth, stability, recombinant protein expression yield and toxicity. Strains having one or more of these genomic mutations, particularly strains having a high number of these mutations, may exhibit a loss of fitness which reduces bacterial growth rate to a level which is not suitable for industrial protein production. Further, any of the above genomic mutations may affect other genes in cis and/or in trans in unpredictable harmful ways thereby altering the strain's phenotype, fitness and protein profile. Further, the use of heavily mutated cells is not generally suitable for producing recombinant proteins for commercial use, particularly therapeutics, because such strains generally have defective metabolic pathways and hence may grow poorly or not at all in minimal or chemically defined media.

In one embodiment a cell according to the present invention is isogenic to a wild-type bacterial cell except for the mutated spr gene and the modification required to reduce Tsp protein activity compared to a wild-type cell. Only minimal mutations are made to the cell's genome to introduce the mutations. The cells do not carry any other mutations which may have deleterious effects on the cell's growth and/or ability to express a protein of interest. Accordingly, one or more of the recombinant host cells of the present invention may exhibit improved protein expression and/or improved growth characteristics compared to cells comprising further genetically engineered mutations to the genomic sequence. The cells provided by the present invention are also more suitable for use in the production of therapeutic proteins compared to cells comprising further disruptions to the cell genome.

In a preferred embodiment, the cell is isogenic to a wild-type *E. coli* cell, such as strain W3110, except for the mutated spr gene and the modification required to reduce Tsp protein activity compared to a wild-type cell.

The cell of the present invention may further differ from a wild-type cell by comprising a polynucleotide encoding the protein of interest. The polynucleotide sequence encoding the protein of interest may be exogenous or endogenous. The polynucleotide encoding the protein of interest may be contained within a suitable expression vector transformed into the cell and/or integrated into the host cell's genome. In the embodiment where the polynucleotide encoding the protein of interest is inserted into the host's genome, the cell of the present invention will also differ from a wild-type cell due to the inserted polynucleotide sequence encoding the protein of interest. Preferably the polynucleotide is in an expression vector in the cell thereby causing minimal disruption to the host cell's genome.

The spr protein is an *E. coli* membrane bound periplasmic protease.

The wild-type amino acid sequence of the spr protein is shown in SEQ ID NO:21 with the signal sequence at the N-terminus and in SEQ ID NO:22 without the signal sequence of 26 amino acids (according to UniProt Accession Number POAFV4). The amino acid numbering of the spr protein sequence in the present invention includes the signal sequence. Accordingly, the amino acid 1 of the spr protein is the first amino acid (Met) shown in SEQ ID NO: 21.

The mutated spr gene is preferably the cell's chromosomal spr gene.

The mutated spr gene encodes a spr protein capable of suppressing the phenotype of a cell further comprising a mutated Tsp gene. Cells carrying a mutated Tsp gene may have a good cell growth rate but one limitation of these cells is their tendency to lyse, especially at high cell densities. Accordingly the phenotype of a cell comprising a mutated Tsp gene is a tendency to lyse, especially at high cell densities. Cells carrying a mutated Tsp gene also show thermosensitive growth at low osmolarity. However, the spr mutations carried by the cells of the present invention, when introduced into a cell having reduced Tsp activity suppress the reduced Tsp phenotype and, therefore, the cell exhibits reduced lysis, particularly at a high cell density. The growth phenotype of a cell may be easily measured by a person skilled in the art during shake flask or high cell density fermentation technique. The suppression of the cell lysis phenotype may be been seen from the improved growth rate and/or recombinant protein production, particularly in the periplasm, exhibited by a cell carrying spr mutant and having reduced Tsp activity compared to a cell carrying the Tsp mutant and a wild-type spr.

The cells according to the present invention comprise a mutant spr gene encoding a spr protein having a mutation at one or more amino acids selected from N31, R62, I70, Q73, C94, S95, V98, Q99, R100, L108, Y115, D133, V135, L136, G140, R144, H145, G147 and H157, preferably a mutation at one or more amino acids selected from C94, S95, V98, Y115, D133, V135, H145, G147 and H157. In this embodiment, the spr protein preferably does not have any further mutations.

The mutation of one or more of the above amino acids may be any suitable missense mutation to one, two or three of the nucleotides encoding the amino acid. The mutation changes the amino acid residue to any suitable amino acid which results in a mutated spr protein capable of suppressing the phenotype of a cell comprising a mutated Tsp gene. The missense mutation may change the amino acid to one which is a different size and/or has different chemical properties compared to the wild-type amino acid.

In one embodiment the mutant spr gene encodes an spr protein having one or more mutations selected from C94A, S95F, V98E, Y115F, D133A, V135D or G, H145A, G147C and H157A.

In one embodiment the mutation is to one, two or three of the catalytic triad of amino acid residues of C94, H145, and H157 (Solution NMR Structure of the NlpC/P60 Domain of Lipoprotein Spr from *Escherichia coli* Structural Evidence for a Novel Cysteine Peptidase Catalytic Triad, Biochemistry, 2008, 47, 9715-9717).

Accordingly, the mutated spr gene may comprise: a mutation to C94; or a mutation to H145; or a mutation to H157; or a mutation to C94 and H145; or a mutation to C94 and H157; or a mutation to H145 and H157; or a mutation to C94, H145 and H157.

In this embodiment, the spr protein preferably does not have any further mutations.

One, two or three of C94, H145 and H157 may be mutated to any suitable amino acid which results in a spr protein capable of suppressing the phenotype of a cell comprising a mutated Tsp gene. For example, one, two or three of C94, H145, and H157 may be mutated to a small amino acid such as Gly or Ala. Accordingly, the spr protein may have one, two or three of the mutations C94A, H145A and H157A. In one embodiment, the spr gene comprises the missense mutation C94A, which has been found to produce a spr protein capable of suppressing the phenotype of a cell comprising a mutated Tsp gene. In another embodiment, the spr gene comprises the missense mutation H145A, which has been found to produce a spr protein capable of suppressing the phenotype of a cell comprising a mutated Tsp gene.

The designation for a substitution mutant herein consists of a letter followed by a number followed by a letter. The first letter designates the amino acid in the wild-type protein. The number refers to the amino acid position where the amino acid substitution is being made, and the second letter designates the amino acid that is used to replace the wild-type amino acid.

In one embodiment the mutant spr protein comprises a mutation at one or more amino acids selected from N31, R62, I70, Q73, S95, V98, Q99, R100, L108, Y115, D133, V135, L136, G140, R144 and G147, preferably a mutation at one or more amino acids selected from S95, V98, Y115, D133, V135 and G147. In this embodiment, the spr protein preferably does not have any further mutations. Accordingly, the mutated spr gene may comprise: a mutation to N31; or a mutation to R62; or a mutation to I70; or a mutation to Q73; or a mutation to S95; or a mutation to V98; or a mutation to Q99; or a mutation to R100; or a mutation to L108; or a mutation to Y115; or a mutation to D133; or a mutation to V135; or a mutation to L136; or a mutation to G140; or a mutation to R144; or a mutation to G147.

In one embodiment the mutant spr protein comprises multiple mutations to amino acids: S95 and Y115; or N31, Q73, R100 and G140; or Q73, R100 and G140; or R100 and G140; or Q73 and G140; or Q73 and R100; or R62, Q99 and R144; or Q99 and R144.

One or more of the amino acids N31, R62, I70, Q73, S95, V98, Q99, R100, L108, Y115, D133, V135, L136, G140, R144 and G147 may be mutated to any suitable amino acid which results in a spr protein capable of suppressing the phenotype of a cell comprising a mutated Tsp gene. For example, one or more of N31, R62, I70, Q73, S95, V98, Q99, R100, L108, Y115, D133, V135, L136, G140 and R144 may be mutated to a small amino acid such as Gly or Ala.

In one embodiment the spr protein comprises one or more of the following mutations: N31Y, R62C, I70T, Q73R, S95F, V98E, Q99P, R100G, L108S, Y115F, D133A, V135D or V135G, L136P, G140C, R144C and G147C. In one embodiment the spr protein comprises one or more of the following mutations: S95F, V98E, Y115F, D133A, V135D or V135G and G147C. In this embodiment, the spr protein preferably does not have any further mutations.

In one embodiment the spr protein has one mutation selected from N31Y, R62C, I70T, Q73R, S95F, V98E, Q99P, R100G, L108S, Y115F, D133A, V135D or V135G, L136P, G140C, R144C and G147C. In this embodiment, the spr protein preferably does not have any further mutations.

In a further embodiment the spr protein has multiple mutations selected from: S95F and Y115F; N31Y, Q73R, R100G and G140C; Q73R, R100G and G140C; R100G and G140C; Q73R and G140C; Q73R and R100G; R62C, Q99P and R144C; or Q99P and R144C.

In one embodiment the mutated spr gene encodes a spr protein having a mutation C94A.

In one embodiment the mutated spr gene encodes a spr protein having a mutation V103E.

In one embodiment the mutated spr gene encodes a spr protein having a mutation D133A.

In one embodiment the mutated spr gene encodes a spr protein having a mutation V135D.

In one embodiment the mutated spr gene encodes a spr protein having a mutation V135A.

In one embodiment the mutated spr gene encodes a spr protein having a mutation H145A.

In one embodiment the mutated spr gene encodes a spr protein having a mutation G147C.

In one embodiment the mutated spr gene encodes a spr protein having a mutation H157A.

In one embodiment the mutant spr gene encodes a spr protein having a mutation selected from H145A, H157A and D133A.

In one embodiment of the present invention, any suitable mutation or mutations may be made to the spr gene which results in a spr protein capable of suppressing the phenotype of a cell comprising a mutated Tsp gene. Preferably, the spr protein may have one or more of the following mutations: N31Y, R62C, I70T, Q73R, C94A, S95F, V98E, Q99P, R100G, L108S, Y115F, D133A, V135D, V135G, L136P, G140C, R144C, H145A, G147C, H157A and W174R. In one embodiment the spr protein does not comprise the mutation W174R. Preferably, the spr gene comprises one or more mutations discussed above.

The cells according to the present invention have reduced Tsp protein activity compared to a wild-type cell. The expression "reduced Tsp protein activity compared to a wild-type cell" means that the Tsp activity of the cell is reduced compared to the Tsp activity of a wild-type cell. The cell may be modified by any suitable means to reduce the activity of Tsp.

In one embodiment the reduced Tsp activity is from modification of the endogenous polynucleotide encoding Tsp and/or associated regulatory expression sequences. The modification may reduce or stop Tsp gene transcription and translation or may provide an expressed Tsp protein having reduced protease activity compared to the wild-type Tsp protein.

In one embodiment an associated regulatory expression sequence is modified to reduce Tsp expression. For example, the promoter for the Tsp gene may be mutated to prevent expression of the gene.

In a preferred embodiment the cells according to the present invention carry a mutated Tsp gene encoding a Tsp protein having reduced protease activity or a knockout mutated Tsp gene.

Preferably the chromosomal Tsp gene is mutated.

As used herein, "Tsp gene" means a gene encoding protease Tsp (also known as Prc) which is a periplasmic protease capable of acting on Penicillin-binding protein-3 (PBP3) and phage tail proteins. The sequence of the wild-type Tsp gene is shown in SEQ ID NO: 1 and the sequence of the wild-type Tsp protein is shown in SEQ ID NO: 2.

Reference to the mutated Tsp gene or mutated Tsp gene encoding Tsp, refers to either a mutated Tsp gene encoding a Tsp protein having reduced protease activity or a knockout mutated Tsp gene, unless otherwise indicated.

The expression "mutated Tsp gene encoding a Tsp protein having reduced protease activity" in the context of the present invention means that the mutated Tsp gene does not have the full protease activity compared to the wild-type non-mutated Tsp gene.

Preferably, the mutated Tsp gene encodes a Tsp protein having 50% or less, 40% or less, 30% or less, 20% or less, 10% or less or 5% or less of the protease activity of a wild-type non-mutated Tsp protein. More preferably, the mutated Tsp gene encodes a Tsp protein having no protease activity. In this embodiment the cell is not deficient in chromosomal Tsp i.e. the Tsp gene sequence has not been deleted or mutated to prevent expression of any form of Tsp protein.

Any suitable mutation may be introduced into the Tsp gene in order to produce a protein having reduced protease activity. The protease activity of a Tsp protein expressed from a gram-negative bacterium may be easily tested by a person skilled in the art by any suitable method in the art, such as the method described in Keiler et al (Identification of Active Site Residues of the Tsp Protease* THE JOURNAL OF BIOLOGICAL CHEMISTRY Vol. 270, No. 48, Issue of December 1, pp. 28864-28868, 1995 Kenneth C. Keiler and Robert T. Sauer) wherein the protease activity of Tsp was tested.

Tsp has been reported in Keiler et al (supra) as having an active site comprising residues S430, D441 and K455 and residues G375, G376, E433 and T452 are important for maintaining the structure of Tsp. Keiler et al (supra) reports findings that the mutated Tsp genes S430A, D441A, K455A, K455H, K455R, G375A, G376A, E433A and T452A had no detectable protease activity. It is further reported that the mutated Tsp gene S430C displayed about 5-10% wild-type activity. Accordingly, the Tsp mutation to produce a protein having reduced protease activity may comprise a mutation, such as a missense mutation to one or more of residues S430, D441, K455, G375, G376, E433 and T452. Preferably the Tsp mutation to produce a protein having reduced protease activity may comprise a mutation, such as a missense mutation to one, two or all three of the active site residues S430, D441 and K455.

Accordingly the mutated Tsp gene may comprise: a mutation to S430; or a mutation to D441; or a mutation to K455; or a mutation to S430 and D441; or a mutation to S430 and K455; or a mutation to D441 and K455; or a mutation to S430, D441 and K455.

One or more of S430, D441, K455, G375, G376, E433 and T452 may be mutated to any suitable amino acid which results in a protein having reduced protease activity. Examples of suitable mutations are S430A, S430C, D441A, K455A, K455H, K455R, G375A, G376A, E433A and T452A. The mutated Tsp gene may comprise one, two or three mutations to the active site residues, for example the gene may comprise: S430A or S430C; and/or D441A; and/or K455A or K455H or K455R.

Preferably, the Tsp gene has the point mutation S430A or S430C.

The expression "knockout mutated Tsp gene" in the context of the present invention means that the gene comprises one or more mutations which prevents expression of the Tsp protein encoded by the wild-type gene to provide a cell deficient in Tsp protein. The knockout gene may be partially or completely transcribed but not translated into the encoded protein. The knockout mutated Tsp gene may be mutated in any suitable way, for example by one or more deletion, insertion, point, missense, nonsense and frameshift mutations, to cause no expression of the protein. For example, the gene may be knocked out by insertion of a foreign DNA sequence, such as an antibiotic resistance marker, into the gene coding sequence.

In a preferred embodiment the Tsp gene is not mutated by insertion of a foreign DNA sequence, such as an antibiotic resistance marker, into the gene coding sequence. In this embodiment the Tsp gene may comprise a mutation to the gene start codon and/or one or more stop codons positioned downstream of the gene start codon and upstream of the gene stop codon thereby preventing expression of the Tsp protein. The mutation to the start codon may be a missense mutation of one, two or all three of the nucleotides of the start codon. Alternatively or additionally the start codon may be mutated by an insertion or deletion frameshift mutation. The Tsp gene comprises two ATG codons at the 5' end of the coding sequence, one or both of the ATG codons may be mutated by a missense mutation. The Tsp gene may be mutated at the second ATG codon (codon 3) to TCG. The Tsp gene may alternatively or additionally comprise one or more stop codons positioned downstream of the gene start codon and upstream of the gene stop codon. Preferably the knockout mutated Tsp gene comprises both a missense mutation to the start codon and one or more inserted stop codons. In a preferred embodiment the Tsp gene is mutated to delete "T" from the fifth codon thereby causing a frameshift resulting in stop codons at codons 11 and 16. In a preferred embodiment the Tsp gene is mutated to insert an Ase I restriction site to create a third in-frame stop codon at codon 21.

In a preferred embodiment the knockout mutated Tsp gene has the DNA sequence of SEQ ID NO: 3, which includes the 6 nucleotides ATGAAT upstream of the start codon. In one embodiment the mutated Tsp gene has the DNA sequence of nucleotides 7 to 2048 of SEQ ID NO:3.

In the present invention the cells also carry one or more genes capable of expressing or overexpressing one or more proteins capable of facilitating protein folding. Examples include proteins such as FkpA, Skp, SurA, PPiA and PPiD.

In one embodiment the protein for facilitating protein folding is FkpA, Skp or a combination thereof.

In one embodiment the protein for facilitating protein folding is selected from FkpA or a combination of FkpA and Skp.

FkpA is a peptidyl-prolyl cis-trans isomerase with the Swiss-Prot number P45523.

Skp is chaperon protein with the Swiss-Prot number P0AEU7.

The protein for facilitating protein folding may be encoded by a gene in the cells genome or transiently transfected therein, for example on a plasmid or a combination of the same, as appropriate.

In one embodiment the recombinant gram-negative bacterial cell does not comprises a recombinant polynucleotide encoding DsbC.

In one embodiment of the present invention the recombinant gram-negative bacterial cell further comprises a mutated DegP gene encoding a DegP protein having chaperone activity and reduced protease activity and/or a mutated ptr gene, wherein the mutated ptr gene encodes a Protease III protein having reduced protease activity or is a knockout mutated ptr gene and/or a mutated OmpT gene, wherein the mutated OmpT gene encodes an OmpT protein having reduced protease activity or is a knockout mutated OmpT gene.

Preferably in this embodiment the cell's genome is isogenic to a wild-type bacterial cell except for the above mutations.

As used herein, "DegP" means a gene encoding DegP protein (also known as HtrA), which has dual function as a chaperone and a protease (Families of serine peptidases; Rawlings N D, Barrett A J. Methods Enzymol. 1994; 244: 19-61). The sequence of the non-mutated DegP gene is shown in SEQ ID NO: 7 and the sequence of the non-mutated DegP protein is shown in SEQ ID NO: 8.

At low temperatures DegP functions as a chaperone and at high temperatures DegP has a preference to function as a protease (A Temperature-Dependent Switch from Chaperone to Protease in a Widely Conserved Heat Shock Protein. Cell, Volume 97, Issue 3, Pages 339-347. Spiess C, Beil A, Ehrmann M) and The proteolytic activity of the HtrA (DegP) protein from *Escherichia coli* at low temperatures, Skorko-Glonek J et al Microbiology 2008, 154, 3649-3658).

In the embodiments where the cell comprises the DegP mutation the DegP mutation in the cell provides a mutated DegP gene encoding a DegP protein having chaperone activity but not full protease activity.

The expression "having chaperone activity" in the context of the present invention means that the mutated DegP protein has the same or substantially the same chaperone activity compared to the wild-type non-mutated DegP protein. Preferably, the mutated DegP gene encodes a DegP protein having 50% or more, 60% or more, 70% or more, 80% or more, 90% or more or 95% or more of the chaperone activity of a wild-type non-mutated DegP protein. More preferably, the mutated DegP gene encodes a DegP protein having the same chaperone activity compared to wild-type DegP.

The expression "having reduced protease activity" in the context of the present invention means that the mutated DegP protein does not have the full protease activity compared to the wild-type non-mutated DegP protein. Preferably, the mutated DegP gene encodes a DegP protein having 50% or less, 40% or less, 30% or less, 20% or less, 10% or less or 5% or less of the protease activity of a wild-type non-mutated DegP protein. More preferably, the mutated DegP gene encodes a DegP protein having no protease activity. The cell is not deficient in chromosomal DegP i.e. the DegP gene sequences has not been deleted or mutated to prevent expression of any form of DegP protein.

Any suitable mutation may be introduced into the DegP gene in order to produce a protein having chaperone activity and reduced protease activity. The protease and chaperone activity of a DegP protein expressed from a gram-negative bacterium may be easily tested by a person skilled in the art by any suitable method such as the method described in Spiess et al wherein the protease and chaperone activities of DegP were tested on MalS, a natural substrate of DegP (A Temperature-Dependent Switch from Chaperone to Protease in a Widely Conserved Heat Shock Protein. Cell, Volume 97, Issue 3, Pages 339-347. Spiess C, Beil A, Ehrmann M) and also the method described in The proteolytic activity of the HtrA (DegP) protein from *Escherichia coli* at low temperatures, Skorko-Glonek J et al Microbiology 2008, 154, 3649-3658.

DegP is a serine protease and has an active center consisting of a catalytic triad of amino acid residues of His105, Asp135 and Ser210 (Families of serine peptidases, Methods Enzymol., 1994, 244:19-61 Rawlings N and Barrett A). The DegP mutation to produce a protein having chaperone activity and reduced protease activity may comprise a mutation, such as a missense mutation to one, two or three of His105, Asp135 and Ser210.

Accordingly, the mutated DegP gene may comprise: a mutation to His105; or a mutation to Asp135; or a mutation to Ser210; or a mutation to His105 and Asp135; or a mutation to His105 and Ser210; or a mutation to Asp135 and Ser210; or a mutation to His105, Asp135 and Ser210.

One, two or three of His105, Asp135 and Ser210 may be mutated to any suitable amino acid which results in a protein having chaperone activity and reduced protease activity. For example, one, two or three of His105, Asp135 and Ser210 may be mutated to a small amino acid such as Gly or Ala. A further suitable mutation is to change one, two or three of His105, Asp135 and Ser210 to an amino acid having opposite properties such as Asp135 being mutated to Lys or Arg, polar His105 being mutated to a non-polar amino acid such as Gly, Ala, Val or Leu and small hydrophilic Ser210 being mutated to a large or hydrophobic residue such as Val, Leu, Phe or Tyr. Preferably, the DegP gene comprises the point mutation S210A, as shown in FIG. 7C, which has been found to produce a protein having chaperone activity but not protease activity (A Temperature-Dependent Switch from Chaperone to Protease in a Widely Conserved Heat Shock Protein. Cell, Volume 97, Issue 3, Pages 339-347. Spiess C, Beil A, Ehrmann M).

DegP has two PDZ domains, PDZ1 (residues 260-358) and PDZ2 (residues 359-448), which mediate protein-protein interaction (A Temperature-Dependent Switch from Chaperone to Protease in a Widely Conserved Heat Shock Protein. Cell, Volume 97, Issue 3, Pages 339-347. Spiess C, Beil A, Ehrmann M). In one embodiment of the present invention the degP gene is mutated to delete PDZ1 domain and/or PDZ2 domain. The deletion of PDZ1 and PDZ2 results in complete loss of protease activity of the DegP protein and lowered chaperone activity compared to wild-type DegP protein whilst deletion of either PDZ1 or PDZ2 results in 5% protease activity and similar chaperone activity compared to wild-type DegP protein (A Temperature-Dependent Switch from Chaperone to Protease in a Widely Conserved Heat Shock Protein. Cell, Volume 97, Issue 3, Pages 339-347. Spiess C, Beil A, Ehrmann M).

The mutated DegP gene may also comprise a silent non-naturally occurring restriction site, such as Ase I in order to aid in identification and screening methods, for example as shown in FIG. 7C.

The preferred sequence of the mutated DegP gene comprising the point mutation S210A and an Ase I restriction marker site is provided in SEQ ID NO: 9 and the encoded protein sequence is shown in SEQ ID NO: 10.

In the embodiments of the present invention wherein the cell comprises a mutated DegP gene encoding a DegP protein having chaperone activity and reduced protease activity, one or more of the cells provided by the present invention may provide improved yield of correctly folded proteins from the cell relative to mutated cells wherein the DegP gene has been mutated to knockout DegP preventing DegP expression, such as chromosomal deficient DegP. In a cell comprising a knockout mutated DegP gene preventing DegP expression, the chaperone activity of DegP is lost completely whereas in the cell according to the present invention the chaperone activity of DegP is retained whilst the full protease activity is lost. In these embodiments, one or more cells according to the present invention have a lower protease activity to prevent proteolysis of the protein whilst maintaining the chaperone activity to allow correct folding and transportation of the protein in the host cell.

In these embodiments, one or more cells according to the present invention may have improved cell growth compared to cells carrying a mutated knockout DegP gene preventing DegP expression. Without wishing to be bound by theory improved cell growth may be exhibited due to the DegP protease retaining chaperone activity which may increase capacity of the cell to process all proteins which require chaperone activity. Accordingly, the production of correctly folded proteins necessary for the cell's growth and reproduction may be increased in one or more of the cells of the present invention compared to cells carrying a DegP knockout mutation thereby improving the cellular pathways regulating growth. Further, known DegP protease deficient strains are generally temperature-sensitive and do not typically grow at temperatures higher than about 28° C. However, the cells according to the present invention are not temperature-sensitive and may be grown at temperatures of 28° C. or higher, including temperatures of approximately 30° C. to approximately 37° C., which are typically used for industrial scale production of proteins from bacteria.

In one embodiment of the present invention the cell carries a mutated ptr gene. As used herein, "ptr gene" means a gene encoding Protease III, a protease which degrades high molecular weight proteins. The sequence of the non-mutated ptr gene is shown in SEQ ID NO: 4 and the sequence of the non-mutated Protease III protein is shown in SEQ ID NO: 5.

Reference to the mutated ptr gene or mutated ptr gene encoding Protease III, refers to either a mutated ptr gene encoding a Protease III protein having reduced protease activity or a knockout mutated ptr gene, unless otherwise indicated.

The expression "mutated ptr gene encoding a Protease III protein having reduced protease activity" in the context of the present invention means that the mutated ptr gene does not have the full protease activity compared to the wild-type non-mutated ptr gene.

Preferably, the mutated ptr gene encodes a Protease III having 50% or less, 40% or less, 30% or less, 20% or less, 10% or less or 5% or less of the protease activity of a wild-type non-mutated Protease III protein. More preferably, the mutated ptr gene encodes a Protease III protein having no protease activity. In this embodiment the cell is not deficient in chromosomal ptr i.e. the ptr gene sequence has not been deleted or mutated to prevent expression of any form of Protease III protein.

Any suitable mutation may be introduced into the ptr gene in order to produce a Protease III protein having reduced protease activity. The protease activity of a Protease III protein expressed from a gram-negative bacterium may be easily tested by a person skilled in the art by any suitable method in the art.

The expression "knockout mutated ptr gene" in the context of the present invention means that the gene comprises one or more mutations thereby causing no expression of the protein encoded by the gene to provide a cell deficient in the protein encoded by the knockout mutated gene. The knockout gene may be partially or completely transcribed but not translated into the encoded protein. The knockout mutated ptr gene may be mutated in any suitable way, for example by one or more deletion, insertion, point, missense, nonsense and frameshift mutations, to cause no expression of the protein. For example, the gene may be knocked out by insertion of a foreign DNA sequence, such as an antibiotic resistance marker, into the gene coding sequence.

In a preferred embodiment the gene is not mutated by insertion of a foreign DNA sequence, such as an antibiotic resistance marker, into the gene coding sequence. Preferably the Protease III gene comprise a mutation to the gene start codon and/or one or more stop codons positioned downstream of the gene start codon and upstream of the gene stop codon thereby preventing expression of the Protease III protein.

A mutation to the target knockout gene start codon causes loss of function of the start codon and thereby ensures that the target gene does not comprise a suitable start codon at the start of the coding sequence. The mutation to the start codon may be a missense mutation of one, two or all three of the nucleotides of the start codon. Alternatively or additionally the start codon may be mutated by an insertion or deletion frameshift mutation.

In a preferred embodiment the ptr gene is mutated to change the ATG start codon to ATT.

The knockout mutated ptr gene may alternatively or additionally comprise one or more stop codons positioned downstream of the gene start codon and upstream of the gene stop codon. Preferably the knockout mutated ptr gene comprises both a missense mutation to the start codon and one or more inserted stop codons.

The one or more inserted stop codons are preferably in-frame stop codons. However the one or more inserted stop codons may alternatively or additionally be out-of-frame stop codons. One or more out-of-frame stop codons may be required to stop translation where an out-of-frame start codon is changed to an in-frame start codon by an insertion or deletion frameshift mutation. The one or more stop codons may be introduced by any suitable mutation including a nonsense point mutation and a frameshift mutation. The one or more stop codons are preferably introduced by a frameshift mutation and/or an insertion mutation, preferably by replacement of a segment of the gene sequence with a sequence comprising a stop codon. For example an Ase I restriction site may be inserted, which comprises the stop codon TAA.

In a preferred embodiment the ptr gene is mutated to insert an in-frame stop codon by insertion of an Ase I restriction site, as shown in FIG. 7A. In a preferred embodiment the knockout mutated ptr gene has the DNA sequence of SEQ ID NO: 6.

The above described knockout mutations are advantageous because they cause minimal or no disruption to the chromosomal DNA upstream or downstream of the target knockout gene site and do not require the insertion and retention of foreign DNA, such as antibiotic resistance markers, which may affect the cell's suitability for expressing a protein of interest, particularly therapeutic proteins. Accordingly, one or more of the cells according to the present invention may exhibit improved growth characteristics and/or protein expression compared to cells wherein the protease gene has been knocked out by insertion of foreign DNA into the gene coding sequence.

In one embodiment the cells according to the present invention carry a mutated OmpT gene. As used herein, "OmpT gene" means a gene encoding protease OmpT (outer membrane protease T) which is an outer membrane protease. The sequence of the wild-type non-mutated OmpT gene is SWISS-PROT P09169.

Reference to a mutated OmpT gene or mutated OmpT gene encoding OmpT, refers to either a mutated OmpT gene encoding a OmpT protein having reduced protease activity or a knockout mutated OmpT gene, unless otherwise indicated.

The expression "mutated OmpT gene encoding an OmpT protein having reduced protease activity" in the context of the present invention means that the mutated OmpT gene does not have the full protease activity compared to the wild-type non-mutated OmpT gene. The mutated OmpT gene may encode an OmpT protein having 50% or less, 40% or less, 30% or less, 20% or less, 10% or less or 5% or less of the protease activity of a wild-type non-mutated OmpT protein. The mutated OmpT gene may encode an OmpT protein having no protease activity. In this embodiment the cell is not deficient in chromosomal OmpT i.e. the OmpT gene sequence has not been deleted or mutated to prevent expression of any form of OmpT protein.

Any suitable mutation may be introduced into the OmpT gene in order to produce a protein having reduced protease activity. The protease activity of a OmpT protein expressed from a gram-negative bacterium may be easily tested by a person skilled in the art by any suitable method in the art, such as the method described in Kramer et al (Identification of essential acidic residues of outer membrane protease OmpT supports a novel active site, FEBS Letters 505 (2001) 426-430) and Dekker et al (Substrate Specitificity of the Integral Membrane Protease OmpT Determined by Spatially Addressed Peptide Libraries, Biochemistry 2001, 40, 1694-1701).

OmpT has been reported in Kramer et al (Identification of active site serine and histidine residues in *Escherichia coli* outer membrane protease OmpT FEBS Letters 2000 468, 220-224) discloses that substitution of serines, histidines and acidic residues by alanines results in ~10-fold reduced activity for Glu27, Asp97, Asp208 or His101, ~500-fold reduced activity for Ser99 and 10000-fold reduced activity for Asp83, Asp85, Asp210 or His212. Vandeputte-Rutten et al (Crystal Structure of the Outer Membrane Protease OmpT from *Escherichia coli* suggests a novel catalytic site, The EMBO Journal 2001, Vol 20 No 18 5033-5039) as having an active site comprising a Asp83-Asp85 pair and a His212-Asp210 pair. Further Kramer et al (Lipopolysaccharide regions involved in the activation of *Escherichia coli* outer membrane protease OmpT, Eur. J. Biochem. FEBS 2002, 269, 1746-1752) discloses that mutations D208A, D210A, H212A, H212N, H212Q, G216K/K217G, K217T and R218 L in loop L4 all resulted in partial or virtually complete loss of enzymatic activity.

Accordingly, the OmpT mutation to produce a protein having reduced protease activity may comprise a mutation, such as a missense mutation to one or more of residues E27, D43, D83, D85, D97, S99, H101 E111, E136, E193, D206, D208, D210, H212 G216, K217, R218 & E250.

One or more of E27, D43, D83, D85, D97, S99, H101 E111, E136, E193, D206, D208, D210, H212 G216, K217, R218 & E250 may be mutated to any suitable amino acid which results in a protein having reduced protease activity. For example, one of more of E27, D43, D83, D85, D97, S99, H101 E111, E136, E193, D206, D208, D210, H212 G216, K217, R218 & E250 may be mutated to alanine. Examples of suitable mutations are E27A, D43A, D83A, D85A, D97A, S99A, H101A E111A, E136A, E193A, D206A, D208A, D210A, H212A, H212N, H212Q, G216K, K217G, K217T, R218 L & E250A. In one embodiment the mutated OmpT gene comprises D210A and H212A mutations. A suitable mutated OmpT sequence comprising D210A and H212A mutations is shown in SEQ ID NO: 23.

The expression "knockout mutated OmpT gene" in the context of the present invention means that the gene comprises one or more mutations thereby causing no expression of the protein encoded by the gene to provide a cell deficient in the protein encoded by the knockout mutated gene. The knockout gene may be partially or completely transcribed but not translated into the encoded protein. The knockout mutated OmpT gene may be mutated in any suitable way, for example by one or more deletion, insertion, point, missense, nonsense and frameshift mutations, to cause no expression of the protein. For example, the gene may be knocked out by insertion of a foreign DNA sequence, such as an antibiotic resistance marker, into the gene coding sequence.

In one embodiment the OmpT gene comprises a mutation to the gene start codon and/or one or more stop codons positioned downstream of the gene start codon and upstream of the gene stop codon thereby preventing expression of the OmpT protein. The mutation to the start codon may be a missense mutation of one, two or all three of the nucleotides of the start codon. A suitable mutated knockout OmpT sequence is shown in SEQ ID NO: 24. Alternatively or additionally the start codon may be mutated by an insertion or deletion frameshift mutation.

In one embodiment the gram-negative bacterial cell according to the present invention does not carry a knockout mutated ompT gene, such as being deficient in chromosomal ompT.

In one embodiment the gram-negative bacterial cell according to the present invention does not carry a knockout mutated degP gene, such as being deficient in chromosomal degP. In one embodiment the gram-negative bacterial cell according to the present invention does not carry a mutated degP gene.

In one embodiment the gram-negative bacterial cell according to the present invention does not carry a knockout mutated ptr gene, such as being deficient in chromosomal ptr.

Many genetically engineered mutations including knockout mutations involve the use of antibiotic resistance markers which allow the selection and identification of successfully mutated cells. However, as discussed above, there are a number of disadvantages to using antibiotic resistance markers.

A further embodiment of the present invention the cell does not comprise an antibiotic resistance marker and overcomes the above disadvantages of using antibiotic resistance markers wherein the mutated Tsp gene, the mutated spr gene and optionally the mutated DegP gene and/or a mutated ptr gene and/or a mutated OmpT gene, are mutated to comprise one or more restriction marker sites. The restriction sites are genetically engineered into the gene and are non-naturally occurring. The restriction marker sites are advantageous because they allow screening and identification of correctly modified cells which comprise the required chromosomal mutations. Cells which have been modified to carry one or more of the mutated protease genes may be analyzed by PCR of genomic DNA from cell lysates using oligonucleotide pairs designed to amplify a region of the genomic DNA comprising a non-naturally occurring restriction marker site. The amplified DNA may then be analyzed by agarose gel electrophoresis before and after incubation with a suitable restriction enzyme capable of digesting the DNA at the non-naturally occurring restriction marker site. The presence of DNA fragments after incubation with the restriction enzyme confirms that the cells have been successfully modified to carry the one or more mutated genes.

In the embodiment wherein the cell carries a knockout mutated ptr gene having the DNA sequence of SEQ ID NO: 6, the oligonucleotide primer sequences shown in SEQ ID NO: 17 and SEQ ID NO: 18 may be used to amplify the region of the DNA comprising the non-naturally occurring Ase I restriction site from the genomic DNA of transformed cells. The amplified genomic DNA may then be incubated with Ase I restriction enzyme and analyzed by gel electrophoresis to confirm the presence of the mutated ptr gene in the genomic DNA.

In the embodiment wherein the cell comprises a knockout mutated Tsp gene having the DNA sequence of SEQ ID NO: 3 or nucleotides 7 to 2048 of SEQ ID NO:3, the oligonucleotide primer sequences shown in SEQ ID NO: 15 and SEQ ID NO:16 may be used to amplify the region of the DNA comprising the non-naturally occurring Ase I restriction site from the genomic DNA of transformed cells. The amplified genomic DNA may then be incubated with Ase I restriction enzyme and analyzed by gel electrophoresis to confirm the presence of the mutated Tsp gene in the genomic DNA.

In the embodiment wherein the cell comprises a mutated DegP gene having the DNA sequence of SEQ ID NO: 9, the oligonucleotide primer sequences shown in SEQ ID NO: 19 and SEQ ID NO:20 may be used to amplify the region of the DNA comprising the non-naturally occurring Ase I restriction site from the genomic DNA of transformed cells. The amplified genomic DNA may then be incubated with Ase I restriction enzyme and analyzed by gel electrophoresis to confirm the presence of the mutated DegP gene in the genomic DNA.

The one or more restriction sites may be introduced by any suitable mutation including by one or more deletion, insertion, point, missense, nonsense and frameshift mutations. A restriction site may be introduced by the mutation of the start codon and/or mutation to introduce the one or more stop codons, as described above. This embodiment is advantageous because the restriction marker site is a direct and unique marker of the knockout mutations introduced.

A restriction maker site may be inserted which comprises an in-frame stop codon, such as an Ase I restriction site. This is particularly advantageous because the inserted restriction site serves as both a restriction marker site and a stop codon to prevent full transcription of the gene coding sequence. For example, in the embodiment wherein a stop codon is introduced to the ptr gene by introduction of an Ase I site, this also creates a restriction site, as shown in FIG. 7A. For example, in the embodiment wherein a stop codon is introduced to the Tsp gene at codon 21 by introduction of an Ase I site, this also creates a restriction site, as shown in FIG. 7B.

A restriction marker site may be inserted by the mutation to the start codon and optionally one or more further point mutations. In this embodiment the restriction marker site is preferably an EcoR I restriction site. This is particularly advantageous because the mutation to the start codon also creates a restriction marker site. For example, in the embodiment wherein the start codon of the ptr gene is changed to ATT, this creates an EcoR I marker site, as shown in FIG. 7A. For example, in the embodiment wherein the start codon (codon 3) of the Tsp gene is changed from ATG to TCG, as shown in FIG. 7B, a further point mutation of codon 2 from AAC to AAT and mutation of codon 3 ATG to TCG creates an EcoR I restriction marker site, as shown in FIG. 7B.

In the embodiment of the present invention wherein the cell carries a mutated OmpT gene, the one or more restriction sites may be introduced by any suitable mutation including by one or more deletion, insertion, point, missense, nonsense and frameshift mutations. For example, in the embodiment wherein the OmpT gene comprises the mutations D210A and H212A, these mutations introduce silent HindIII restriction site which may be used as a selection marker.

In the DegP gene or the spr gene, a marker restriction site may be introduced using silent codon changes. For example, an Ase I site may be used as a silent restriction marker site, wherein the TAA stop codon is out-of-frame, as shown in FIG. 7C for the mutated DegP gene.

In the embodiments of the present invention, wherein the ptr gene and/or the Tsp gene are mutated to encode a Protease III or Tsp having reduced protease activity, one or more marker restriction sites may be introduced using silent codon changes.

The recombinant gram-negative bacterial cell according to the present invention may be produced by any suitable means. The skilled person knows of suitable techniques which may be used to replace a chromosomal gene sequence with a mutated gene sequence. Suitable vectors may be employed which allow integration into the host chromosome by homologous recombination.

Suitable gene replacement methods are described, for example, in Hamilton et al (New Method for Generating Deletions and Gene Replacements in *Escherichia coli*, Hamilton C. M. et al., Journal of Bacteriology September 1989, Vol. 171, No. 9 p 4617-4622), Skorupski et al (Positive selection vectors for allelic exchange, Skorupski K and Taylor R. K., Gene, 1996, 169, 47-52), Kiel et al (A general method for the construction of *Escherichia coli* mutants by homologous recombination and plasmid segregation, Kiel J. A. K. W. et al, Mol Gen Genet 1987, 207:294-301), Blomfield et al (Allelic exchange in *Escherichia coli* using the *Bacillus subtilis* sacB gene and a temperature sensitive pSC101 replicon, Blomfield I. C. et al., Molecular Microbiology 1991, 5(6), 1447-1457) and Ried et al. (An nptI-sacB-sacR cartridge for constructing directed, unmarked mutations in Gram-negative bacteria by marker exchange-eviction mutagenesis, Ried J. L. and Collmer A., Gene 57 (1987) 239-246). A suitable plasmid which enables homologous recombination/replacement is the pKO3 plasmid (Link et al., 1997, *Journal of Bacteriology*, 179, 6228-6237).

Successfully mutated strains may be identified using methods well known in the art including colony PCR DNA sequencing and colony PCR restriction enzyme mapping.

In the embodiment wherein the cell comprises two or more mutated chromosomal genes, the mutated genes may be introduced into the gram-negative bacterium on the same or different vectors.

In one embodiment the gram-negative bacterial cell according to the present invention does not carry a knockout mutated ompT gene, such as being deficient in chromosomal ompT.

In one embodiment the cells according to the present disclosure only contain the three characterizing mutations of mutated spr, reduced Tsp and express FkpA, Skp or a combination of FkpA and Skp.

In one embodiment the cell line according to the present disclosure consists of a mutated Tsp gene and a mutated spr gene, and an FkpA gene.

In one embodiment the cell line according to the present disclosure consists of a mutated Tsp gene and a mutated spr gene, and a Skp gene.

In one embodiment the cell line according to the present disclosure consists of a mutated Tsp gene and a mutated spr gene, an FkpA gene and a Skp gene.

In one embodiment the gene or genes capable of expressing or overexpressing one or more proteins capable of facilitating protein folding, such as FkpA, Skp, SurA, PPiA and PPiD are transiently transformed into the cell, for example in an expression vector optionally comprising a polynucleotide sequence encoding an antibody or binding fragment thereof.

In one embodiment the polynucleotide sequence encoding the antibody and the polynucleotide encoding FkpA and/or Skp are inserted into separate expression vectors.

For production of products comprising both heavy and light chains, the cell line may be transformed with two vectors, a first vector encoding a light chain polypeptide and a second vector encoding a heavy chain polypeptide. Alternatively, a single vector may be used, the vector including sequences encoding light chain and heavy chain polypeptides.

Alternatively, the polynucleotide sequence encoding the antibody and the polynucleotide encoding FkpA and/or Skp are inserted into one vector. Preferably the vector comprises the sequences encoding the light and heavy chain polypeptides of the antibody.

The present invention also provides an expression vector comprising a recombinant polynucleotide encoding FkpA and/or Skp and an antibody or an antigen binding fragment thereof specific for human FcRn. The expression vector is a multi-cistronic vector comprising the polynucleotide sequence encoding FkpA and/or Skp and the polynucleotide sequence encoding the antibody.

The multicistronic vector may be produced by an advantageous cloning method which allows repeated sequential cloning of polynucleotide sequences into a vector. The method uses compatible cohesive ends of a pair of restrictions sites, such as the "AT" ends of Ase I and Nde I restriction sites. A polynucleotide sequence comprising a coding sequence and having compatible cohesive ends, such as a AseI-NdeI fragment, may be cloned into a restrictions site in the vector, such as Nde I. The insertion of the polynucleotide sequence destroys the 5' restriction site but creates a new 3' restriction site, such as NdeI, which may then be used to insert a further polynucleotide sequence comprising compatible cohesive ends. The process may then be repeated to insert further sequences. Each polynucleotide sequence inserted into the vector comprises non-coding sequence 3' to the stop codon which may comprise an Ssp I site for screening, a Shine Dalgarno ribosome binding sequence, an A rich spacer and an NdeI site encoding a start codon.

A diagrammatic representation of the creation of a vector comprising a polynucleotide sequence encoding a light chain of an antibody (LC), a heavy chain of an antibody (HC), an FkpA polynucleotide sequences and a further polynucleotide sequence is shown in FIG. 7d.

The cell according to the present invention preferably comprises an expression vector as defined above.

In the embodiment wherein the cell also expresses one or more further proteins as follows: one or more proteins capable of facilitating protein folding, such as, skp, SurA, PPiA and PPiD; and optionally one or more protein capable of facilitating protein secretion or translocation, such as SecY, SecE, SecG, SecYEG, SecA, SecB, FtsY and Lep; the one or more further protein may be expressed from one or more polynucleotides inserted into the same vector as the polynucleotide encoding FkpA and/or the polynucleotide sequence encoding the antibody. Alternatively the one or more polynucleotides may be inserted into separate vectors.

The expression vector may be produced by inserting one or more expression cassettes as defined above into a suitable vector. Alternatively, the regulatory expression sequences for directing expression of the polynucleotide sequence may be contained in the expression vector and thus only the encoding region of the polynucleotide may be required to complete the expression vector.

The polynucleotide encoding FkpA and/or Skp and/or the polynucleotide encoding the antibody is suitably inserted into a replicable vector, typically an autonomously replicating expression vector, for expression in the cell under the control of a suitable promoter for the cell. Many vectors are known in the art for this purpose and the selection of the appropriate vector may depend on the size of the nucleic acid and the particularly cell type.

Examples of expression vectors which may be employed to transform the host cell with a polynucleotide according to the invention include:
a plasmid, such as pBR322 or pACYC184, and/or
a viral vector such as bacterial phage
a transposable genetic element such as a transposon Such expression vectors usually comprise a plasmid origin of DNA replication, an antibiotic selectable marker, a promoter and transcriptional terminator separated by a multi-cloning site (expression cassette) and a DNA sequence encoding a ribosome binding site.

The promoters employed in the present invention can be linked to the relevant polynucleotide directly or alternatively be located in an appropriate position, for example in a vector such that when the relevant polypeptide is inserted the relevant promoter can act on the same. In one embodiment the promoter is located before the encoding portion of the polynucleotide on which it acts, for example a relevant promoter before each encoding portion of polynucleotide. "Before" as used herein is intended to imply that the promoter is located at the 5 prime end in relation to the encoding polynucleotide portion.

The promoters may be endogenous or exogenous to the host cells. Suitable promoters include lac, tac, trp, phoA, Ipp, Arab, tet and T7.

One or more promoters employed may be inducible promoters. In the embodiment wherein the polynucleotide encoding FkpA and/or Skp and the polynucleotide encoding the antibody are inserted into one vector, the nucleotide sequences encoding FkpA and the antibody may be under the control of a single promoter or separate promoters. In the embodiment wherein the nucleotide sequences encoding FkpA and/or Skp and the antibody are under the control of separate promoters, the promoter may be independently inducible promoters.

Promoters for use in bacterial systems also generally contain a Shine-Dalgamo (S.D.) sequence operably linked to the DNA encoding the polypeptide of interest. The promoter can be removed from the bacterial source DNA by restriction enzyme digestion and inserted into the vector containing the desired DNA.

The expression vector preferably also comprises a dicistronic message for producing the antibody or antigen binding fragment thereof as described in WO03/048208 or WO2007/039714 (the contents of which are incorporated herein by reference). Preferably the upstream cistron contains DNA coding for the light chain of the antibody and the downstream cistron contains DNA coding for the corresponding heavy chain, and the dicistronic intergenic sequence (IGS) preferably comprises a sequence selected from IGS1 (SEQ ID NO: 23), IGS2 (SEQ ID NO: 24), IGS3 (SEQ ID NO: 25) and IGS4 (SEQ ID NO: 26).

The terminators may be endogenous or exogenous to the host cells. A suitable terminator is rrnB.

Further suitable transcriptional regulators including promoters and terminators and protein targeting methods may be found in "Strategies for Achieving High-Level Expression of Genes in *Escherichia coli*" Savvas C. Makrides, Microbiological Reviews, September 1996, p 512-538.

The FkpA polynucleotide inserted into the expression vector preferably comprises the nucleic acid encoding the FkpA signal sequences and the FkpA coding sequence. The vector preferably contains a nucleic acid sequence that enables the vector to replicate in one or more selected host cells, preferably to replicate independently of the host chromosome. Such sequences are well known for a variety of bacteria.

In one embodiment the FkpA and/or Skp and/or the protein of interest comprises a histidine-tag at the N-terminus and/or C-terminus.

The antibody molecule may be secreted from the cell or targeted to the periplasm by suitable signal sequences. Alternatively, the antibody molecules may accumulate within the cell's cytoplasm. Preferably the antibody molecule is targeted to the periplasm.

The polynucleotide encoding the antibody may be expressed as a fusion with another polypeptide, preferably a signal sequence or other polypeptide having a specific cleavage site at the N-terminus of the mature polypeptide. The heterologous signal sequence selected should be one that is recognized and processed by the host cell. For prokaryotic host cells that do not recognize and process the native or a eukaryotic polypeptide signal sequence, the signal sequence is substituted by a prokaryotic signal sequence. Suitable signal sequences include OmpA, PhoA, LamB, PelB, DsbA and DsbC. In an embodiment where the cell comprises a polynucleotide sequence encoding a heavy chain of the antibody and a polynucleotide sequence encoding a light chain of the antibody, each polynucleotide may comprise a signal sequence, such as OmpA.

Construction of suitable vectors containing one or more of the above-listed components employs standard ligation techniques. Isolated plasmids or DNA fragments are cleaved, tailored, and re-ligated in the form desired to generate the plasmids required. General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Standard techniques of molecular biology may be used to prepare DNA sequences coding for the antibody. Desired DNA sequences may be synthesised completely or in part using oligonucleotide synthesis techniques. Site-directed mutagenesis and polymerase chain reaction (PCR) techniques may be used as appropriate.

Embodiments of the invention described herein with reference to the polynucleotide apply equally to alternative embodiments of the invention, for example vectors, expression cassettes and/or host cells comprising the components employed therein, as far as the relevant aspect can be applied to same.

The cell according to the present invention may further comprise a polynucleotide sequence encoding a protein of interest. The polynucleotide sequence encoding the protein of interest may be exogenous or endogenous. The polynucleotide sequence encoding the protein of interest may be integrated into the host's chromosome or may be non-integrated in a vector, typically a plasmid.

In one embodiment the cell according to the present invention expresses a protein of interest. "Protein of interest" in the context of the present specification is intended to refer to polypeptide for expression, usually a recombinant polypeptide. However, the protein of interest may be an endogenous protein expressed from an endogenous gene in the host cell.

As used herein, a "recombinant polypeptide" refers to a protein that is constructed or produced using recombinant DNA technology. The protein of interest may be an exogenous sequence identical to an endogenous protein or a mutated version thereof, for example with attenuated biological activity, or fragment thereof, expressed from an exogenous vector. Alternatively, the protein of interest may be a heterologous protein, not normally expressed by the host cell.

The protein of interest may be any suitable protein including a therapeutic, prophylactic or diagnostic protein.

The skilled person would easily be able to test secreted protein to see if the protein is correctly folded using methods well known in the art, such as protein G HPLC, circular dichroism, NMR, X-Ray crystallography and epitope affinity measurement methods.

In one embodiment the protein of interest is useful in the treatment of diseases or disorders including immunologogical disorders and/or autoimmune diseases.

In one embodiment autoimmune disease is selected from acute disseminated encephalomyelitis (ADEM), acute necrotizing hemorrhagic leukoencephalitis, addison's disease, agammaglobulinemia, alopecia areata, amyloidosis, ANCA-associated vasculitis, ankylosing spondylitis, anti-GBM/Anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, autoimmune urticarial, axonal & neuronal neuropathies, balo disease, Behcet's disease, bullous pemphigoid, cardiomyopathy, Castleman disease, celiac disease, chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, devic's disease (neuromyelitis optica), dilated cardiomyopathy, discoid lupus, dressler's syndrome, endometriosis, eosinophilic angiocentric fibrosis, eosinophilic fasciitis, erythema nodosum, experimental allergic encephalomyelitis, Evans syndrome, fibromyalgia, fibrosing alveolitis, giant cell arteritis (temporal arteritis), glomerulonephritis, Goodpasture's syndrome, granulomatosis with polyangiitis (GPA) see Wegener's, Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic hypocomplementemic tubulointerstitial nephritis, idiopathic thrombocytopenic purpura (ITP), IgA nephropathy, IgG4-related disease, IgG4-related sclerosing disease, immunoregulatory lipoproteins, inflammatory aortic aneurysm, inflammatory pseudotumour, inclusion body myositis, insulin-dependent diabetes (type1), interstitial cystitis, juvenile arthritis, juvenile diabetes, Kawasaki syndrome, Kuttner's tumour, Lambert-Eaton syndrome, leukocytoclastic vasculitis, lichen planus, lichen sclerosus, ligneous conjunctivitis, linear IgA disease (LAD), Lupus (SLE), Lyme disease, chronic, mediastinal fibrosis, meniere's disease, microscopic polyangiitis, Mikulicz's syndrome, mixed connective tissue disease (MCTD), Mooren's ulcer, Mucha-Habermann disease, multifocal fibrosclerosis, multiple sclerosis, myasthenia gravis, myositis, narcolepsy, neuromyelitis optica (Devic's), neutropenia, ocular cicatricial pemphigoid, optic neuritis, ormond's disease (retroperitoneal fibrosis), palindromic rheumatism, PANDAS (Pediatric Autoimmune neuropsychiatric disorders associated with *Streptococcus*), paraneoplastic cerebellar degeneration, paraproteinemic polyneuropathies, paroxysmal nocturnal hemoglobinuria (PNH), Parry Romberg syndrome, Parsonnage-Turner syndrome, pars planitis (peripheral uveitis), pemphigus vulgaris, periaortitis, periarteritis, peripheral neuropathy, perivenous encephalomyelitis, pernicious anemia, POEMS syndrome, polyarteritis *nodosa*, Type I, II, & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reflex sympathetic dystrophy, Reiter's syndrome, relapsing polychondritis, restless legs syndrome, retroperitoneal fibrosis (Ormond's disease), rheumatic fever, rheumatoid arthritis, Riedel's thyroiditis, sarcoidosis, Schmidt syndrome, scleritis, scleroderma, Sjogren's syndrome, Sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombotic, thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, vitiligo, Waldenstrom macroglobulinaemia, warm idiopathic haemolytic anaemia and Wegener's granulomatosis (now termed Granulomatosis with Polyangiitis (GPA).

In one embodiment the neurological disorder is selected from chronic inflammatory demyelinating polyneuropathy (CIDP), Guillain-Barre syndrome, paraproteinemic polyneuropathies, neuromyelitis optica (NMO, NMO spectrum disorders or NMO spectrum diseases), and myasthenia gravis.

In one embodiment the immunology haematology disorder is selected from idiopathic thrombocytopenic purpura (ITP), thrombotic thrombocytopenic purpura (TTP), warm idiopathic haemolytic anaemia, Goodpasture's syndrome, and transplantation donor mismatch due to anti-HLA antibodies.

In one embodiment the disease is selected from myasthenia gravis, neuro-myelitis optica, CIDP, Guillaume-Barre Syndrome, Para-proteinemic Poly neuropathy, Refractory Epilepsy, ITP/TTP, hemolytic anemia, Goodpasture's Syndrome, ABO mismatch, Lupus nephritis, renal vasculitis, sclero-derma, fibrosing alveolitis, dilated cardio-myopathy, Grave's Disease, Type 1 diabetes, auto-immune diabetes, pemphigus, sclero-derma, lupus, ANCA vasculitis, dermatomyositis, Sjogren's disease and rheumatoid arthritis.

In one embodiment the dermatology disorder is selected from bullous pemphigoid, pemphigus vulgaris, ANCA-associated vasculitis and dilated cardiomyopathy.

In one embodiment the antibodies or fragments according to the present disclosure may be employed in prophylaxis or treatment of alloimmune diseases associated with allogenic organ or tissue transplantation or certain neonatal conditions.

The protein may be a proteolytically-sensitive polypeptide, i.e. proteins that are prone to be cleaved, susceptible to cleavage, or cleaved by one or more gram-negative bacterial, such as *E. coli*, proteases, either in the native state or during secretion. In one embodiment the protein of interest is proteolytically-sensitive to a protease selected from DegP, Protease III and Tsp. In one embodiment the protein of interest is proteolytically-sensitive to the protease Tsp. In one embodiment the protein of interest is proteolytically-sensitive to the proteases DegP and Protease III. In one embodiment the protein of interest is proteolytically sensitive to the proteases DegP and Tsp. In one embodiment the protein of interest is proteolytically-sensitive to the proteases Tsp and Protease III. In one embodiment the protein of interest is proteolytically sensitive to the proteases DegP, Protease III and Tsp.

Preferably the protein is a eukaryotic polypeptide.

The protein of interest expressed by the cells according to the invention may, for example be an immunogen, a fusion protein comprising two heterologous proteins or an antibody. Antibodies for use as the protein of interest include monoclonal, multi-valent, multi-specific, humanized, fully human or chimeric antibodies. The antibody can be from any species but is preferably derived from a monoclonal antibody, a human antibody, or a humanized fragment. The antibody can be derived from any class (e.g. IgG, IgE, IgM, IgD or IgA) or subclass of immunoglobulin molecule and may be obtained from any species including for example mouse, rat, shark, rabbit, pig, hamster, camel, llama, goat or human. Parts of the antibody fragment may be obtained from more than one species for example the antibody fragments may be chimeric. In one example the constant regions are from one species and the variable regions from another.

The antibody may be a complete antibody molecule having full length heavy and light chains or a fragment thereof, e.g. VH, VL, VHH, Fab, modified Fab, Fab', F(ab')$_2$, Fv, scFv fragment, or a dual specificity antibody, such as a Fab-dAb or Fab-Fv, as described in WO2009/040562 and WO2010/035012.

In one embodiment the protein is a Fab'.

The antibody may be specific for any target antigen. The antigen may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as 131 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD40 L, CD45, CDW52, CD69, CD134 (OX40), ICOS, BCMP7, CD137, CD27 L, CDCP1, CSF1 or CSF1-Receptor, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, KDR and VEGF, and where appropriate, receptors thereof.

Soluble antigens include interleukins such as IL-1, IL-2, IL-3, IL-4, IL-5, IL-6, IL-8, IL-12, IL-13, IL-14, IL-16 or IL-17, such as IL17A and/or IL17F, viral antigens for example respiratory syncytial virus or cytomegalovirus antigens, immunoglobulins, such as IgE, interferons such as interferon α, interferon β or interferon γ, tumour necrosis factor TNF (formerly known as tumour necrosis factor-α), tumor necrosis factor-β, colony stimulating factors such as G-CSF or GM-CSF, and platelet derived growth factors such as PDGF-α, and PDGF-β and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment the antigen is FcRn.

Antibodies for use in the present disclosure may be obtained using any suitable method known in the art. The FcRn polypeptide/protein including fusion proteins and mutants thereof, including cells (recombinantly or naturally) expressing the polypeptide (such as activated T cells) can be used to produce antibodies which specifically recognise FcRn. The polypeptide may be the 'mature' polypeptide or a biologically active fragment or derivative thereof. The human protein is registered in Swiss-Prot under the number P55899. In one embodiment the immunogen is the FcRn alpha chain or a fragment thereof.

Polypeptides, for use to immunize a host, may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The FcRn polypeptide may in some instances be part of a larger protein such as a fusion protein for example fused to an affinity tag.

Antibodies generated against the FcRn polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

In one embodiment, the antibody may be used to functionally alter the activity of the antigen of interest. For example, the antibody may neutralize, antagonize or agonize the activity of said antigen, directly or indirectly or simply blocks binding of the normal ligand thereto.

The present invention also provides a recombinant gram-negative bacterial cell comprising a mutated Tsp gene, wherein the mutated Tsp gene encodes a Tsp protein having reduced protease activity or is a knockout mutated Tsp gene, a mutant spr gene encoding a mutant spr, a gene capable of expressing or overexpressing one or proteins capable of facilitating protein folding and a polynucleotide sequence encoding an antibody or an antigen binding fragment thereof specific for FcRn.

Various anti-FcRn antibodies and fragments are shown in sequences 36 to 74.

In one embodiment the heavy chain comprises 1, 2 or 3 CDRs independently selected from SEQ ID NO: 36, 37 and 38.

In one embodiment the light chain comprises 1, 2 or 3 CDRs independently selected from SEQ ID NO: 39, 40 and 41.

In one embodiment the antibody heavy chain comprises the sequence given in SEQ ID NO:36 for CDR-H1, the sequence given in SEQ ID NO:37 for CDR-H2 and the sequence given in SEQ ID NO:38 for CDRH3.

In one embodiment the antibody light chain comprises the sequence given in SEQ ID NO:39 for CDR-L1, the sequence given in SEQ ID NO:40 for CDR-L2 and the sequence given in SEQ ID NO:41 for CDRL3.

In one embodiment the antibody heavy chain comprises the sequence given in SEQ ID NO:36 for CDR-H1, the sequence given in SEQ ID NO:37 for CDR-H2, the sequence given in SEQ ID NO:38 for CDRH3, the sequence given in SEQ ID NO:39 for CDR-L1, the sequence given in SEQ ID NO:40 for CDR-L2 and the sequence given in SEQ ID NO:41 for CDRL3.

In one embodiment the cell expresses an antibody molecule with a sequence disclosed herein.

Antibody molecules include antibodies and binding fragments thereof.

Suitably, the humanised antibody according to the present invention has a variable domain comprising human acceptor framework regions as well as one or more of the CDRs provided specifically herein. Thus, provided in one embodiment is a humanised antibody which binds human FcRn wherein the variable domains comprise human acceptor framework regions and non-human donor CDRs. In one example the light chain variable domain comprises the sequence given in SEQ ID NO:50 and the heavy chain variable domain comprises the sequence given in SEQ ID NO:58. In one example the light chain comprises the sequence given in SEQ ID NO:54 and the heavy chain comprises the sequence given in SEQ ID NO:62.

After expression, antibody fragments may be further processed, for example by conjugation to another entity such as an effector molecule.

The term effector molecule as used herein includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy. Effector molecular may be attached to the antibody or fragment thereof by any suitable method, for example an antibody fragment may be modified to attach at least one effector molecule as described in WO05/003171 or WO05/003170 (the contents of which are incorporated herein by reference). WO05/003171 or WO05/003170 also describe suitable effector molecules.

In one embodiment the antibody or fragment thereof, such as a Fab, is PEGylated to generate a product with the required properties, for example similar to the whole antibodies, if required. For example, the antibody may be a PEGylated anti-TNF-α Fab', as described in WO01/094585, preferably having attached to one of the cysteine residues at the C-terminal end of the heavy chain a lysyl-maleimide-derived group wherein each of the two amino groups of the lysyl residue has covalently linked to it a methoxypoly (ethyleneglycol) residue having a molecular weight of about 20,000 Da, such that the total average molecular weight of the methoxypoly(ethyleneglycol) residues is about 40,000 Da, more preferably the lysyl-maleimide-derived group is

[1-[[[2-[[3-(2,5-dioxo-1-pyrrolidinyl)-1-oxopropyl]amino] ethyl]amino]-carbonyl]-1,5-pentanediyl]bis(iminocarbonyl).

In one embodiment a Fab or Fab' according to the present disclosure is conjugated to a human serum albumin molecule or a starch molecule.

The cell may also comprise further polynucleotide sequences encoding one or more further proteins of interest.

In one embodiment one or more E. coli host proteins that in the wild type are known to co-purify with the recombinant protein of interest during purification are selected for genetic modification, as described in Humphreys et al. "Engineering of Escherichia coli to improve the purification of periplasmic Fab' fragments: changing the pI of the chromosomally encoded PhoS/PstS protein", Protein Expression and Purification 37 (2004) 109-118 and WO04/035792 (the contents of which are incorporated herein by reference). The use of such modified host proteins improves the purification process for proteins of interest, especially antibodies, produced in E. coli by altering the physical properties of selected E. coli proteins so they no longer co-purify with the recombinant antibody. Preferably the E. coli protein that is altered is selected from one or more of Phosphate binding protein (PhoS/PstS), Dipeptide binding protein (DppA), Maltose binding protein (MBP) and Thioredoxin.

In one embodiment a physical property of a contaminating host protein is altered by the addition of an amino acid tag to the C-terminus or N-terminus. In a preferred embodiment the physical property that is altered is the isoelectric point and the amino acid tag is a poly-aspartic acid tag attached to the C-terminus. In one embodiment the E. coli proteins altered by the addition of said tag are Dipeptide binding protein (DppA), Maltose binding protein (MBP), Thioredoxin and Phosphate binding protein (PhoS/PstS). In one specific embodiment the pI of the E. coli Phosphate binding protein (PhoS/PstS) is reduced from 7.2 to 5.1 by the addition of a poly-aspartic acid tag (polyD), containing 6 aspartic acid residues to the C-terminus.

Also preferred is the modification of specific residues of the contaminating E. coli protein to alter its physical properties, either alone or in combination with the addition of N or C terminal tags. Such changes can include insertions or deletions to alter the size of the protein or amino acid substitutions to alter pI or hydrophobicity. In one embodiment these residues are located on the surface of the protein. In a preferred embodiment surface residues of the PhoS protein are altered in order to reduce the pI of the protein. Preferably residues that have been implicated to be important in phosphate binding (Bass, U.S. Pat. No. 5,304,472) are avoided in order to maintain a functional PhoS protein. Preferably lysine residues that project far out of the surface of the protein or are in or near large groups of basic residues are targeted. In one embodiment, the PhoS protein has a hexa poly-aspartic acid tag attached to the C-terminus whilst surface residues at the opposite end of the molecule are targeted for substitution. Preferably selected lysine residues are substituted for glutamic acid or aspartic acid to confer a greater potential pI change than when changing neutral residues to acidic ones. The designation for a substitution mutant herein consists of a letter followed by a number followed by a letter. The first letter designates the amino acid in the wild-type protein. The number refers to the amino acid position where the amino acid substitution is being made, and the second letter designates the amino acid that is used to replace the wild-type amino acid. In preferred mutations of PhoS in the present invention lysine residues (K) 275, 107, 109, 110, 262, 265, 266, 309, 313 are substituted for glutamic acid (E) or glutamine (Q), as single or combined mutations, in addition lysine (K) 318 may be substituted for aspartic acid (D) as a single or combined mutation. Preferably the single mutations are K262E, K265E and K266E. Preferably the combined mutations are K265/266E and K110/265/266E. More preferably, all mutations are combined with the polyaspartic acid (polyD) tag attached at the C-terminus and optionally also with the K318D substitution. In a preferred embodiment the mutations result in a reduction in pI of at least 2 units. Preferably the mutations of the present invention reduce the pI of PhoS from 7.2 to between about 4 and about 5.5. In one embodiment of the present invention the pI of the PhoS protein of E. coli is reduced from 7.2 to about 4.9, about 4.8 and about 4.5 using the mutations polyD K318D, polyD K265/266E and polyD K110/265/266E respectively.

The polynucleotide encoding the protein of interest may be expressed as a fusion with another polypeptide, preferably a signal sequence or other polypeptide having a specific cleavage site at the N-terminus of the mature polypeptide. The heterologous signal sequence selected should be one that is recognized and processed by the host cell. For prokaryotic host cells that do not recognize and process the native or a eukaryotic polypeptide signal sequence, the signal sequence is substituted by a prokaryotic signal sequence. Suitable signal sequences include OmpA, PhoA, LamB, PelB, DsbA and DsbC.

Construction of suitable vectors containing one or more of the above-listed components employs standard ligation techniques. Isolated plasmids or DNA fragments are cleaved, tailored, and re-ligated in the form desired to generate the plasmids required.

In one embodiment an expression cassette is employed in the present invention to carry the polynucleotide encoding the protein of interest which typically comprises one or more protein coding sequences encoding one or more proteins of interest and one or more regulatory expression sequences. The one or more regulatory expression sequences may include a promoter. The one or more regulatory expression sequences may also include a 3' untranslated region such as a termination sequence. Suitable promoters are discussed in more detail below.

In one embodiment, the cell according to the present invention comprises a vector, such as plasmid. The vector preferably comprises one or more of the expression cassettes as defined above.

In the embodiment where the protein of interest is an antibody comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The vector for use in the present invention may be produced by inserting an expression cassette as defined above into a suitable vector. Alternatively, the regulatory expression sequences for directing expression of the polynucleotide sequence encoding a protein of interest may be contained in the vector and thus only the encoding region of the polynucleotide may be required to complete the vector.

Examples of vectors which may be employed to transform the host cell with a polynucleotide according to the invention include: a plasmid, such as pBR322 or pACYC184, and/or a viral vector such as bacterial phage, a transposable genetic element such as a transposon.

Many forms of expression vector are available. Such vectors usually comprise a plasmid origin of DNA replication, an antibiotic selectable marker a promoter and transcriptional terminator separated by a multi-cloning site (expression cassette) and a DNA sequence encoding a ribosome binding site.

The promoters employed in the present invention can be linked to the relevant polynucleotide directly or alternatively be located in an appropriate position, for example in a vector such that when the relevant polypeptide is inserted the relevant promoter can act on the same. In one embodiment the promoter is located before the encoding portion of the polynucleotide on which it acts, for example a relevant promoter before each encoding portion of polynucleotide. "Before" as used herein is intended to imply that the promoter is located at the 5 prime end in relation to the encoding polynucleotide portion.

The promoters may be endogenous or exogenous to the host cells. Suitable promoters include lac, tac, trp, phoA, Ipp, Arab, tet and T7.

One or more promoters employed may be inducible promoters.

Expression units for use in bacterial systems also generally contain a Shine-Dalgarno (S. D.) ribosome sequence operably linked to the DNA encoding the polypeptide of interest.

The expression vector preferably also comprises a dicistronic message for producing the antibody or antigen binding fragment thereof as described in WO 03/048208 or WO2007/039714 (the contents of which are incorporated herein by reference). Preferably the upstream cistron contains DNA coding for the light chain of the antibody and the downstream cistron contains DNA coding for the corresponding heavy chain, and the dicistronic intergenic sequence (IGS) preferably comprises a sequence selected from IGS1 (SEQ ID NO: 38), IGS2 (SEQ ID NO: 39), IGS3 (SEQ ID NO: 40) and IGS4 (SEQ ID NO: 41).

The terminators may be endogenous or exogenous to the host cells. A suitable terminator is rrnB.

Further suitable transcriptional regulators including promoters and terminators and protein targeting methods may be found in "Strategies for Achieving High-Level Expression of Genes in *Escherichia coli*" Savvas C. Makrides, Microbiological Reviews, September 1996, p 512-538.

The antibody molecule may be secreted from the cell or targeted to the periplasm by suitable signal sequences. Alternatively, the antibody molecules may accumulate within the cell's cytoplasm. Preferably the antibody molecule is targeted to the periplasm.

Embodiments of the invention described herein with reference to the polynucleotide apply equally to alternative embodiments of the invention, for example vectors, expression cassettes and/or host cells comprising the components employed therein, as far as the relevant aspect can be applied to same.

The present invention also provides a method for producing a recombinant protein of interest comprising expressing the recombinant protein of interest in a recombinant gram-negative bacterial cell as described above in the first or second aspect of the present invention.

The gram negative bacterial cell and protein of interest preferably employed in the method of the present invention are described in detail above.

When the polynucleotide encoding the protein of interest is exogenous the polynucleotide may be incorporated into the host cell using any suitable means known in the art. Typically, the polynucleotide is incorporated as part of an expression vector which is transformed into the cell. Accordingly, in one aspect the cell according to the present invention comprises an expression cassette comprising the polynucleotide encoding the protein of interest.

The polynucleotide sequence can be transformed into a cell using standard techniques, for example employing rubidium chloride, PEG or electroporation.

The method according to the present invention may also employ a selection system to facilitate selection of stable cells which have been successfully transformed with the polynucleotide encoding the protein of interest. The selection system typically employs co-transformation of a polynucleotide sequence encoding a selection marker. In one embodiment, each polynucleotide transformed into the cell further comprises a polynucleotide sequence encoding one or more selection markers. Accordingly, the transformation of the polynucleotide encoding the protein of interest and the one or more polynucleotides encoding the marker occurs together and the selection system can be employed to select those cells which produce the desired proteins.

Cells able to express the one or more markers are able to survive/grow/multiply under certain artificially imposed conditions, for example the addition of a toxin or antibiotic, because of the properties endowed by the polypeptide/gene or polypeptide component of the selection system incorporated therein (e.g. antibiotic resistance). Those cells that cannot express the one or more markers are not able to survive/grow/multiply in the artificially imposed conditions. The artificially imposed conditions can be chosen to be more or less vigorous, as required.

Any suitable selection system may be employed in the present invention. Typically the selection system may be based on including in the vector one or more genes that provides resistance to a known antibiotic, for example a tetracycline, chloramphenicol, kanamycin or ampicillin resistance gene. Cells that grow in the presence of a relevant antibiotic can be selected as they express both the gene that gives resistance to the antibiotic and the desired protein.

In one embodiment, the method according to the present invention further comprises the step of culturing the transformed cell in a medium to thereby express the protein of interest.

An inducible expression system or a constitutive promoter may be used in the present invention to express the protein of interest. Suitable inducible expression systems and constitutive promoters are well known in the art.

Any suitable medium may be used to culture the transformed cell. The medium may be adapted for a specific selection system, for example the medium may comprise an antibiotic, to allow only those cells which have been successfully transformed to grow in the medium.

The cells obtained from the medium may be subjected to further screening and/or purification as required. The method may further comprise one or more steps to extract and purify the protein of interest as required.

The polypeptide may be recovered from the strain, including from the cytoplasm, periplasm, or supernatant.

In one embodiment the antibody is isolated from the periplasm.

In one embodiment the post induction feed rate is in the range 5 to 7.5 g/h, such as about 7 g/h.

The specific method (s) used to purify a protein depends on the type of protein. Suitable methods include fractionation on immuno-affinity or ion-exchange columns; ethanol precipitation; reversed-phase HPLC; hydrophobic-interaction chromatography; chromatography on silica; chromatography on an ion-exchange resin such as S-SEPHAROSE and DEAE; chromatofocusing; ammonium-sulfate precipitation; and gel filtration.

Antibodies may be suitably separated from the culture medium and/or cytoplasm extract and/or periplasm extract by conventional antibody purification procedures such as, for example, protein A-Sepharose, protein G chromatography, protein L chromatograpy, thiophilic, mixed mode resins, His-tag, FLAGTag, hydroxylapatite chromatography, gel electrophoresis, dialysis, affinity chromatography, Ammonium sulphate, ethanol or PEG fractionation/precipitation, ion exchange membranes, expanded bed adsorption chromatography (EBA) or simulated moving bed chromatography.

The method may also include a further step of measuring the quantity of expression of the protein of interest and selecting cells having high expression levels of the protein of interest.

The method may also include one or more further downstream processing steps such as PEGylation of the protein of interest, such as an antibody or antibody fragment.

One or more method steps described herein may be performed in combination in a suitable container such as a bioreactor. The antibodies and fragments according to the present disclosure may be employed in treatment or prophylaxis.

Where technically appropriate embodiments of the invention may be combined. Embodiments are described herein as comprising certain features/elements. The disclosure also extends to separate embodiments consisting or consisting essentially of said features/elements. Technical references herein, such as patents & applications are incorporated herein by reference.

The present invention is further described by way of illustration only in the following examples, which refer to the accompanying Figures.

EXAMPLES

Example 1: Generation of Cell Lines

The generation of MXE016 and MXE017 is given in WO2011/086136.

Generation of plasmids for anti-FcRn Fab' expression and anti-FcRn Fab' with FkpA, anti-FcRn Fab' with skp and anti-FcRn Fab with both FkpA and skp expression.

A plasmid was constructed containing both the heavy and light chain sequences of an anti-FcRn Fab (SEQ ID NOs: 63 and 55, respectively). Plasmid pTTOD 1519.g57 Fab', was constructed using conventional restriction cloning methodologies which can be found in Sambrook et al 1989, Molecular cloning: a laboratory manual. CSHL press, N.Y. The plasmid pTTOD 1519.g57 Fab' contained the following features; a strong tac promoter and lac operator sequence. The plasmid contained a unique EcoRI restriction site after the coding region of the Fab' heavy chain, followed by a non-coding sequence containing a strong ribosome binding site and then a unique NdeI restriction site.

The Fab light chain, heavy chain genes were transcribed as a single polycistronic message. DNA encoding the signal peptide from the E. coli OmpA protein was fused to the 5' end of both light and heavy chain gene sequences, which directed the translocation of the polypeptides to the E. coli periplasm. Transcription was terminated using a dual transcription terminator rrnB t1t2. The laclq gene encoded the constitutively expressed Lac I repressor protein. This repressed transcription from the tac promoter until de-repression was induced by the presence of allolactose or IPTG. The origin of replication used was p15A, which maintained a low copy number. The plasmid contained a tetracycline resistance gene for antibiotic selection.

Plasmid pTTOD 1519.g57 Fab' FkpA, an expression vector for the anti-FcRn Fab and FkpA (a periplasmic polypeptide), was constructed by ligating FkpA to the 3'end of the Fab' sequence of pTTOD 1519.g57 Fab' using the EcoRI and NdeI sites (See FIG. 7d). The FkpA (SEQ ID NO:30) was synthetically constructed to remove 2 Puv II sites, an SfuI site, a BamHI site and an EcoRI, such that the new construct encoded for a 5' EcoRI site followed by a strong ribosome binding site, followed by the native start codon, signal sequence and mature sequence of FkpA, terminating in a C-terminal His tag and finally a strong ribosome binding site followed by a non-coding NdeI site. The EcoRI-NdeI restriction fragment was restricted and ligated into the expression vector such that all three polypeptides: Fab' light chain, Fab' heavy chain and FkpA were encoded on a single polycistronic mRNA.

Plasmid pTTOD 1519.g57 Fab' Skp, an expression vector for the anti-FcRn Fab and Skp (a periplasmic polypeptide), was constructed by ligating skp to the 3'end of the Fab' sequence of plasmid pTTOD 1519.g57 Fab' using the EcoRI and NdeI sites The skp (SEQ ID NO:34) was synthetically constructed to remove 4 Pst I sites and an EcoRV site, such that the new construct encoded for a 5' EcoRI site followed by a strong ribosome binding site, followed by the native start codon, signal sequence and mature sequence of Skp, terminating in a C-terminal His tag and finally a strong ribosome binding site followed by a non-coding NdeI site. The EcoRI-NdeI restriction fragment was restricted and ligated into the expression vector such that all three polypeptides: Fab' light chain, Fab' heavy chain and skp were encoded on a single polycistronic mRNA.

Plasmid pTTOD 1519.g57 Fab' FkpA Skp an expression vector for the anti-FcRn Fab, FkpA and Skp (both periplasmic polypeptides), was constructed by ligating Skp into plasmid pTTOD 1519.g57 Fab' FkpA, at the 3'end of the FkpA sequence using the NdeI site. The Skp (SEQ ID NO:34) was synthetically constructed to remove 4 Pst I sites and an EcoRV site, such that the construct encoded for a 5' Ase I site including the native start codon, signal sequence and mature sequence of skp, terminating in a C-terminal His tag and finally a non-coding NdeI site. The AseI-NdeI restriction fragment was restricted and ligated into the expression vector such that all four polypeptides: Fab' light chain, Fab' heavy chain, FkpA and Skp were encoded on a single polycistronic mRNA.

Fermentation of pTTOD 1519.g57 Fab', pTTOD 1519.g57 Fab' FkpA, pTTOD 1519.g57 Fab' Skp and pTTOD 1519.g57 Fab' FkpA skp in E. coli W3110, MXE012 (E. coli W3110 spr H145A), MXE016 (E. coli W3110 ΔTsp, spr C94A) and MXE017 (E. coli W3110 ΔTsp, spr H145A).

The E. coli strains W3110, MXE012, MXE016 and MXE017 were transformed with the plasmids pTTOD 1519.g57 Fab', pTTOD 1519.g57 Fab' FkpA, pTTOD 1519.g57 Fab' Skp and pTTOD 1519.g57 Fab' FkpA Skp generated in Example 1. The transformation of the strains was carried out using the method found in Chung C. T et al Transformation and storage of bacterial cells in the same solution. PNAS 86:2172-2175 (1989). These transformed strains were tested for expression by fermentation.

Example 2: Effect of Chaperones on Fab' Expression

The strains shown in FIG. 1 were tested in 1 L and 2.5 L fermentation experiments comparing expression of Fab':

Growth Medium, Inoculum and Fermentation Steps.

The fermentation process was initiated by preparing an inoculum from a vial of the cell bank and amplifying through several pre-culture stages (flask and reactors) before seeding of the production fermenter. In the production fermenter, the cells were grown in defined media to high density in batch and fed-batch mode. When the desired cell density was reached expression of the Fab' was induced by the addition of IPTG. The Fab' expression is targeted to the *E. coli* periplasmic space, where Fab' accumulates throughout the course of the induction phase. A carbon source feed was applied during the induction phase to control expression and cell growth. Temperature, dissolved oxygen ($pO_2$) and pH were controlled to maintain the culture within optimal culture conditions.

Measurement of Biomass Concentration and Growth Rate.

Biomass concentration was determined by measuring the optical density of cultures at 600 nm.

Periplasmic Extraction.

Cells were collected from culture samples by centrifugation. The supernatant fraction was retained (at −20° C.) for further analysis. The cell pellet fraction was resuspended to the original culture volume in extraction buffer (100 mM Tris-HCl, 10 mM EDTA; pH 7.4). Following incubation at 60° C. for approximately 10 to 12 hours the extract was clarified by centrifugation and the supernatant fraction used fresh or retained (at −20° C.) for analysis.

Fab' Quantification.

Fab' concentrations in periplasmic extracts and culture supernatants were determined by using Protein G HPLC. A HiTrap Protein-G HP 1 ml column (GE-Healthcare or equivalent) was loaded with analyte (approximately neutral pH, 30° C., 0.2 μm filtered) at 2 ml/min, the column was washed with 20 mM phosphate, 50 mM NaCl pH 7.4 and then Fab' was eluted using an injection of 50 mM Glycine/HCl pH 2.7. Eluted Fab' was measured by A280 on an Agilent 1100 or 1200 HPLC system and quantified by reference to a standard curve of a purified Fab' protein of known concentration.

FIG. 1 shows the results of 46 fermentations on the 5 L scale performed with various
combinations of host cells and "chaperone". W3110 is a wild-type *E coli* strain. The various combinations were: wild type with no chaperone, wild-type with FkpA and Skp, MXE016 mutant spr and Δ Tsp published in WO2011/086136, MXE016 and FkpA, MXE016 and Skp, MXE016 and FkpA and Skp, MXE017 disclosed in WO2011/086136, MXE017 and FkpA and Skp.

The results show that MXE016, MXE016 and FkpA, MXE016 and FkpA and Skp, and MXE017 and FkpA and Skp showed the best levels of expression.

Example 3: Effect of Post Induction Feed Rate

The effect of three different post induction feed rates 5.4, 6.0 and 7.0 g/h was tested on MXE016 and MXE016+FkpA.

Growth Medium, Inoculum and Fermentation Steps.

The fermentation process was initiated by preparing an inoculum from a vial of the cell bank and amplifying through several pre-culture stages (flask and reactors) before seeding of the production fermenter. In the production fermenter, the cells were grown in defined media to high density in batch and fed-batch mode. When the desired cell density was reached expression of the Fab' was induced by the addition of IPTG. The Fab' expression is targeted to the *E. coli* periplasmic space, where Fab' accumulates throughout the course of the induction phase. A carbon source feed was applied during the induction phase to control expression and cell growth, in this experiment the feed rate set at three separate setpoints (shown in the figure). Temperature, dissolved oxygen ($pO_2$) and pH were controlled to maintain the culture within optimal culture conditions.

FIG. 2 shows strain MXE016 transformed with plasmids expressing either no chaperone or FkpA. The figure shows the effect of increasing the post-induction feed rate on Fab' production and retention in the periplasm both with and without FkpA. The data shows that when the feed rate is increased without FkpA expression the additional Fab' produced is lost to the supernatant. This is not the case with expression of FkpA where the additional Fab' produced at higher feed rates is retained within the periplasm resulting in a higher titre.

Example 4: Analysis of Yield and Cell Viability

Figure 3B:
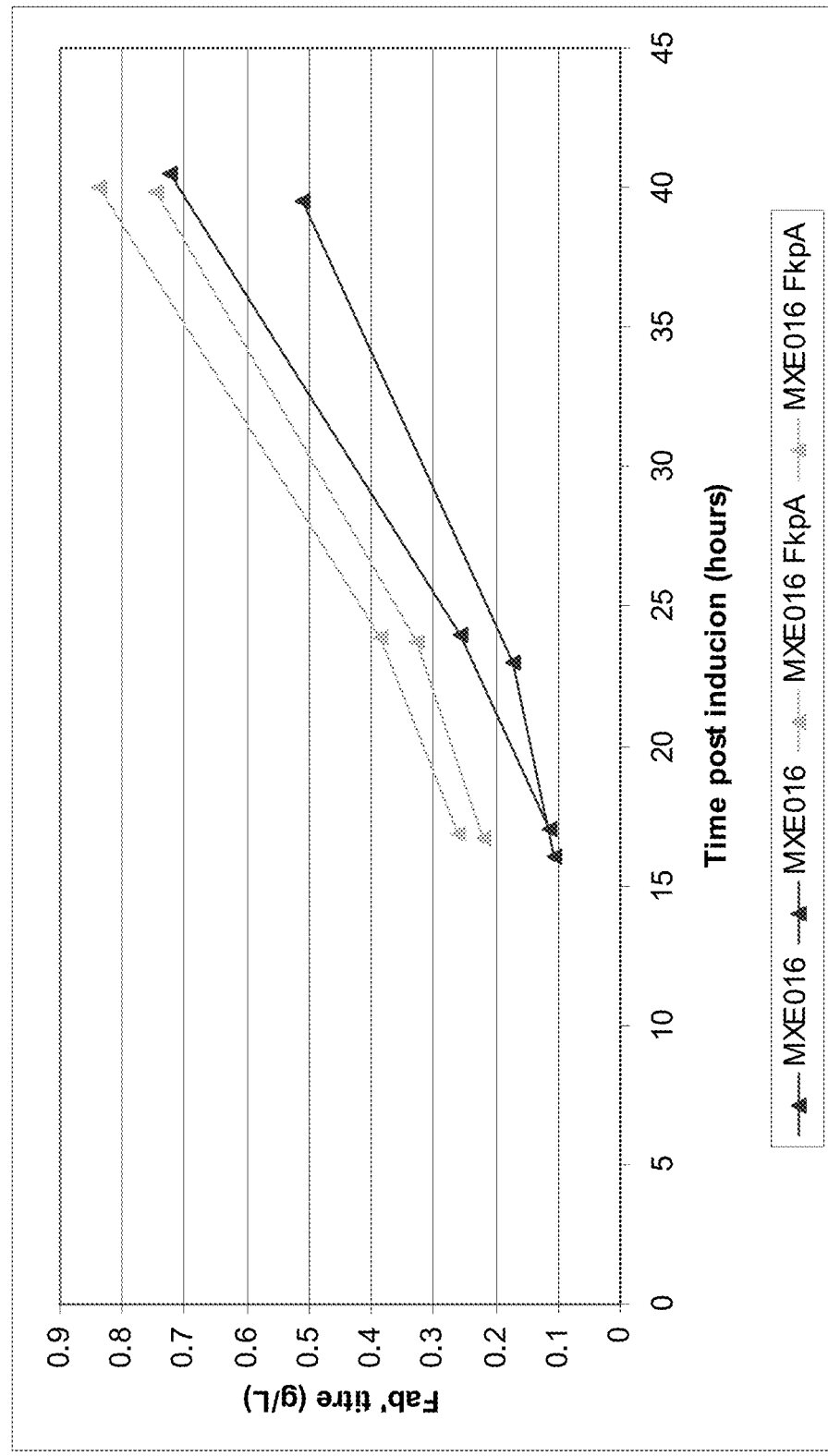

FIGS. 3A and B show effect on cell viability and Fab' titre in MXE016 transformed with plasmids expressing either no chaperone or FkpA at 20 L scale. FIG. 3A shows that cell viability is lower where no FkpA is present. 3b shows that Fab' titres were higher and less variable for MXE016+FkpA.

FIG. 4 shows the higher titre with MXE016+FkpA results in 30% more Fab' following
primary Fab product recovery.

FIGS. 5 and 6 show SDS-PAGE and anti-his-tag western blots of samples from the primary recovery of MXE016 with no chaperone and MXE016 with FkpA expression.

Samples were loaded according to Fab' concentration with 1 μg of Fab' loaded per lane. Gels were 4-20% Tris-Glycine Novex and were run under non-reducing conditions at 125V for 2 hours. Gels were stained with Sypro Ruby stain and imaged. The western blots were transferred to a PVDF membrane using an Invitrogen iBlot system and then blocked with 1% casein solution. The membranes were then probed with an anti-his HRP conjugate antibody (Novagen). The blots were then developed with ECL solution and imaged using an Amersham Life Sciences HyperProcessor.

While this invention has been particularly shown and described with reference to preferred embodiments, it will be understood to those skilled in the art that various changes in form and detail may be made without departing from the scope of the invention as defined by the appendant claims.

We claim:

1. A recombinant gram-negative bacterial cell, said recombinant gram-negative bacterial cell being an *E. coli* K12 or *E. coli* W3110 cell that is isogenic to a wild-type cell except for the following genetic modifications:
   (a) a mutant spr gene encoding a spr protein having a mutation at one or more amino acids selected from H145 and C94;
   (b) an expression vector comprising a FkpA gene operably linked to a promoter, said FkpA gene comprising SEQ ID NO: 30;
   (c) a mutation to the tsp gene that reduces Tsp protein activity as compared to the wild-type cell or knocks out Tsp protein activity;
   (d) optional introduction of a polynucleotide sequence encoding a protein of interest;
   (e) optional knockout of DegP;
   (f) optional mutation of ptr, wherein the mutated ptr gene encodes a Protease III protein having reduced protease activity or is a knockout mutated ptr gene; and
   (g) optional mutation of OmpT, wherein the mutated OmpT gene encodes an OmpT protein having reduced protease activity or is a knockout mutated OmpT gene.

2. The cell according to claim 1, wherein the mutant spr gene encodes a spr protein having an H145 mutation.

3. The cell according to claim 2, wherein the mutant spr gene encodes a spr protein having a H145A mutation.

4. The cell according to claim 1, wherein the mutant spr gene encodes a spr protein having a C94 mutation.

5. The cell according to claim 4, wherein the mutant spr gene encodes a spr protein having a C94A mutation.

6. The cell according to claim 1, wherein the mutant spr gene encodes a spr protein having the mutations.

7. The cell according to claim 1, wherein the mutant spr gene is integrated into the genome of the cell.

8. The cell according to claim 1, said expression vector being integrated into the cell's genome.

9. The cell according to claim 1, wherein the cell further has one or more of the following mutated genes:
   (a) a knockout mutated DegP gene;
   (b) a mutated ptr gene, wherein the mutated ptr gene encodes a Protease III protein having reduced protease activity or is a knockout mutated ptr gene; and
   (c) a mutated OmpT gene, wherein the mutated OmpT gene encodes an OmpT protein having reduced protease activity or is a knockout mutated OmpT gene.

10. The cell according to claim 1, wherein the cell contains a knockout mutated Tsp gene.

11. The cell according to claim 1, wherein the cell is *E. coli* strain K12.

12. The cell according to claim 1, wherein the cell contains a polynucleotide sequence encoding a protein of interest.

13. The cell according to claim 12, wherein the protein of interest is an antibody or an antigen binding fragment thereof.

14. The cell according to claim 13, wherein the antibody or antigen binding fragment thereof is specific for FcRn.

15. The cell according to claim 1, wherein the mutant spr gene encodes a spr protein having mutations C94 and H145.

16. The cell according to claim 1, wherein the cell is *E. coli* strain W3110.

17. A method for producing a recombinant protein of interest comprising culturing a recombinant gram-negative bacterial cell of claim 1 in a culture medium under conditions effective to express the recombinant protein of interest and recovering the recombinant protein of interest from the periplasm of the recombinant gram-negative bacterial cell and/or the culture medium.

18. The method according to claim 17, wherein the recombinant protein of interest is recovered from the periplasm of the recombinant gram-negative bacterial cell.

19. The method according to claim 18, wherein the recombinant protein of interest is recovered from the periplasm of the recombinant gram-negative bacterial cell and the culture medium.

20. The cell according to claim 1, said cell consisting of:
  (a) a mutant spr gene encoding a spr protein having a mutation at one or more amino acids selected from H145 and C94;
  (b) an expression vector comprising a FkpA gene operably linked to a promoter, said FkpA gene comprising SEQ ID NO: 30;
  (c) a knockout mutation to the tsp gene; and
  (d) a polynucleotide sequence encoding a protein of interest, said recombinant gram-negative bacterial cell being *E. coli* K12 or *E. coli* W3110.

* * * * *

UNITED STATES PATENT AND TRADEMARK OFFICE
CERTIFICATE OF CORRECTION

PATENT NO. : 11,261,470 B2
APPLICATION NO. : 15/959498
DATED : March 1, 2022
INVENTOR(S) : Philip Jonathan Bassett, David Paul Humphreys and Pareshkumar Manjibhai Patel Page 1 of 1

It is certified that error appears in the above-identified patent and that said Letters Patent is hereby corrected as shown below:

In the Specification

Column 28,
Line 55, "131 integrins" should read --β1 integrins--.

In the Claims

Column 126,
Line 54, Claim 26 "mutations" should read --mutations C94A and H145A--.

Signed and Sealed this
Twenty-second Day of November, 2022

Katherine Kelly Vidal
*Director of the United States Patent and Trademark Office*